United States Patent
Xia et al.

(10) Patent No.: US 8,129,358 B2
(45) Date of Patent: *Mar. 6, 2012

(54) SUBSTITUTED PYRAZOLE AND TRIAZOLE COMPOUNDS AS KSP INHIBITORS

(75) Inventors: Yi Xia, Palo Alto, CA (US); Kris G. Mendenhall, Concord, CA (US); Paul A. Barsanti, Pleasant Hill, CA (US); Annette O. Walter, Mill Valley, CA (US); David Duhl, Oakland, CA (US); Paul A. Renhowe, Danville, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/312,389

(22) PCT Filed: Nov. 8, 2007

(86) PCT No.: PCT/US2007/084154
§ 371 (c)(1),
(2), (4) Date: Oct. 21, 2009

(87) PCT Pub. No.: WO2008/063912
PCT Pub. Date: May 29, 2008

(65) Prior Publication Data
US 2010/0034813 A1    Feb. 11, 2010

Related U.S. Application Data

(60) Provisional application No. 60/858,964, filed on Nov. 13, 2006.

(51) Int. Cl.
| | | |
|---|---|---|
| A61K 31/553 | (2006.01) |
| A61K 31/54 | (2006.01) |
| A61K 31/535 | (2006.01) |
| A61K 31/495 | (2006.01) |
| A61K 31/505 | (2006.01) |
| A61K 31/44 | (2006.01) |
| A61K 31/445 | (2006.01) |
| A61K 31/41 | (2006.01) |
| C07D 267/02 | (2006.01) |
| C07D 279/10 | (2006.01) |
| C07D 413/02 | (2006.01) |
| C07D 211/30 | (2006.01) |
| C07D 401/02 | (2006.01) |
| C07D 249/08 | (2006.01) |

(52) U.S. Cl. ............ 514/49; 514/211.03; 514/227.8; 514/236.2; 514/252.18; 514/274; 514/283; 514/326; 514/340; 514/383; 540/488; 544/58.2; 544/58.4; 544/132; 546/247; 546/272.4; 548/267.6

(58) Field of Classification Search ........... 514/49, 514/211.03, 227.8, 236.2, 252.18, 274, 283, 514/326, 340, 383; 540/488; 544/58.2, 58.4, 544/132; 546/247, 272.4; 548/267.6
See application file for complete search history.

(56) References Cited

U.S. PATENT DOCUMENTS

| | | | |
|---|---|---|---|
| 4,235,871 A | 11/1980 | Papahadjopoulos et al. |
| 4,501,728 A | 2/1985 | Geho et al. |
| 4,837,028 A | 6/1989 | Allen |
| 5,011,472 A | 4/1991 | Aebischer et al. |
| 5,023,252 A | 6/1991 | Hseih et al. |
| 5,185,450 A | 2/1993 | Owen |
| 6,545,004 B1 | 4/2003 | Finer et al. |
| 6,562,831 B1 | 5/2003 | Finer et al. |
| 6,630,479 B1 | 10/2003 | Finer et al. |
| 7,902,240 B2 * | 3/2011 | Xia et al. ............ 514/383 |
| 2005/0228002 A1 | 10/2005 | Wang et al. |
| 2005/0261337 A1 | 11/2005 | Wang et al. |
| 2006/0084687 A1 | 4/2006 | Boyce et al. |
| 2007/0037853 A1 | 2/2007 | Barsanti et al. |
| 2007/0270473 A1 | 11/2007 | Saunders et al. |

FOREIGN PATENT DOCUMENTS

| | | |
|---|---|---|
| WO | WO 00/59887 | 10/2000 |
| WO | WO 01/30768 A1 | 5/2001 |
| WO | WO 02/28839 A1 | 4/2002 |
| WO | WO 02/056880 A1 | 7/2002 |
| WO | WO 02/057244 A1 | 7/2002 |
| WO | WO 03/039480 A2 | 5/2003 |
| WO | WO 03/043995 A1 | 5/2003 |
| WO | WO 03/049527 A2 | 6/2003 |
| WO | WO 03/049678 A2 | 6/2003 |
| WO | WO 03/049679 A2 | 6/2003 |

(Continued)

OTHER PUBLICATIONS

Golub et al. Science (1999), vol. 286 531-537.*
Lala et al. Cancer and Metastasis Reviews (1998), 17(1), 91-106.*
Coleman, Paul et al., "Inhibitors of the Mitotic Kinesin Spindle Protein" Expert Opin. Ther Patents, 2004 14(12):1659-1667.
U.S. Appl. No. 11/969,164, filed Jan. 3, 2008, Boyce et al.
Blangy, A. et al., "Phosphorylation by p34$^{cdc2}$ Regulates Spindle Assoication of Human Eg5, a Kinesin-Related Motor Essential for Bipolar Spindle Formation In Vivo", Cell 83:1159-1169, 1995.

(Continued)

Primary Examiner — Rebecca Anderson
Assistant Examiner — Samantha Shterengarts
(74) Attorney, Agent, or Firm — Michael G. Smith

(57) ABSTRACT

Disclosed are new substituted pyrazole and triazole compounds of Formula (I) and pharmaceutically acceptable salts, esters or prodrugs thereof, compositions of the derivatives together with pharmaceutically acceptable carriers, and uses thereof:

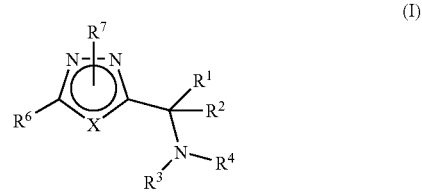

(I)

63 Claims, No Drawings

FOREIGN PATENT DOCUMENTS

| | | |
|---|---|---|
| WO | WO 03/050064 A2 | 6/2003 |
| WO | WO 03/050122 A2 | 6/2003 |
| WO | WO 03/059289 A2 | 7/2003 |
| WO | WO 03/070701 A2 | 8/2003 |
| WO | WO 03/079973 A2 | 10/2003 |
| WO | WO 03/094839 A2 | 11/2003 |
| WO | WO 03/097053 A1 | 11/2003 |
| WO | WO 03/099211 A2 | 12/2003 |
| WO | WO 03/103575 A2 | 12/2003 |
| WO | WO 03/105855 A1 | 12/2003 |
| WO | WO 03/106417 A1 | 12/2003 |
| WO | WO 2004/004652 A2 | 1/2004 |
| WO | WO 2004/006865 A2 | 1/2004 |
| WO | WO 2004/009036 A2 | 1/2004 |
| WO | WO 2004/018058 A2 | 3/2004 |
| WO | WO 2004/024086 A2 | 3/2004 |
| WO | WO 2004/026226 A1 | 4/2004 |
| WO | WO 2004/100873 A2 | 11/2004 |
| WO | WO 2004/103282 A2 | 12/2004 |
| WO | WO 2006/002236 A1 | 1/2006 |

OTHER PUBLICATIONS

Coleman, P.J. et al., "Inhibitors of the Mitotic Kinesin Spindle Protein". Expert Opinion on Therapeutic Patents, Ashely Publications, 14(12):1659-1668, 2004.

Debonis, S., et al., "Interaction of the Mitotic Inhibitor Monastrol With Human Kinesin EG5". *Biochemistry*, 2003, 42:338-349.

Enos, A.P. et al. "Mutation of a Gene That Encodes a Kinesin-like Protein Blocks Nuclear Division in *A. nidulans*". *Cell* 60:1019-1027, 1990.

Giet, R., et al., "The *Xenopus laevis Aurora*-related Protein kinase pEg2 Associates with and Phosphorylates the Kinesin-related Protein XlEg5". *J. Biol. Chem.* 274(21):15005-15013, 1999.

Hagan, I. et al., "Novel Potential Mitotic Motor Protein Encoded by the Fission Yeast *Cut7*+ Gene". *Nature* 347:563-566, 1990.

Kaiser, A., et al., "All-trans-Retinoic Acid-mediated Growth Inhibition Involves Inhibition of Human Kenesin-related Protein HsEg5". *J. Biol. Chem.* 274(27):18925-18931, 1999.

Kapoor, T.M., et al., "Probing Spindle Assembly Mechanisms with Monastrol, a Small Molecule Inhibitor of the Mitotic Kinesin, Eg5". *J. Cell Biol.*, 150(5):975-988, 2000.

Mayer, T.U., et al., "Small Molecule Inhibitor of Mitotic Spindle Bipolarity Identified in a Phenotype-Based Screen". *Science* 286:971-974, 1999.

Notice of Allowability dated Oct. 28, 2010 for U.S. Appl. No. 11/937,426.

Examiner's Office Action dated Oct. 8, 2009 for U.S. Appl. No. 11/937,426.

* cited by examiner

SUBSTITUTED PYRAZOLE AND TRIAZOLE COMPOUNDS AS KSP INHIBITORS

CROSS-REFERENCE TO RELATED APPLICATION

This application claims the benefit under 35 U.S.C. §119(e) to U.S. provisional application Ser. No. 60/858,964, filed on Nov. 13, 2006, which is incorporated herein by reference in its entirety.

BACKGROUND OF THE INVENTION

1. Field of the Invention

This invention generally relates to substituted pyrazole and triazole compounds and pharmaceutically acceptable salts, esters, or prodrugs thereof. This invention is further directed to compositions of such compounds together with pharmaceutically acceptable carriers, to uses of such compounds, to their preparation, and to related intermediates.

2. State of the Art

Kinesins are motor proteins that use adenosine triphosphate to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmic reticulum. Several KRPs interact with the microtubules of the mitotic spindle or with the chromosomes directly and appear to play a pivotal role during the mitotic stages of the cell cycle. These mitotic KRPs are of particular interest for the development of cancer therapeutics.

Kinesin spindle protein (KSP) (also known as Eg5, HsEg5, KNSL1, or KIF11) is one of several kinesin-like motor proteins that are localized to the mitotic spindle and known to be required for formation and/or function of the bipolar mitotic spindle.

In 1995, the depletion of KSP using an antibody directed against the C-terminus of KSP was shown to arrest HeLa cells in mitosis with monoastral microtubule arrays (Blangy et al., Cell 83:1159-1169, 1995). Mutations in bimC and cut7 genes, which are considered to be homologues of KSP, cause failure in centrosome separation in *Aspergillus nidulans* (Enos, A. P., and N. R. Morris, Cell 60:1019-1027, 1990) and *Schizosaccharomyces pombe* (Hagan, I., and M. Yanagida, Nature 347:563-566, 1990). Treatment of cells with either ATRA (all trans-retinoic acid), which reduces KSP expression on the protein level, or depletion of KSP using antisense oligonucleotides revealed a significant growth inhibition in DAN-G pancreatic carcinoma cells indicating that KSP might be involved in the antiproliferative action of all trans-retinoic acid (Kaiser, A., et al., J. Biol. Chem. 274, 18925-18931, 1999). Interestingly, the *Xenopus laevis* Aurora-related protein kinase pEg2 was shown to associate and phosphorylate XlEg5 (Giet, R., et al., J. Biol. Chem. 274:15005-15013, 1999). Potential substrates of Aurora-related kinases are of particular interest for cancer drug development. For example, Aurora 1 and 2 kinases are overexpressed on the protein and RNA level and the genes are amplified in colon cancer patients.

The first cell permeable small molecule inhibitor for KSP, "monastrol," was shown to arrest cells with monopolar spindles without affecting microtubule polymerization as do conventional chemotherapeutics such as taxanes and vinca alkaloids (Mayer, T. U., et al., Science 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., Biochemistry, 42:338-349, 2003; Kapoor, T. M., et al., J. Cell Biol., 150:975-988, 2000).

In light of the importance of improved chemotherapeutics, there is a need for KSP inhibitors that are effective in vivo inhibitors of KSP and KSP-related proteins.

SUMMARY OF THE INVENTION

In one embodiment, this invention is directed to substituted pyrazole and triazole compounds and the pharmaceutically acceptable salts, esters, or prodrugs thereof, their preparation, pharmaceutical compositions, and uses for treating KSP mediated diseases, wherein the compounds are represented by the Formula (I):

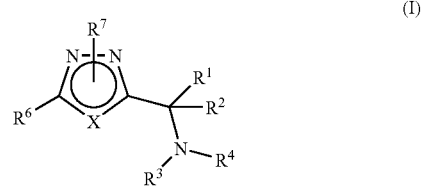

wherein:

$R^1$ is selected from the group consisting of alkyl and substituted alkyl;

$R^2$ is selected from the group consisting of hydrogen, alkyl, and substituted alkyl;

$R^3$ is selected from the group consisting of -$L^1$-$A^1$, wherein $L^1$ is selected from the group consisting of —C(O)—, —C(S)—, —S(O)—, and —S(O)$_2$— and $A^1$ is selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, substituted heterocycloalkyl, and NR$^8$R$^9$;

$R^4$ is selected from the group consisting of hydrogen, alkyl, substituted alkyl, alkenyl, substituted alkenyl, alkynyl, and substituted alkynyl;

or $R^3$ and $R^4$ together with the atoms bound respectively thereto join to form a five to seven membered heterocycloalkyl or substituted heterocycloalkyl group where optionally one additional ring atom is selected from the group consisting of O, S, or NR$^{11}$;

X is CR$^5$ or N;

$R^5$ is selected from the group consisting of hydrogen, halo, alkyl, and substituted alkyl;

$R^6$ is selected from the group consisting of cycloalkyl, heterocycloalkyl, aryl, and heteroaryl, all of which may be optionally substituted with —(R$^{10}$)$_m$ where R$^{10}$ is as defined herein, m is 1, 2, 3, or 4, and each R$^{10}$ may be the same or different when m is 2, 3, or 4;

$R^7$ is -$L^2$-$A^2$ wherein $L^2$ is $C_1$-$C_5$ alkylene and $A^2$ is selected from the group consisting of aryl, substituted aryl, heteroaryl, substituted heteroaryl, cycloalkyl, substituted cycloalkyl, heterocycloalkyl, and substituted heterocycloalkyl, provided that R$^7$ is not attached to X;

$R^8$ is selected from the group consisting of hydrogen and alkyl;

R⁹ is selected from the group consisting of hydrogen, hydroxy, alkyl, substituted alkyl, aryl, substituted aryl, heteroaryl, substituted heteroaryl, cycloalkyl, substituted cycloalkyl, heterocycloalkyl, and substituted heterocycloalkyl;

or R⁸ and R⁹ together with the nitrogen atom pendent thereto join to form a heterocycloalkyl or substituted heterocycloalkyl;

R¹⁰ is selected from the group consisting of cyano, alkyl, substituted alkyl, alkenyl, substituted alkenyl, alkynyl, substituted alkynyl, —CF₃, alkoxy, substituted alkoxy, halo, and hydroxy; and R¹¹ is selected from the group consisting of hydrogen, alkyl, substituted alkyl, —SO₂alkyl, and —SO₂ substituted alkyl.

DETAILED DESCRIPTION OF THE INVENTION

A. Compounds of the Invention

Compounds of the invention include those of Formula (I) or a pharmaceutically acceptable salt, ester, or prodrug thereof:

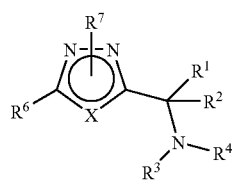

(I)

wherein:

R¹ is selected from the group consisting of alkyl and substituted alkyl;

R² is selected from the group consisting of hydrogen, alkyl, and substituted alkyl;

R³ is selected from the group consisting of -L¹-A¹, wherein L¹ is selected from the group consisting of —C(O)—, —C(S)—, —S(O)—, and —S(O)₂— and A¹ is selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, substituted heterocycloalkyl, and NR⁸R⁹;

R⁴ is selected from the group consisting of hydrogen, alkyl, substituted alkyl, alkenyl, substituted alkenyl, alkynyl, and substituted alkynyl;

or R³ and R⁴ together with the atoms bound respectively thereto join to form a five to seven membered heterocycloalkyl or substituted heterocycloalkyl group where optionally one additional ring atom (in addition to the nitrogen heteroatom to which R³ and R⁴ are attached) is selected from the group consisting of O, S, or NR¹¹;

X is CR⁵ or N;

R⁵ is selected from the group consisting of hydrogen, halo, alkyl, and substituted alkyl;

R⁶ is selected from the group consisting of cycloalkyl, heterocycloalkyl, aryl, and heteroaryl, all of which may be optionally substituted with —(R¹⁰)ₘ where R¹⁰ is as defined herein, m is 1, 2, 3, or 4, and each R¹⁰ may be the same or different when m is 2, 3, or 4;

R⁷ is -L²-A² wherein L² is C₁-C₅ alkylene and A² is selected from the group consisting of aryl, substituted aryl, heteroaryl, substituted heteroaryl, cycloalkyl, substituted cycloalkyl, heterocycloalkyl, and substituted heterocycloalkyl, provided that R⁷ is not attached to X;

R⁸ is selected from the group consisting of hydrogen and alkyl;

R⁹ is selected from the group consisting of hydrogen, hydroxy, alkyl, substituted alkyl, aryl, substituted aryl, heteroaryl, substituted heteroaryl, cycloalkyl, substituted cycloalkyl, heterocycloalkyl, and substituted heterocycloalkyl;

or R⁸ and R⁹ together with the nitrogen atom pendent thereto join to form a heterocycloalkyl or substituted heterocycloalkyl;

R¹⁰ is selected from the group consisting of cyano, alkyl, substituted alkyl, alkenyl, substituted alkenyl, alkynyl, substituted alkynyl, —CF₃, alkoxy, substituted alkoxy, halo, and hydroxy; and R¹¹ is selected from the group consisting of hydrogen, alkyl, substituted alkyl, —SO₂alkyl, and —SO₂ substituted alkyl.

In one embodiment, R² is alkyl. In one aspect, R² is methyl. In another aspect, R¹ and R² are methyl.

In one embodiment, provided is a compound having Formula (Ia)-(Ie) or a pharmaceutically acceptable salt, ester, or prodrug thereof:

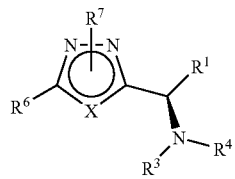

(Ia)

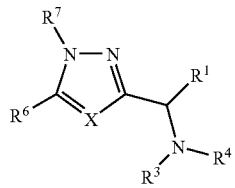

(Ib)

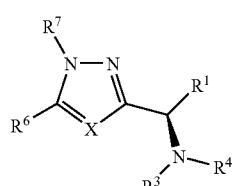

(Ic)

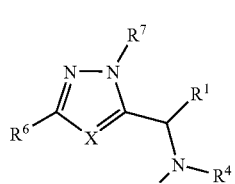

(Id)

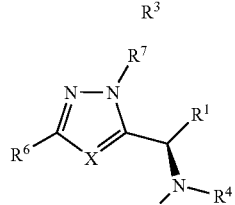

(Ie)

wherein R¹, R³, R⁴, X, R⁶, and R⁷ are as defined for Formula (I).

In some embodiments of the compounds of Formula (I) and (Ia)-(Ie), X is N.

In other embodiments of the compounds of Formula (I) and (Ia)-(Ie), X is CR$^5$. In some aspects, R$^5$ is hydrogen.

In one embodiment, compounds of the invention are represented by Formula (II) or a pharmaceutically acceptable salt, ester, or prodrug thereof:

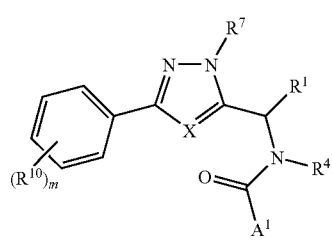

(II)

wherein:
R$^1$ is selected from the group consisting of alkyl and substituted alkyl;
R$^4$ is alkyl substituted with one to five substituents selected from the group consisting of hydroxy, alkoxy, substituted alkoxy, amino, substituted amino, acylamino, halo, nitrogen-containing heterocycloalkyl, substituted nitrogen-containing heterocycloalkyl, nitrogen-containing heteroaryl, and substituted nitrogen-containing heteroaryl;
A$^1$ is selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, substituted heterocycloalkyl, and NR$^8$R$^9$;
or A$^1$ and R$^4$ together with the atoms bound respectively thereto join to form a heterocycloalkyl or substituted heterocycloalkyl group where optionally one additional ring atom is selected from the group consisting of O, S, or NR$^{11}$; X is CR$^5$ or N;
R$^5$ is selected from the group consisting of hydrogen, halo, alkyl, and substituted alkyl;
R$^7$ is -L$^2$-A$^2$ wherein L$^2$ is C$_1$-C$_5$ alkylene and A$^2$ is selected from the group consisting of aryl, substituted aryl, heteroaryl, substituted heteroaryl, cycloalkyl, substituted cycloalkyl, heterocycloalkyl, and substituted heterocycloalkyl;
R$^8$ is selected from the group consisting of hydrogen and alkyl;
R$^9$ is selected from the group consisting of hydrogen, hydroxy, alkyl, substituted alkyl, aryl, substituted aryl, heteroaryl, substituted heteroaryl, cycloalkyl, substituted cycloalkyl, heterocycloalkyl, and substituted heterocycloalkyl;
or R$^8$ and R$^9$ together with the nitrogen atom pendent thereto join to form a heterocycloalkyl or substituted heterocycloalkyl;
m is 1, 2, 3, or 4, and each R$^{10}$ may be the same or different when m is 2, 3, or 4; and
R$^{10}$ is selected from the group consisting of cyano, alkyl, substituted alkyl, alkenyl, substituted alkenyl, alkynyl, substituted alkynyl, —CF$_3$, alkoxy, substituted alkoxy, halo, and hydroxy; and
R$^{11}$ is selected from the group consisting of hydrogen, alkyl, substituted alkyl, —SO$_2$alkyl, and —SO$_2$ substituted alkyl.

In some embodiments of the compounds of Formula (II), X is N.

In other embodiments, of the compounds of Formula (II), X is CR$^5$. In some aspects, R$^5$ is hydrogen.

In one embodiment, provided is a compound having Formula (IIa) or a pharmaceutically acceptable salt, ester, or prodrug thereof:

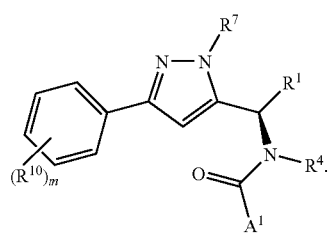

(IIa)

In one embodiment, provided is a compound having Formula (IIb) or a pharmaceutically acceptable salt, ester, or prodrug thereof:

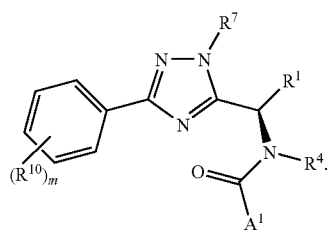

(IIb)

In one embodiment of the compounds of Formula (I), (Ia)-(Ie), (II), and (IIa)-(IIb), R$^1$ is alkyl. In another embodiment R$^1$ is selected from the group consisting of isopropyl, t-butyl, and propyl.

In one embodiment, L$^1$ is —CO—.
In one embodiment, A$^1$ is aryl or substituted aryl. In some aspects A$^1$ is substituted or unsubstituted phenyl.
In one embodiment, A$^1$ is heteroaryl or substituted heteroaryl. In some aspects, A$^1$ is substituted or unsubstituted pyridyl.
In one embodiment, A$^1$ is cycloalkyl or substituted cycloalkyl.
In one embodiment, A$^1$ is heterocycloalkyl or substituted heterocycloalkyl. In some aspects, A$^1$ is substituted or unsubstituted morpholino.
In one embodiment, A$^1$ is alkyl or substituted alkyl. In some aspects, A$^1$ is alkyl substituted with alkoxy or hydroxy.
In one embodiment, A$^1$ is 1,3-benzothiadiazol-4-yl, t-butoxy, butoxy, n-butoxy, cyclohexyl, 2,2-dimethylpropoxy, ethoxy, furan-3-yl, isoxazol-3-yl, methoxy, methyl, 2-methylpropoxy, phenyl, piperidin-3-yl, piperidin-4-yl, n-propoxy, pyridin-2-yl, pyridine-3-yl, pyridin-4-yl, pyrazin-2-yl, tetrahydrofuran-2-yl, tetrahydrofuran-3-yl, tetrahydro-2H-pyran-4-yl, 1H-tetrazol-1-yl, 2H-tetrazol-2-yl, thiazol-4-yl, 1,3,4-thiadiazol-2-yl, 1,3-benzothiadiazol-6-yl, 3,3-dihydrobenzo[1,2,3]thiadiazol-4-yl, benzimidazol-2-yl, benzimidazol-6-yl, benzo[1,2,5]thiadiazole, benzoxadiazol-4-yl, cyclopentyl, imidazol-4-yl, indazol-6-y, isooxazol-5-yl, morpholin-2-yl, morpholino, thiadiazol-4-yl, pyrrolidin-N-yl, pyrazol-3-yl, pyrrolidin-2-yl, pyrrolidin-3-yl, oxazol-4-yl, tetrazol-5-yl, or piperidin-N-yl.

In one embodiment, $A^1$ is a substituted aryl or heteroaryl group selected from the group consisting of 5-methyl-2H-imidazol-4-yl, 2-aminothiazol-4-yl, 4-t-butylphenyl, 2-chlorophenyl, 2-chloro-6-methylpyrid-4-yl, 3-chlorophenyl, 4-chlorophenyl, 6-chloropyridin-3-yl, 3,4-dichlorophenyl, 2,4-difluorophenyl, 1,5-dimethyl-1H-pyrazol-3-yl, 2,4-dimethylthiazol-5-yl, 1-ethyl-3-methyl-1H-pyrazol-5-yl, 2-methoxyphenyl, 4-methoxyphenyl, 4-methylisoxazol-3-yl, 5-methylisoxazol-4-yl, 4-methylphenyl, 1-methyl-3-trifluoromethyl-1H-pyrazol-4-yl, 1-methyl-5-chloro-1H-pyrazol-4-yl, 5-methyl-1H-pyrazol-3-yl, 6-methylpyridin-3-yl, 2-pyrrolidin-3-ylphenyl, 4-(trifluoromethyl)phenyl, 6-(trifluoromethyl)pyridin-3-yl, 2,5-dimethyloxazol-4-yl, 2-aminothiazol-4-yl, 4-methylpyrazol-5-yl, 3-trifluoromethylpyrazol-4-yl, 2-methyl-3-trifluoromethylpyrazol-5-yl, 4-chloro-1,3-dimethylpyrazolo[3,4]pyridine, and 1-methylbenzimidazol-2-yl.

In one embodiment, $A^1$ is a substituted heterocyclic or cycloalkyl selected from the group consisting of 3-[(aminoacetyl)amino]cyclohexyl, 1-methylpiperazin-4-yl, 3-(2-aminoethylsulfonylamino)cyclohexyl, 1-methylcarbonylpiperidin-4-yl, 1-methoxycarbonylpiperidin-4-yl, quinuclidin-3-yl, 2-oxopyrrolidin-5-yl, 2-oxopyrrolidin-4-yl, 2-oxodihydrofuran-5-yl, 2-oxothiazolidin-4-yl, and 3-hydroxypyrrolidin-5-yl.

In one embodiment, $A^1$ is 2-(hydroxymethyl)pyrrolidin-1-yl.

In one embodiment, $A^1$ is a substituted alkyl selected from the group consisting of 3-amino-2-oxo-1(2H)-pyridinylmethyl, cyanomethyl, (N,N-dimethylamino)methyl, ethoxymethyl, p-fluorophenoxymethyl, hydroxymethyl, 1H-imidazol-1-ylmethyl, methoxymethyl, (N-methylamino)methyl, methylsulfonylmethyl, (5-methyl-1H-tetrazol-1-yl)methyl, (5-methyl-2H-tetrazol-2-yl)methyl, morpholin-4-ylmethyl, 1H-pyrazol-1-ylmethyl, 1H-1,2,3-triazol-1-ylmethyl, 2H-1,2,3-triazol-2-ylmethyl, 1H-1,2,4-triazol-1-ylmethyl, 2H-1,2,4-triazol-2-ylmethyl, 4H-1,2,4-triazol-4-ylmethyl, 1H-tetrazol-1-ylmethyl, 1H-tetrazol-5-ylmethyl, 2H-tetrazol-2-ylmethyl, imidazol-4-ylmethyl, 1-methylpyrazol-3-ylmethyl, piperidin-4-ylmethyl, trifluoromethyl, dimethylaminoethyl, and 2-oxo-3-aminopyrrolidin-1-ylmethyl.

In one embodiment, $A^1$ is $NR^8R^9$.

In one embodiment, $R^8$ is hydrogen.

In one embodiment, $R^8$ and $R^9$ are hydrogen.

In one embodiment, $R^8$ and $R^9$ are alkyl. In some aspects, $R^8$ and $R^9$ are methyl.

In one embodiment $R^9$ is selected from the group consisting of alkyl, substituted alkyl, and cycloalkyl. In some aspects, $R^9$ is selected from the group consisting of methyl, hydroxymethyl, methoxymethyl, methoxyethyl, furan-2-ylmethyl, 2-hydroxyethyl, cyclopropyl and isopropyl.

In one embodiment, $R^9$ is aryl or substituted aryl. In some aspects, $R^9$ is selected from the group consisting of 4-cyanophenyl, 3,4-difluorophenyl, 2,3,5-trifluorophenyl, 3,5-dinitrophenyl, and phenyl.

In one embodiment, $R^9$ is heteroaryl or substituted heteroaryl. In some ways, $R^9$ is selected from the group consisting of thiophen-2-yl, 3,5-dimethylisoxazol-4-yl, and 2,6-dichloropyridin-4-yl.

In one embodiment, $R^9$ is a heterocycloalkyl or substituted heterocycloalkyl group. In some aspects, $R^9$ is tetrahydropyran-4-yl or 4-(ethoxycarbonyl)piperidin-4-yl.

In one embodiment, $R^9$ is a hydroxy.

In one embodiment, $R^8$ and $R^9$ are cyclized with the nitrogen atom bound thereto to form a heterocyclic or substituted heterocyclic. In some aspects, —$NR^8R^9$ are selected from the group consisting of thiamorpholin-N-yl, 1,1-dioxothiamorpholin-N-yl, 1-oxothiamorpholin-1-yl, 2-(aminomethylene)pyrrolidin-N-yl, 2-(methoxycarbonyl)pyrrolidin-N-yl, 2,6-dimethylmorpholin-N-yl, 3-hydroxypiperidin-N-yl, 3-hydroxypyrrolidin-N-yl, 4-(butylsulfonyl)piperazin-N-yl, 4-(cyclopropylsulfonyl)piperazin-N-yl, 4-(dimethylamino)piperidin-N-yl, 4-(ethoxycarbonyl)piperazin-N-yl, 4-(ethylsulfonyl)piperazin-N-yl, 4-(isopropylsulfonyl)piperazin-N-yl, 4-(methylcarbonyl)piperazin-N-yl, 4-(methylsulfonyl)piperidin-N-yl, 4-(methylsulfonyl)piperazin-N-yl, 4-(morpholin-N-yl)piperidin-N-yl, 4-(piperidin-N-yl)piperidin-N-yl, 4-(propylsulfonyl)piperazin-N-yl, 4-cyclohexylpiperazin-N-yl, 4-hydroxypiperidin-N-yl, 4-isopropylpiperazin-4-yl, 4-methylpiperidin-N-yl, isoxazolidin-2-yl, morpholin-N-yl, piperazin-N-yl, piperidin-N-yl, 2-(hydrazinocarbonyl)pyrrolidin-N-yl, and pyrrolidin-N-yl.

In some embodiments, $R^4$ is substituted alkyl. In some aspects, $R^4$ is alkyl substituted with 1 to 5 substituents selected from the group consisting of amino, substituted amino, halo, alkoxy, substituted alkoxy, and hydroxy.

In some embodiments, $R^4$ is selected from the group consisting of: hydrogen, piperidin-4-yl, —$(CH_2)_2$—$NH_2$, —$CH_2$-azetidin-3-yl, —$CH_2$-(2,5-dihydropyrrol-3-yl), —$(CH_2)_3$-imidazol-1-yl, —$CH_2$-(1H-imidazol-4-yl), —$CH_2$-pyridin-3-yl, —$CH_2$-(2-hydroxypyridin-4-yl), —$CH_2$-(6-hydroxypyridin-3-yl), —$CH_2$-morpholin-2-yl, —$CH_2$-pyrrolidin-3-yl, —$CH_2$-(3-fluoropyrrolidin-3-yl), —$CH_2$-(3-hydroxypyrrolidin-3-yl), —$CH_2$-(4-fluoropyrrolidin-3-yl), —$CH_2$-(4-hydroxypyrrolidin-3-yl), —$CH_2$—(2-hydroxymethylpyrrolidin-3-yl), —$CH_2$-piperidin-3-yl, —$CH_2$-[1H-(1,2,3-triazol-4-yl)], —$CH_2CH(NH_2)CH_2OH$, —$(CH_2)_3$—OH, —$(CH_2)_3$—O(CO)-phenyl, —$(CH_2)_3$—$NH_2$, —$(CH_2)_3$—$NHCH_3$, —$(CH_2)_3$—$N(CH_3)_2$, —$(CH_2)_3$—$NHOCH_3$, —$(CH_2)_3$—$NHSO_2CH_3$, —$(CH_2)_3NH$-(5-cyanopyridin-2-yl), —$(CH_2)_3NH$-cyclopropyl, —$(CH_2)_3NH$-cyclobutyl, —$(CH_2)_3$-(1H-imidazol-2-yl), —$(CH_2)_3$-(2-hydroxyethylpiperidin-1-yl), —$(CH_2)_3NH$(2-hydroxymethylphenyl), —$(CH_2)_3NH$-(5-trifluoromethylpyridin-2-yl), —$(CH_2)_3NHCH_2$-cyclopropyl, —$(CH_2)_3NHCH_2$-{5-(pyridin-3-yloxy)-1H-indazol-3-yl}, —$(CH_2)_3NHCH_2$-(5-methoxy-1H-indazol-3-yl), —$(CH_2)_3NHCH_2$-(6-fluoro-1H-indazol-3-yl), —$CH_2CHOHCH_2NH_2$, —$CH_2CH(CH_2OH)CH_2NH_2$, —$CH_2C(CH_3)_2CH_2$—$N(CH_3)_2$, —$CH_2C(CH_3)_2CH_2$-(4-methylpiperazin-1-yl), —$(CH_2)_2C(O)NH_2$, —$(CH_2)_2CH(NH_2)C(O)NH_2$, —$(CH_2)_2CH(NH_2)C(O)OH$, —$(CH_2)_2CH(NH_2)CH_2C(O)NH_2$, —$(CH_2)_2CH(NH_2)CH_2OH$, —$(CH_2)_2CH(NH_2)CH_3$, —$(CH_2)_3NHC(O)CH_2NH_2$, —$(CH_2)_3NHC(O)CH(NH_2)CH(CH_3)_2$, —$CH_2CHFCH_2NH_2$, —$(CH_2)_2NHC(O)CH_2NH_2$, —$(CH_2)_3$—$NHCH_2CH_2OH$, —$(CH_2)_3$—$NHCH_2CO_2H$, —$(CH_2)_3$—$NHCH_2CO_2CH_2CH_3$, —$(CH_2)_3$—$N(CH_2CH_2OH)_2$, —$(CH_2)_3$—$NHCH(CH_2OH)_2$, —$(CH_2)_3CH_3$, —$(CH_2)_2CH(NH_2)CH_2OH$, —$(CH_2)_2C(CH_3)_2NH_2$, —$(CH_2)_2CH(NH_2)CH_2OCH_3$, —$(CH_2)_2CH(NH_2)CH_2F$, —$CH_2CHFCH(NH_2)CH_2OH$, and —$(CH_2)_2$spirocylcopropyl-$NH_2$.

In one embodiment, $R^4$ is selected from the group consisting of —$(CH_2)_3NH_2$, —$(CH_2)_2CH(CH_2OH)NH_2$, —$CH_2CH(F)CH_2NH_2$, —$CH_2$-[2-($CH_2OH$)pyrrolidin-3-yl], —$CH_2$-[4-(OH)pyrrolidin-3-yl], —$CH_2$—C(F)(spiropyrrolidin-3-yl), —$(CH_2)_2CH(CH_2F)NH_2$, —$(CH_2)_2C(CH_3)_2NH_2$, —$(CH_2)_2CH(CH_3)NH_2$, and —$(CH_2)_2CH(CH_2OCH_3)NH_2$.

In some embodiments, $R^3$ and $R^4$ or $A^1$ and $R^4$ together with the atoms bound respectively thereto join to form a five to seven membered heterocycloalkyl or substituted heterocycloalkyl group. In some aspects, the substituted heterocycloalkyl is substituted with halo, alkyl, or with alkyl substituted with 1 to 5 substituents selected from the group consisting of amino, substituted amino, halo, alkoxy, substituted alkoxy, and hydroxy. In some aspects, the heterocycloalkyl or substituted heterocycloalkyl group is selected from the group consisting of:

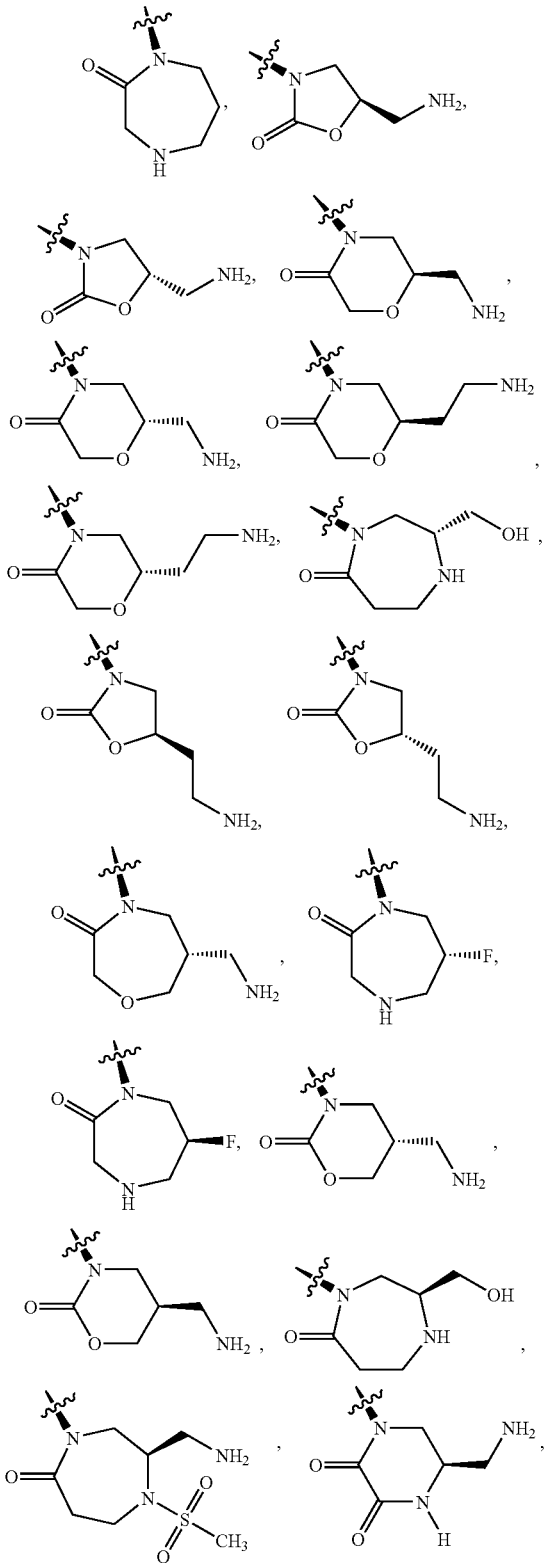

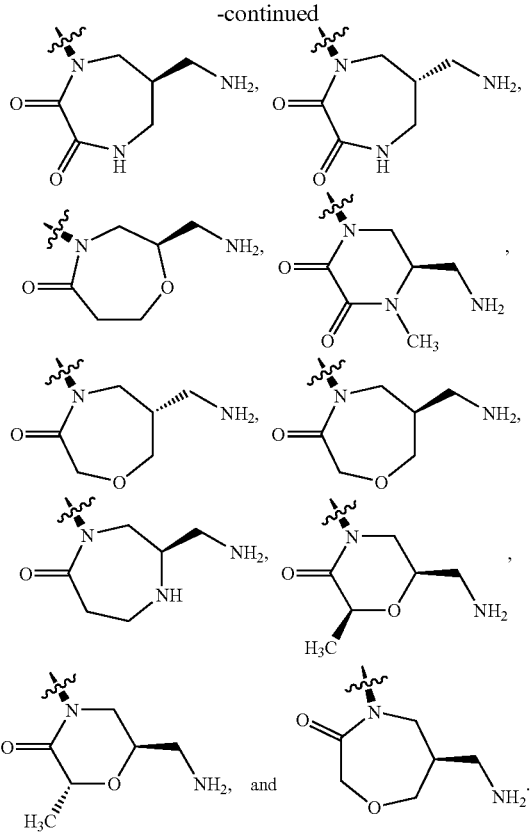

In one embodiment, $R^6$ is aryl or substituted aryl. In some embodiments, $R^6$ is selected from the group consisting of phenyl, 3-chlorophenyl, 3-fluorophenyl, 2,5-difluorophenyl, and 2,3,5-trifluorophenyl.

In one embodiment, $R^6$ is heteroaryl or substituted heteroaryl.

In one embodiment, $R^6$ is selected from the group consisting of phenyl, 3-bromophenyl, 2-fluoro-5-chlorophenyl, 2-chloro-5-fluorophenyl, 3,5-dichlorophenyl, 3-chlorophenyl, 4-cyanophenyl, 2,5-difluorophenyl, 3-fluorophenyl, 2-methoxyphenyl, 3-methoxyphenyl, 4-methoxyphenyl, 4-methylphenyl, pyrazin-2-yl, pyridin-2-yl, thiazol-2-yl, 2-trifluoromethylphenyl, and 3-trifluoromethylphenyl.

In one embodiment, $R^6$ is selected from the group consisting of 5-chloro-2-fluorophenyl, 2-fluoro-5-chlorophenyl, 3,5-difluorophenyl, and 3,5-dichlorophenyl.

In one embodiment, $A^2$ is selected from the group consisting of phenyl, 6-aminopyridin-2-yl, 3-chlorophenyl, 3-cyanophenyl, 2,4-difluorophenyl, 2,5-difluorophenyl, 3,5-difluorophenyl, 2-fluorophenyl, 3-fluorophenyl, 4-fluorophenyl, 3-hydroxyphenyl, 3-methoxyphenyl, 1-(5-methyl)-isoxazol-3-yl, 2-methylphenyl, 3-methylphenyl, 4-methylphenyl, pyridin-2-yl, pyridin-3-yl, pyridin-4-yl, tetrahydropyran-4-yl, thiazol-4-yl, and 5-trifluoromethylfuran-2-yl.

In one embodiment, $A^2$ is 3-bromophenyl, or 3-trifluoromethylphenyl.

In one embodiment, $L^2$ is methylene and $A^2$ is selected from the group consisting of phenyl, 3-fluorophenyl, or 3-hydroxyphenyl. In some aspects, $R^7$ is benzyl.

In one embodiment, $R^1$ is t-butyl, $L^2$ is methylene, $A^2$ is phenyl, and $R^6$ is phenyl or substituted phenyl.

In another embodiment $R^1$ is t-butyl, $L^2$ is methylene, $A^2$ is phenyl, $R^6$ is phenyl substituted with 1 to 2 halo substituents, such as chloro or fluoro.

In one embodiment $R^1$ is t-butyl, $R^2$ is hydrogen, $L^2$ is methylene, $A^2$ is phenyl, $R^4$ is substituted alkyl. In some such embodiment, $R^4$ is —$(CH_2)_3NH_2$, —$CH_2CH(F)CH_2NH_2$, —$(CH_2)_2CH(CH_2F)NH_2$, —$(CH_2)_2CH(CH_2OCH_3)NH_2$, —$(CH_2)_2CH(CH_3)NH_2$, —$(CH_2)_2C(CH_3)_2NH_2$ or —$(CH_2)_2CH(CH_2OH)NH_2$.

Representative Compounds of the Invention

Specific compounds within the scope of this invention are exemplified in Table 1 in the Experimental section.

Methods and Compositions of the Invention

Also provided is a composition comprising a compound of formulas (I), (Ia)-(Ie), (II), and (IIa)-(IIb) (including mixtures and/or salts thereof) and a pharmaceutically acceptable excipient or carrier.

In another aspect, the present invention provides methods of treating a mammalian patient suffering from a disorder mediated, at least in part, by KSP. Thus, the present invention provides methods of treating a mammalian patient in need of such treatment comprising administering to the patient a therapeutically effective amount of a compound of formulas (I), (Ia)-(Ie), (II), and (IIa)-(IIb) (including mixtures thereof) either alone or in combination with other anticancer agents.

B. Definitions and Overview

As discussed above, the present invention is directed in part to new substituted pyrazole and triazole compounds.

It is to be understood that the terminology used herein is for the purpose of describing particular embodiments only and is not intended to limit the scope of the present invention. It must be noted that as used herein and in the claims, the singular forms "a," and "the" include plural referents unless the context clearly dictates otherwise. In this specification and in the claims which follow, reference will be made to a number of terms which shall be defined to have the following meanings:

As used herein, "alkyl" refers to monovalent saturated aliphatic hydrocarbyl groups having from 1 to 6 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, spirocycloalkyl, heteroaryl, substituted heteroaryl, heterocyclic, substituted heterocyclic, —$SO_2$-alkyl, and —$SO_2$-substituted alkyl.

"Alkylene" refers to divalent saturated aliphatic hydrocarbyl groups preferably having from 1 to 5 and more preferably 1 to 3 carbon atoms which are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) or (—$CH(CH_3)CH_2$—) and the like.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxyacyl" or "carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, and substituted heterocyclic with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, and substituted heterocyclic with the proviso that any hydroxy substitution is not attached to an acetylenic carbon atom.

"Amino" refers to the group —NH$_2$.

"Cyano" refers to the group —CN.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —SO$_2$-alkyl, —SO$_2$-substituted alkyl, and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' or R" is hydrogen.

"Acylamino" refers to the groups —NRC(O)alkyl, —NRC(O) substituted alkyl, —NRC(O)cycloalkyl, —NRC(O) substituted cycloalkyl, —NRC(O)alkenyl, —NRC(O) substituted alkenyl, —NRC(O)alkynyl, —NRC(O) substituted alkynyl, —NRC(O)aryl, —NRC(O) substituted aryl, —NRC(O)heteroaryl, —NRC(O) substituted heteroaryl, —NRC(O) heterocyclic, and —NRC(O) substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Nitro" refers to the group —NO$_2$.

"Aryl" or "Ar" refers to a monovalent aromatic carbocyclic group of from 6 to 14 carbon atoms having a single ring (e.g., phenyl) or multiple condensed rings (e.g., naphthyl or anthryl) in which the condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl ester, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl (NH$_2$—SO$_2$—), and substituted amino sulfonyl.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Spirocycloalkyl" refers to cyclic groups from 3 to 10 carbon atoms having a cycloalkyl ring with a spiro union (the union formed by a single atom which is the only common member of the rings) as exemplified by the following structure:

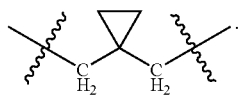

"Substituted cycloalkyl" refers to a cycloalkyl group, having from 1 to 5 substituents selected from the group consisting of alkyl, substituted alkyl, oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, substituted heterocyclic, —SO$_2$-alkyl and —SO$_2$-cycloalkyl "Halo" or "halogen" refers to fluoro, chloro, bromo and iodo and preferably is fluoro or chloro.

"Hydroxy" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 3 substituents selected from the same group of substituents defined for substituted aryl.

"Nitrogen-containing heteroaryl" and "nitrogen-containing substituted heteroaryl" refers to heteroaryl groups and substituted heteroaryl groups comprising at least one nitrogen ring atom and optionally comprising other non-nitrogen hetero ring atoms such as sulfur, oxygen and the like.

"Heteroaryloxy" refers to the group —O-heteroaryl and "substituted heteroaryloxy" refers to the group —O-substituted heteroaryl wherein heteroaryl and substituted heteroaryl are as defined herein.

"Heterocycle" or "heterocyclic" or "heterocycloalkyl" or "heterocyclyl" refers to a saturated or unsaturated (but not aromatic) group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more of the rings can be cycloalkyl, aryl or heteroaryl provided that the point of attachment is through the heterocyclic ring. In one embodiment, the nitrogen and/or sulfur atom(s) of the heterocyclic group are optionally oxidized to provide for the N-oxide, sulfinyl, and sulfonyl moieties.

"Substituted heterocyclic" or "substituted heterocycloalkyl" or "substituted heterocyclyl" refers to heterocyclyl groups that are substituted with from 1 to 3 of the same substituents as defined for substituted cycloalkyl.

Examples of heterocyclyls and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitrogen-containing heterocyclic" and "nitrogen-containing substituted heterocyclic" refers to heterocyclic groups and substituted heterocyclic groups comprising at least one nitrogen ring atom and optionally comprising other non-nitrogen hetero ring ring atoms such as sulfur, oxygen and the like.

"Thiol" refers to the group —SH.

"Alkylthio" or "thioalkoxy" refers to the group —S-alkyl.

"Substituted alkylthio" or "substituted thioalkoxy" refers to the group —S-substituted alkyl.

"Arylthio" refers to the group —S-aryl, where aryl is defined above.

"Substituted arylthio" refers to the group —S-substituted aryl, where substituted aryl is defined above.

"Heteroarylthio" refers to the group —S-heteroaryl, where heteroaryl is defined above.

"Substituted heteroarylthio" refers to the group —S-substituted heteroaryl, where substituted heteroaryl is defined above.

"Heterocyclicthio" refers to the group —S-heterocyclic and "substituted heterocyclicthio" refers to the group —S-substituted heterocyclic, where heterocyclic and substituted heterocyclic are defined above.

"Heterocyclyloxy" refers to the group heterocyclyl-O— and "substituted heterocyclyloxy refers to the group substituted heterocyclyl-O— where heterocyclyl and substituted heterocyclyl are defined above.

"Cycloalkylthio" refers to the group —S-cycloalkyl and "substituted cycloalkylthio" refers to the group —S-substituted cycloalkyl, where cycloalkyl and substituted cycloalkyl are defined above.

"Biological activity" as used herein refers to an inhibition concentration when tested in at least one of the assays outlined in any of Examples 12-14 and as defined in at least one example thereof.

As used herein, the term "pharmaceutically acceptable salts" refers to the nontoxic acid or alkaline earth metal salts of the compounds of Formula (I), (Ia)-(Ie), (II), and (IIa)-(IIb). These salts can be prepared in situ during the final isolation and purification of the compounds of Formula (I), (Ia)-(Ie), (II), and (IIa)-(IIb), or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of Formula (I), (Ia)-(Ie), (II), and (IIa)-(IIb), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters which hydrolyze in vivo and include those that break down in the human body to leave the parent compound, a salt thereof, or a pharmaceutically active metabolite. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound or a pharmaceutically active metabolite of the above formula, for example by hydrolysis in blood. A discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein "anticancer agents" or "agent for the treatment of cancer" refers to agents that include, by way of example only, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons and interleukins, etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other agents are well within the purview of one of skill in the art.

It is understood that in all substituted groups defined above, polymers arrived at by defining substituents with further substituents to themselves are not intended for inclusion herein. In such cases, the maximum number of such substituents is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxy group alpha to ethenylic or acetylenic unsaturation). Such impermissible substitution patterns are well known to the skilled artisan.

Compounds of this invention may exhibit stereoisomerism by virtue of the presence of one or more asymmetric or chiral centers in the compounds. The present invention contemplates the various stereoisomers and mixtures thereof. Depiction of the compounds of Formula (I), (Ia)-(Ie), (II), and (IIa)-(IIb) includes the stereoisomers thereof unless the stereochemistry of a particular stereocenter is indicated otherwise. Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, single enantiomer, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," *Pure Appl. Chem.* 45:13-30, 1976. Desired enantiomers can be obtained by chiral synthesis from commercially available chiral starting materials by methods well known in the art, or may be obtained from mixtures of the enantiomers by separating the desired enantiomer by using known techniques.

Compounds of this invention may also exhibit geometrical isomerism. Geometrical isomers include the cis and trans forms of compounds of the invention having alkenyl or alkenylenyl moieties. The present invention comprises the individual geometrical isomers and stereoisomers and mixtures thereof.

C. Compound Preparation

The compounds of this invention can be prepared from readily available starting materials using the following general methods and procedures. Unless otherwise indicated, the starting materials are commercially available and well known in the art. It will be appreciated that where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

In one embodiment, provided is a method for preparing a compound of Formula (I) where X is N:

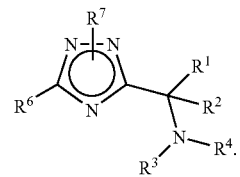

This method comprises:

a) reacting a compound of Formula (III) with a compound of Formula (IV) under acylation conditions to form a compound of Formula (V) where $R^1$, $R^2$, and $R^6$ are previously defined and PG is a nitrogen protecting group

(III)

(IV)

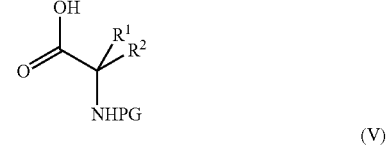

(V)

b) heating a compound of Formula (V) to form a compound of Formula (VI)

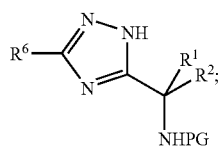
(VI)

c) reacting a compound of Formula (VI) with $R^7$—$X^7$ to form a compound of Formula (VIIa) or (VIIb), where $R^7$ is previously defined and $X^7$ is a leaving group

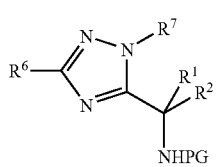
(VIIa)

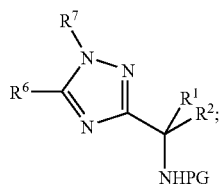
(VIIb)

d) exposing a compound of Formula (VIIa) or (VIIb) to deprotection conditions to remove the protecting group PG to form (VIIIa) or (VIIIb)

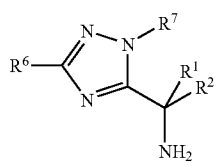
(VIIIa)

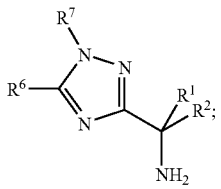
(VIIIb)

e) reacting a compound of Formula (VIIIa) or (VIIIb) with $R^4$—$X^4$ under coupling conditions or with $R^{4a}$CHO under reductive amination conditions wherein $R^4$ is previously defined and $R^{4a}CH_2$— is $R^4$ and $X^4$ is a leaving group to form a compound of Formula (IXa) or (IXb)

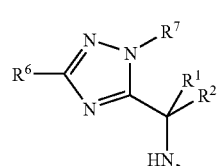
(IXa)

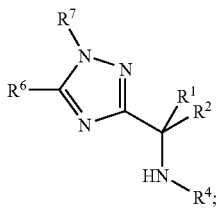
(IXb)

f) reacting a compound of Formula (IXa) or (IXb) with $R^3$—$X^3$ under coupling conditions wherein $R^3$ is previously defined and $X^3$ is a leaving group to form a compound of Formula (I) where X is N

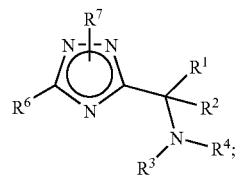

g) optionally converting a compound of Formula (IXa) or (IXb) to a compound of Formula (Xa) or (Xb) where W is —C(Y)—$X^3$ where $X^3$ is a leaving group and Y is =O or =S, and reacting the compound where W is —C(Y)—$X^3$ with HN$R^8R^9$ to form a compound of Formula (I) where $R^3$ is —C(Y)N$R^8R^9$

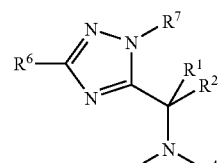
(Xa)

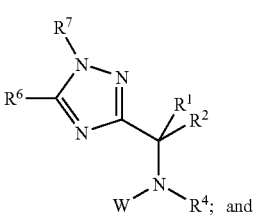
(Xb)

h) optionally converting a compound of Formula (I) where X is N to an ester, prodrug, or a pharmaceutically acceptable salt thereof.

In one embodiment, the compound of Formula (III) is prepared by reacting nitrile (XI) where $R^6$ is previously defined with a sulfide and an organic base to form thioamide (XII).

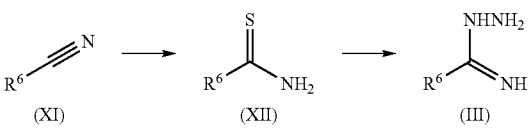

Suitable sulfides include $(NH_4)_2S$ and suitable amines include triethylamine and/or pyridine. Thioamide (XII) is then reacted with one to two equivalents of hydrazine in a polar solvent such as ethanol to give (III). An example of this process where $R^6$ is 2,5-difluorobenzonitrile is shown in Step A of Example 1.

In another embodiment provided is a method for preparing a compound of Formula (V) by reacting (III) with (IV) under acylation conditions.

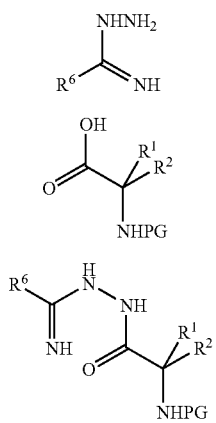

Such conditions include converting (IV) to a mixed anhydride such as by reaction or (IV) with an alkylchlorofomate such as ethylchloroformate and treating the resulting anhydride with hydrazide (III) to form (V). In some aspects, the amine protecting group is t-butoxycarbonyloxy (Boc). An example of this process for forming (V) where $R^6$ is 2,5-difluorobenzonitrile, PG is Boc, $R^1$ is t-butyl, and $R^2$ is hydrogen is shown in Step B of Example 1.

In one embodiment provided is a method for preparing a compound of Formula (VI) by heating (V) in a solvent having a boiling point of greater than 100° C. such as xylene.

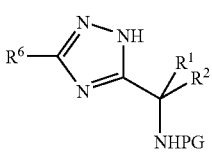

Typically, (V) is heated in xylenes to about 150° C. and a Dean Stark trap is employed to remove the lower boiling water side-product.

In one embodiment, provided is a method for preparing a compound of Formula (VIIa) or (VIIb). A compound of Formula (VI) is reacted with $R^7$—$X^7$ where $R^7$ is previously defined and $X^7$ is a leaving group. In some aspects, $R^7$ is benzyl. In other aspects, $X^7$ is a halogen. In still other aspects $R^7$—$X^7$ is benzyl bromide. The reaction can be carried out under alkylation conditions. Such conditions include use of a polar solvent such as dimethylformamide and a base such as $Cs_2CO_3$. The reaction may lead to a mixture of (VIIa) and (VIIb) and each may be isolated individually by chromatography at this stage or at a later stage when these compounds are employed as starting materials. An example of the formation of (VIIa) and (VIIb) when $R^7$ is benzyl is shown in Step E of Example 1

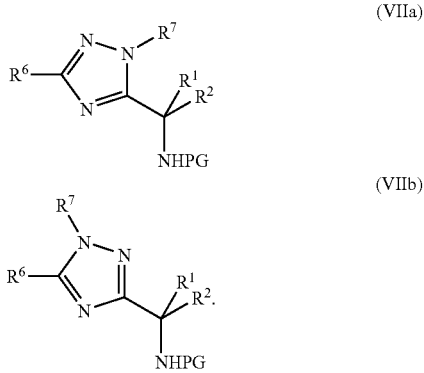

In one embodiment provided is an intermediate compound of Formula (VIIIa) or (VIIIb) where $R^1$, $R^2$, $R^6$, and $R^7$ are as defined for Formula (I):

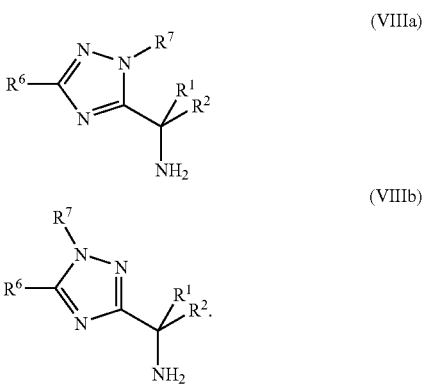

In another embodiment, provided is a method of preparing an intermediate compound of Formula (VIIIa) or (VIIIb) by exposing a compound of Formula (VIIa) or (VIIb) to deprotection conditions. In one aspect when PG is Boc, the protecting group is removed by exposure to acidic conditions such treatment with trifluoroacetic acid. An example of this deprotection is shown in Step F of Example 1.

In another embodiment, provided is a method for preparing an intermediate compound of Formula (IXa) or (IXb):

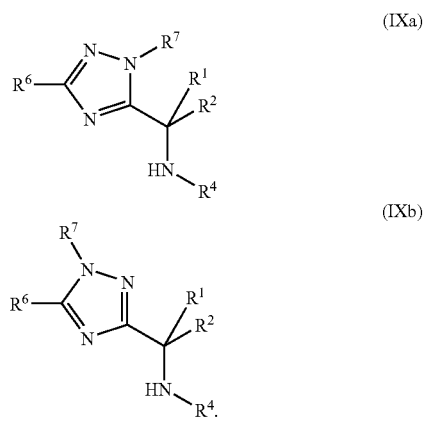

A compound of Formula (VIIIa) or (VIIIb) is reacted with $R^4$—$X^4$ where $X^4$ is a leaving group such as a halogen atom, or with R⁴ᵃCHO under reductive animation conditions wherein R⁴ and R⁴ᵃ are previously defined to form a compound of Formula (IXa) or (IXb). Suitable reductive animation conditions include treatment of a solution containing (VIIIa) and (VIIIb) with a weak acid to effect imine formation followed by addition of a reducing agent. In some aspects the acid is an organic acid such as camphrosulfonic acid or a mineral acid such as acetic acid, and the reducing agent is a borohydride such as triacetoxyborohydride.

In another embodiment, provided is a method for preparing a compound of Formula (I) where X is N

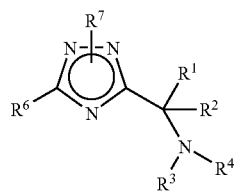

by reacting a compound of Formula (IXa) or (IXb) under suitable coupling conditions with R³—X³ wherein R³ is previously defined and X³ is a leaving group such as a halogen atom. In some aspects R³—X³ is an acyl halide and the reaction is preformed in the presence of an organic base such as triethylamine.

Compounds of Formula (I) where X is N may optionally be prepared by converting a compound of Formula (IXa) or (IXb) to a compound of Formula (Xa) or (Xb) where W is —C(Y)—X³ where X³ is a leaving group and Y is =O or =S. In one example, (IXa) or (IXb) is reacted with triphosgene to form (Xa) or (Xb) where W is —C(O)—Cl. The resulting intermediate is then reacted with HNR⁸R⁹ to form the urea compound of Formula (I) where R³ is —C(O)NR⁸R⁹.

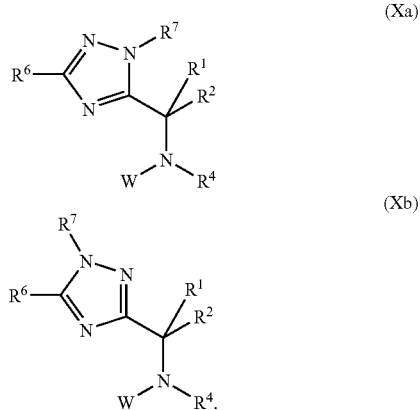

Additional modifications to (Xa) and (Xb) to form compounds of the Formula (I) where W and R⁴ join together to form a heterocycloalkyl or substituted heterocycloalkyl ring will be apparent to one of skill in the art. An example of such modifications is shown in Example 5.

In another embodiment, provided is a method for preparing a compound of Formula (I) where X is CR⁵ as shown in Scheme 1, where R¹, R², R⁵, R⁶, and R⁷ are previously defined and PG is a nitrogen protecting group.

Scheme 1

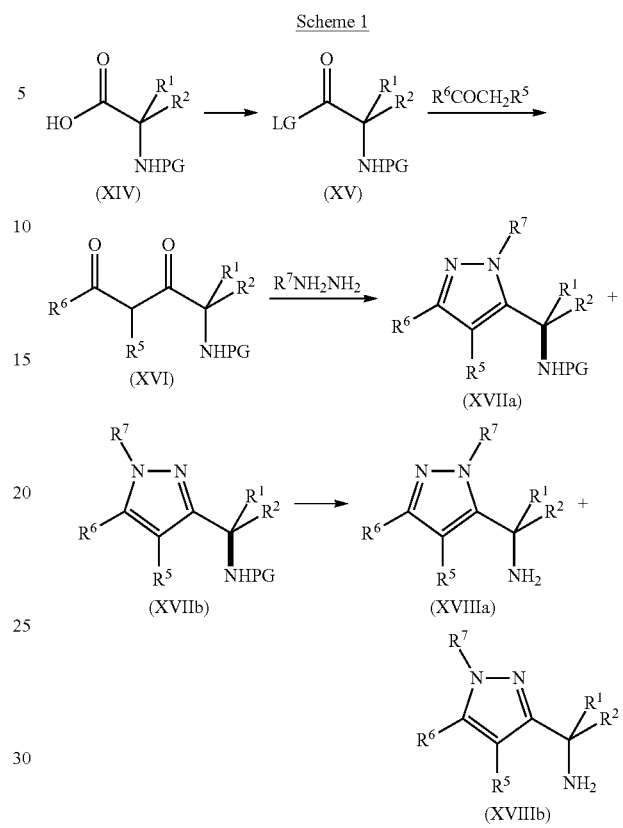

Acid (XIV) is converted to (XV) where LG is a suitable leaving group such as halo or imidazole, the latter of which can be prepared, for example, by reaction of (XIV) with a coupling reagent such as carbonyldiimidazole. Treatment of ketone R⁶COCH₂R⁵ with an organic base such as lithium hexamethydisilazide to form the corresponding enolate followed by reaction with (XV) gives the beta-keto compound (XVI). Compound (XVI) is then treated with azide R⁷NH₂NH₂ to form pyrazoles (XVII) and (XVIIb). Alternatively, (XVI) is treated with hydrazine to form the pyrazoles where the nitrogen atom is unsubstituted, followed by alkylation with a suitable R⁷ compound to form (XVII) and (XVIIb) as described above for the synthesis of compounds (VIIa) and (VIIb). Deprotection of (XVIIa) and (XVIIb) gives the corresponding amines (XVIIIa) and (XVIIIb). Intermediate compounds (XVIIIa) and (XVIIIb) may be further functionalized according to the procedures described above and in the examples for compounds of Formula (VIIIa) or (VIIIb).

In one embodiment, provided is an intermediate compound of Formula (XVIIIa) and (XVIIIb) where R¹, R², R⁵, R⁶, and R⁷ are as defined for Formula (I):

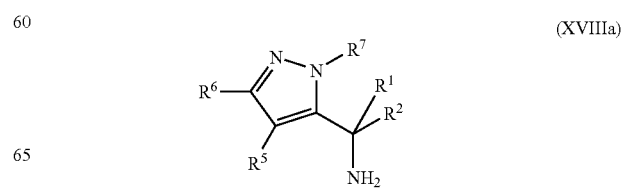

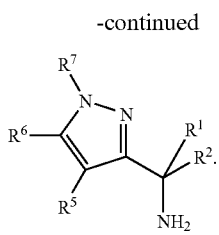
(XVIIIb)

In another embodiment, provided is a method for preparing a free base of a compound of Formula (I), (Ia)-(Ie), (II), or (IIa)-(IIb) comprising reacting an acid addition salt of the compound with a base to form the corresponding free base.

In another embodiment, provided is a method for preparing a salt of a compound of Formula (I), (Ia)-(Ie), (II), or (IIa)-(IIb) comprising:

a) reacting a free base of a compound of Formula (I), (Ia)-(Ie), (II), or (IIa)-(IIb) with an acid to give an acid addition salt; or b) converting a salt of a compound of Formula (I), (Ia)-(Ie), (II), or (IIa)-(IIb) to another salt of a compound of Formula (I), (Ia)-(Ie), (II), or (IIa)-(IIb).

D. Pharmaceutical Formulations

When employed as pharmaceuticals, the compounds of the subject invention are usually administered in the form of pharmaceutical compositions. These compositions can be administered by a variety of routes including oral, parenteral, transdermal, topical, rectal, and intranasal. These compounds are effective, for example, as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 1 to about 500 mg, usually about 5 to about 100 mg, occasionally about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the condition being treated, the chosen route of administration, the actual compound administered, the age, weight, and response of the individual patient, the severity of the patient's symptoms, and the like.

In therapeutic use for treating, or combating, cancer in mammals, the compounds or pharmaceutical compositions thereof will be administered by any appropriate route, such as orally, topically, transdermally, and/or parenterally at a dosage to obtain and maintain a concentration, that is, an amount, or blood-level of active component in the mammal undergoing treatment that will be therapeutically effective. Generally, such therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%)/ Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
| --- | --- |
| Active Ingredient | 5.0 mg |
| Corn Oil | 1.0 mL |

Formulation Example 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

An intravenous formulation may be prepared as follows:

| Ingredient | Quantity |
| --- | --- |
| Active Ingredient | 250 mg |
| Isotonic saline | 1000 mL |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mack Publishing Company, Philadelphia, Pa., 17th ed. (1985).

E. Dosage and Administration

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Compounds of the instant invention are useful for inhibiting or treating a disorder mediated, at least in part, by the activity of KSP. In one aspect, the disorder that is mediated, at least in part by KSP, is a cellular proliferative disorder. The term "cellular proliferative disorder" or "cell proliferative disorder" refers to diseases including, for example, cancer, tumor, hyperplasia, restenosis, cardiac hypertrophy, immune disorder and inflammation. The present invention provides methods of treating a human or mammalian subject in need of such treatment, comprising administering to the subject a therapeutically effective amount of a compound of formula I or II, either alone or in combination with other anticancer agents.

The compounds of the invention are useful in vitro or in vivo in inhibiting the growth of cancer cells. The term "cancer" refers to cancer diseases including, for example, lung and bronchus; prostate; breast; pancreas; colon and rectum; thyroid; stomach; liver and intrahepatic bile duct; kidney and renal pelvis; urinary bladder, uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

Cancer also includes tumors or neoplasms selected from the group consisting of carcinomas, adenocarcinomas, sarcomas, and hematological malignancies.

Additionally, the type of cancer can be selected from the group consisting of growth of solid tumors/malignancies, myxoid and round cell carcinoma, locally advanced tumors, human soft tissue carcinoma, cancer metastases, squamous cell carcinoma, esophageal squamous cell carcinoma, oral carcinoma, cutaneous T cell lymphoma, Hodgkin's lymphoma, non-Hodgkin's lymphoma, cancer of the adrenal cortex, ACTH-producing tumors, nonsmall cell cancers, breast cancer, gastrointestinal cancers, urological cancers, malignancies of the female genital tract, malignancies of the male genital tract, kidney cancer, brain cancer, bone cancers, skin cancers, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

A compound or composition of this invention may be administered to a mammal by a suitable route, such as orally, intravenously, parenterally, transdermally, topically, rectally, or intranasally.

Mammals include, for example, humans and other primates, pet or companion animals, such as dogs and cats, laboratory animals, such as rats, mice and rabbits, and farm animals, such as horses, pigs, sheep, and cattle.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and organization relative to one another and to surrounding tissues. This property is called "anaplasia."

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the compounds during incubation with peptidases or human plasma or serum.

For diagnostic purposes, a wide variety of labels may be linked to the compounds, which may provide, directly or indirectly, a detectable signal. Thus, the compounds and/or compositions of the subject invention may be modified in a variety of ways for a variety of end purposes while still retaining biological activity. In addition, various reactive sites may be introduced for linking to particles, solid substrates, macromolecules, and the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the progression or symptoms of the disease and its complications. An amount adequate to accomplish this is defined as "therapeutically effective dose." Amounts effective for this use will depend on the disease condition being treated as well as by the judgment of the attending clinician depending upon factors such as the severity of the disease, disorder or condition, the age, weight and general condition of the patient, and the like.

The compounds administered to a patient are typically in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between about 3 and 11, more preferably from about 5 to 9 and most preferably from about 7 to 8. It will be understood that use of certain of the foregoing excipients, carriers, or stabilizers will result in the formation of pharmaceutical salts.

The therapeutic dosage of the compounds and/or compositions of the present invention will vary according to, for example, the particular use for which the treatment is made, the manner of administration of the compound, the health and condition of the patient, and the judgment of the prescribing physician. For example, for oral administration, the dose will typically be in the range of about 5 μg to about 50 mg per kilogram body weight per day, preferably about 1 mg to about 10 mg per kilogram body weight per day. In the alternative, for intravenous administration, the dose will typically be in the range of about 5 μg to about 50 mg per kilogram body weight, preferably about 500 μg to about 5000 μg per kilogram body weight. Alternative routes of administration contemplated include, but are not limited to, intranasal, transdermal, inhaled, subcutaneous and intramuscular. Effective doses can be extrapolated from dose-response curves derived from in vitro or animal model test systems.

In general, the compounds and/or compositions of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound and/or composition used in the method of the invention, the therapeutically effective dose can be estimated initially from cell culture assays. A dose may be formulated in animal models to achieve a circulating plasma concentration range which includes the $IC_{50}$ (the concentration of the test compound which achieves a half-maximal inhibition of activity) as determined in cell culture. Such information can be used to more accurately determine useful doses in humans. Levels in plasma may be measured, for example, by high performance liquid chromatography.

The following synthetic and biological examples are offered to illustrate this invention and are not to be construed in any way as limiting the scope of this invention.

EXAMPLES

Referring to the examples that follow, compounds of the present invention were synthesized using the methods described herein, or other methods, which are well known in the art. It is understood that compounds not prepared or analyzed may be prepared or analyzed using the methods described herein, or other methods, which are well known in the art.

The compounds and/or intermediates were characterized by high performance liquid chromatography (HPLC) using a Waters Millennium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LC/MS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses were reported as those of the protonated parent ions.

GC/MS analysis is performed on a Hewlett Packard instrument (HP6890 Series gas chromatograph with a Mass Selective Detector 5973; injector volume: 1 mL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.).

Melting points are determined on a Laboratory Devices Mel-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, EtOAc, hexane, acetone, aqueous hydroxyamine and triethyl amine. Typical solvents employed for the reverse phase HPLC were varying concentrations of acetonitrile and water with 0.1% trifluoroacetic acid.

Unless otherwise stated all temperatures are in degrees Celsius. Also, in these examples and elsewhere, abbreviations have the following meanings:

| | |
|---|---|
| AcOH = | acetic acid |
| aq. = | aqueous |
| ATP = | adenosine triphosphate |
| Boc = | tert-butyloxycarbonyl |
| BSA = | bovine serum albumin |
| CAM = | ceric ammonium molybdate |
| DCM = | dichloromethane |
| DIAD = | diisopropyl azodicarboxylate |
| DIBAL = | diisobutylaluminum hydride |
| DIEA = | diisopropylethylamine |
| DIPEA = | diisopropylethylamine |
| DMAP = | dimethylaminopyridine |
| DMF = | dimethylformamide |
| DMSO = | dimethylsulfoxide |
| DTT = | dithiothreitol |
| eq. = | equivalents |
| $Et_2O$ = | diethyl ether |
| $Et_3N$ = | triethyl amine |
| EtOAc = | ethyl acetate |
| EtOH = | ethanol |
| g = | gram |
| h = | hour |
| HPLC = | high performance liquid chromatography |
| L = | liter |
| LC/MS = | liquid chromatography/mass spectroscopy |
| M = | molar |
| m = | meter |
| m/z = | mass/charge ratio |
| $MeNH_2$ = | methyl amine |
| mg = | milligram |
| min = | minute |
| mL = | milliliter |
| mm = | millimeter |
| mM = | millimolar |
| mmol = | millimole |
| mol = | mole |
| N = | normal |
| nm = | nanometer |
| nM = | nanomolar |
| NMR = | nuclear magnetic resonance |
| $PPh_3$ = | triphenyl phosphine |
| $PhCF_3$ = | trifluoromethylbenzene |

| | |
|---|---|
| psi = | pounds per square inch |
| RT = | room temperature |
| sat. = | saturated |
| TEA = | triethylamine |
| THF = | tetrahydrofuran |
| TFA = | trifluoroacetic acid |
| TLC = | thin layer chromatography |
| TMS = | trimethylsilyl |
| TMSCl = | trimethylsilyl chloride |
| μg = | microgram |
| μL = | microliter |
| μM = | micromolar |

Example 1

N—((S)-3-amino-4-fluorobutyl)-N—((R)-1-(1-benzyl-3-(2,5-difluorophenyl)-1H-1,2,4-triazol-5-yl)-2,2-dimethylpropyl)nicotinamide

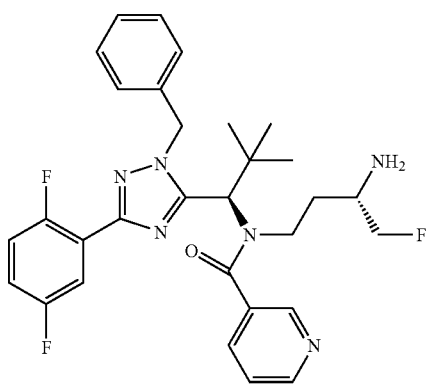

Step A: Thio-Amide Synthesis

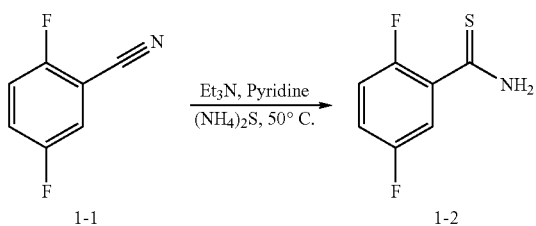

A stirred solution of the appropriate benzonitrile e.g., 2,5-difluorobenzonitrile (1-1), (15 mmol) in pyridine (10 mL) was treated with sulfide (20% wt solution in water, 16.5 mmol) and triethyl amine (16.5 mmol). The reaction mixture was stirred at 50° C. for 5 hr until the reaction was complete. After cooling to RT, the mixture was diluted with cold water. Extracted with EtOAc, and the organics separated, then washed with H$_2$O (×3), sat. brine (×3), then dried (Na$_2$SO$_4$), filtered, and evaporated under reduced pressure to give the crude. Purification on silica gel column (20% ethyl acetate/hexane) to afford thio-amide as yellow solid, 1-2 (yield 88.5%). $^1$H NMR (300 MHz, CDCl$_3$): δ 7.12 (m, 2H), 7.90 (br, 2 H), 8.08 (m, 1H).

Step B: Hydrazide Formation

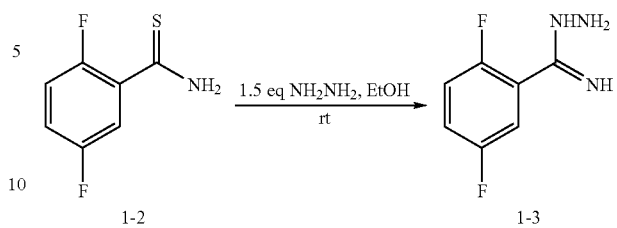

To a stirred solution of thio-amide 1-2, (5.0 mmol) in EtOH (5 mL) was added hydrazine (7.5 mmol). After stirring at RT for 30 min, reaction was complete by LC-MS and white solid precipitated. The precipitate was filtered and washed with Hexane to afford hydrazide 1-3 (yield 94%).

Step C: Acylation of Hydrazide

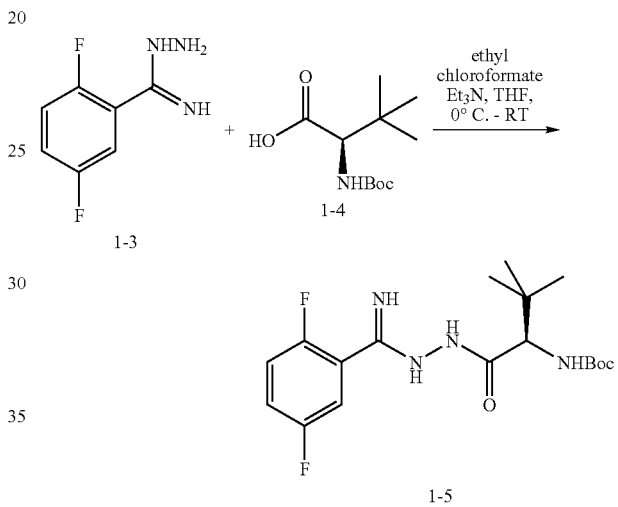

The N-Boc-D-tert-butylglycine 1-3 (2 mmol) was converted to a mixed anhydride by adding ethyl chloroformate (2.4 mmol), Et$_3$N (3 mmol) in dry THF at −5° C. to 0° C. The mixture was stirred at −5° C. for 30 min. The resulting solid was filtered off. Add additional dry THF to wash the precipitate. The resulting reaction solution was added to a THF solution of hydrazide (1-3, 2 mmol) at −5° C. Then the reaction was stirred and gradually warmed to RT overnight. Once the reaction was complete, the mixture was partitioned between EtOAc and H$_2$O. The organic layer was separated and washed with H$_2$O (×3), sat. brine (×3), then dried (Na$_2$SO$_4$), filtered, and evaporated under reduced pressure to give the crude product, which was purified on silica gel column (Hexane/Ethyl acetate) to afford 1-5. (Yield 67%)

Step D: Phenyl-Triazole Formation

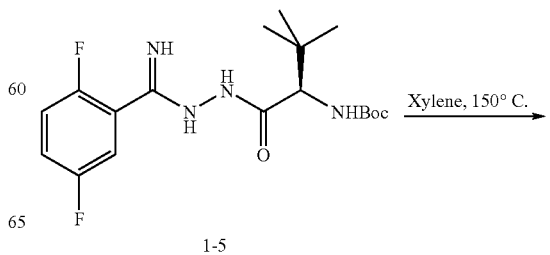

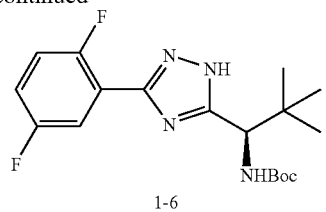

Compound 1-5 (2.86 mmol) was dissolved in xylenes (5.7 mL). A Dean-Stark trap was added and the reaction heated to 150° C. Once the reaction was complete, the mixture was allowed to cool to RT, then partitioned between EtOAc and sat. aq. NaHCO$_3$. The organics were separated, then washed with sat. aq. NaHCO$_3$ (×2), H$_2$O (×3), sat. brine (×3), then dried (Na$_2$SO$_4$), filtered, and evaporated under reduced pressure to give the phenyl triazole 6, which was pure enough to use directly in the next step.

Step E: Benzylation of the Phenyl Triazole

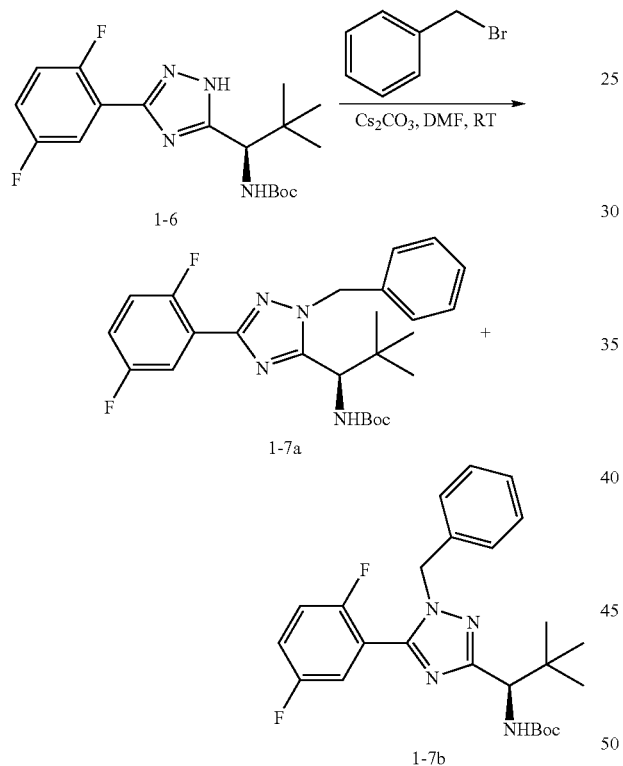

To a stirred solution/suspension of triazole (2.0 mmol) and Cs$_2$CO$_3$ (4.0 mmol) in DMF (5 mL) was added the benzylating agent, e.g., benzyl bromide (2.2 mmol). Once the reaction was complete, the mixture was partitioned between EtOAc and H$_2$O. The organic layer was separated and washed with H$_2$O (×3), sat. brine (×3), then dried (Na$_2$SO$_4$), filtered, and evaporated under reduced pressure to give the crude benzylated phenyl triazole mixtures. The region-isomers 1-7a and 1-7b were separated on silica gel column (Hexane/Ethyl acetate). The regiochemical outcome was verified by 1H NMR nOe experiments.

1-7a: crystals, MS (m/z): 457.3 [MH$^+$], rt=4.00 min; $^1$H NMR (300 MHz, CDCl$_3$): δ 7.78 (m, 1H), 7.29-7.39 (m, 5H), 7.00-7.18 (m, 2H), 5.53 (s, 2H), 5.20 (d, 2H), 4.83 (d, 2H, J=9.9 Hz), 1.41 (s, 9H), 0.91 (s, 9H).

1-7b: colorless oil, MS (m/z): 457.3 [MH$^+$], rt=3.66 min; $^1$H NMR (300 MHz, CDCl$_3$): δ 7.25 (m, 5H), 7.15 (m, 2H), 7.05 (m, 1H), 5.45 (d, 2H), 5.28 (s, 2H), 4.85 (d, 2H), 1.43 (s, 9H), 0.97 (s, 9H).

Step F: Deprotection to the Free Amine

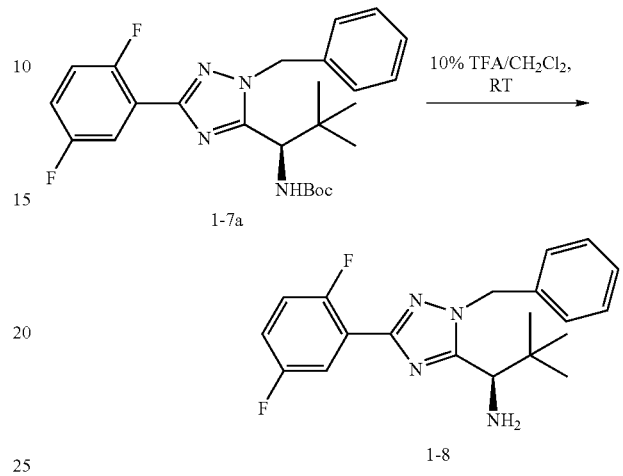

Boc-protected amine (1.0 mmol) was treated with 10% TFA in CH$_2$Cl$_2$ (5 ml). Once reaction was complete, the reaction was concentrated in vacuo and then partitioned between EtOAc and sat. aq. NaHCO$_3$. The organics were separated, then washed with sat. aq. NaHCO$_3$ (×2), H$_2$O (×2), sat. brine (×2), then dried (Na$_2$SO$_4$), filtered, and evaporated under reduced pressure to give the phenyl triazole free amine which was pure enough to use directly in the next step Step G: Reductive Amination to Install Side Chain

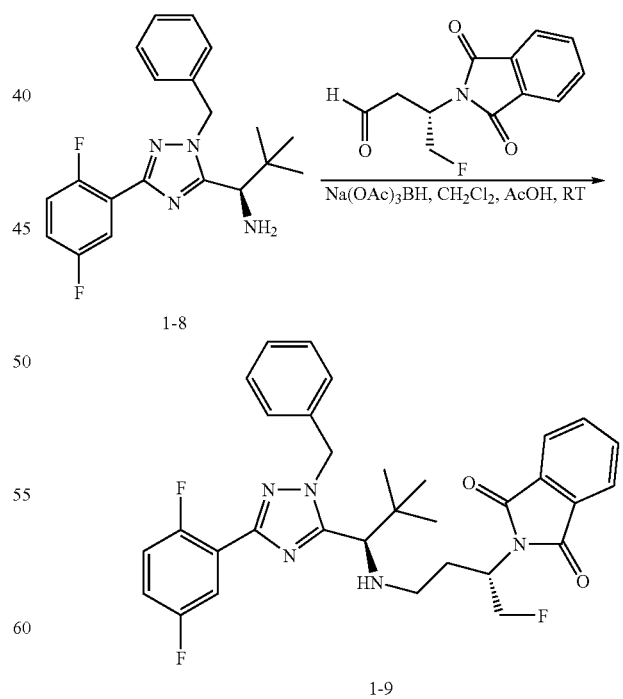

To a stirred solution of triazole amine (1.0 mmol) and appropriate aldehyde, eg, (S)-3-(1,3-dioxoisoindolin-2-yl)-4-fluorobutanal (1.0 mmol) in CH$_2$Cl$_2$ (7 mL) was added AcOH (1.0 mmol). The mixture was allowed to stir for 5 min before the addition of sodium triacetoxyborohydride (1.10 mmol). Once the reaction was complete, the mixture was concentrated in vacuo, partitioned between EtOAc and 2M aq. Na₂CO₃. The organics were separated, then washed with 2M aq. Na₂CO₃ (×2), H₂O (×2), sat. brine (×2), then dried (Na₂SO₄), filtered, and evaporated under reduced pressure to give product which was either purified by silica gel column, or more usually was pure enough to use directly in the next step.

Step H: Acylation

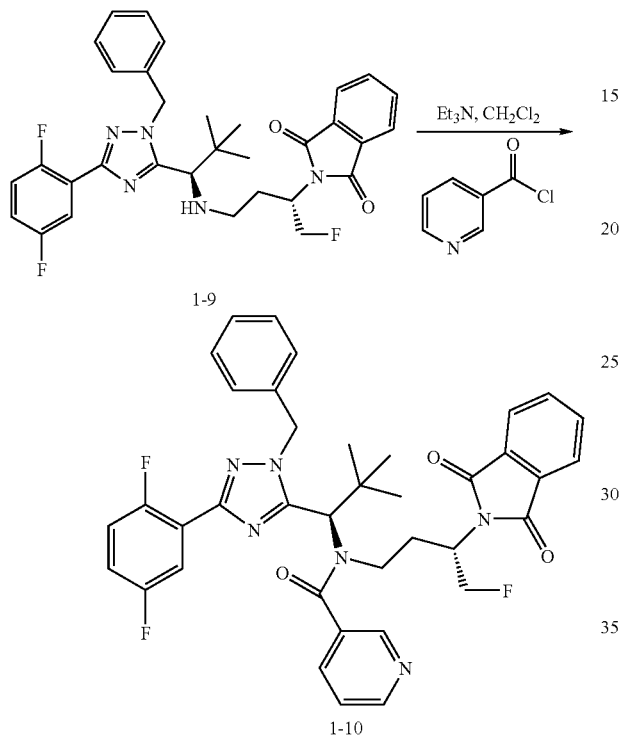

To a stirred solution of amine 1-9 (1.0 mmol) in CH₂Cl₂ (6 ml) was added Et₃N (2.0 mmol) followed by the appropriate acid chloride, eg, nicotinyl chloride (1.0 mmol). Once the reaction was complete, the mixture was partitioned between CH₂Cl₂ and sat. aq. NaHCO₃. The organics were separated and washed with H₂O (×2), sat. brine (×2), then dried (Na₂SO₄), filtered, and evaporated under reduced pressure to give product.

Step I: Final Deprotection to Eg5 Inhibitor

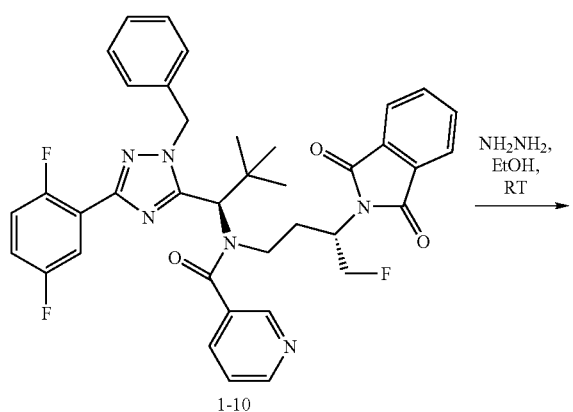

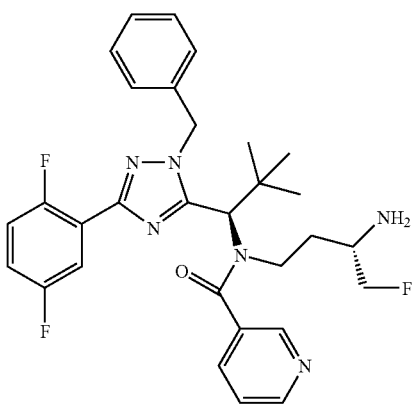

To a stirred solution of phthalimido compound 1-10 (0.3 mmol) in EtOH (1.5 mL) was added anhydrous hydrazine (1.5 mmol). Once the reaction was complete, the reaction was evaporated under reduced pressure to give the title compound, which was purified by reverse phase prep HPLC.

Example 2

N—((S)-3-amino-4-fluorobutyl)-N—((R)-1-(1-benzyl-3-(2,5-difluorophenyl)-1H-1,2,4-triazol-5-yl)-2,2-dimethylpropyl)nicotinamide Step A: Carbamic Chloride Formation -continued

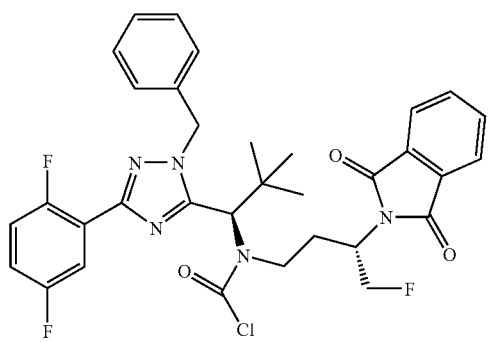

To a solution of amine 9 (0.154 mmol) in DCM (2 mL) was added Et$_3$N (0.615 mmol) followed by triphosgene (0.184 mmol). Once the reaction was complete, the reaction mixture was concentrated in vacuo, partitioned between EtOAc and sat. aq. NaHCO$_3$. The organics were separated, then washed with sat. aq. NaHCO$_3$ (×2), H$_2$O (×1), brine (×2), then dried (Na$_2$SO$_4$), filtered, and evaporated under reduced pressure to give crude carbamic chloride which was used directly in the next step.

Step B: Urea Formation

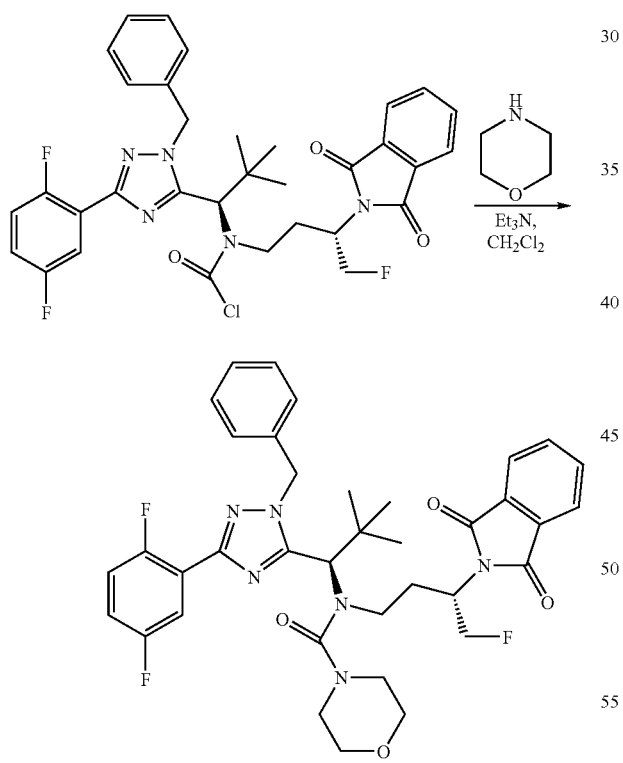

To a stirred solution of carbamic chloride (0.032 mmol) in DCM (1 mL) was added Et$_3$N (0.161 mmol) followed by appropriate amine, e.g., morpholine (0.097 mmol). Once the reaction was complete, the mixture was concentrated in vacuo, partitioned between EtOAc and sat. aq. NaHCO$_3$. The organics were separated, then washed with sat. aq. NaHCO$_3$ (×2), H$_2$O (×1), brine (×2), then dried (Na$_2$SO$_4$), filtered, and evaporated under reduced pressure to give crude product.

Step C: Deprotection

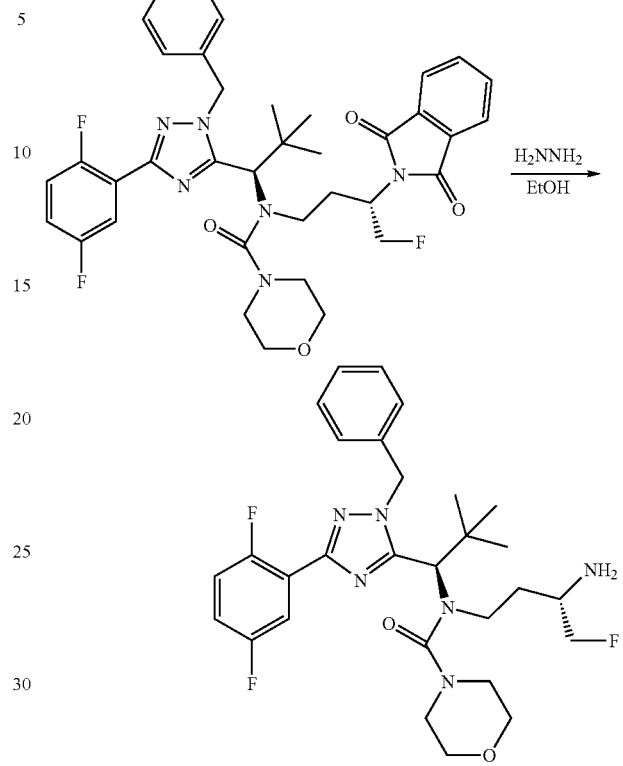

Removal of the phthalimide protecting group according to the procedure of Example 1 gives N—((S)-3-amino-4-fluorobutyl)-N—((R)-1-(1-benzyl-3-(2,5-difluorophenyl)-1H-1,2,4-triazol-5-yl)-2,2-dimethylpropyl)nicotinamide. $^1$H NMR (300 MHz, CDCl$_3$): δ 7.80 (m, 1H), 7.43 (m, 2H), 7.35 (m, 3H), 7.1 (m, 2H), 5.85 (d, 1H), 5.50 (d, 1H), 5.25 (s, 1H), 3.98-4.30 (m, 2H), 3.45-3.80 (m, 8H), 3.0-3.2 (m, 3H), 1.25 (m, 2H), 0.8 (s, 9H).

Example 3

Synthesis of (2,2-dimethyl-[1,3]dioxan-5-yl)-methanol

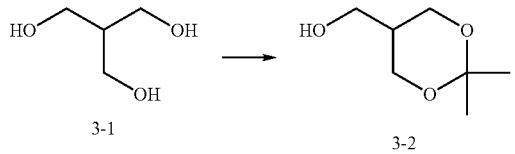

Triol 3-1 (1 eq.) was dissolved in DMF at a concentration of approximately 0.5 M and 2,2-dimethoxypropane (1.16 eq.) and p-toluenesulfonic acid monohydrate (0.03 eq.) were added. The solution was stirred for one or more days, and was quenched with TEA (0.5 eq.). As much solvent as possible was removed in vacuo and the remainder was purified by distillation under vacuum.

Example 4

2,2-dimethyl-1,3-dioxane-5-carbaldehyde

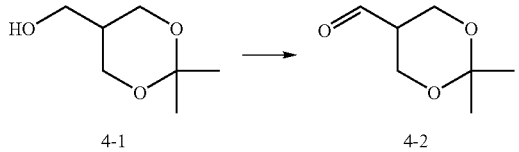

Under N₂ atmosphere, oxalyl chloride (1.4 eq.) was dissolved in DCM then cooled to −78° C. Dropwise, DMSO (2.2 eq.) was added. This solution was stirred for about 10 minutes, then triol 3-2 (1 eq.) was dissolved in more DCM for a total concentration of 0.2 M. After reacting for 5 minutes, TEA (5 eq.) was added. This mixture stirred for 10 minutes at −78° C., then for another 10 minutes at room temperature. This reaction was best monitored by TLC using a 1:1 ratio of hexane to ethyl acetate as the developing solvent and visualizing the results with CAM stain. The reaction mixture was used without further workup.

Example 5

(R)-6-(aminomethyl)-4-((R)-1-(1-benzyl-3-phenyl-1H-1,2,4-triazol-5-yl)-2,2-dimethylpropyl)-1,4-oxazepan-3-one

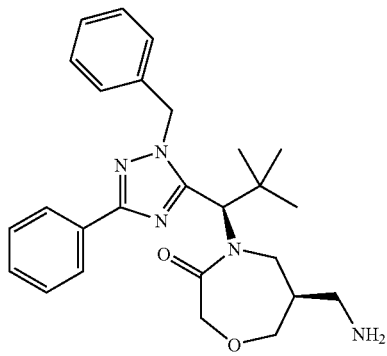

Step A: Reductive Amination

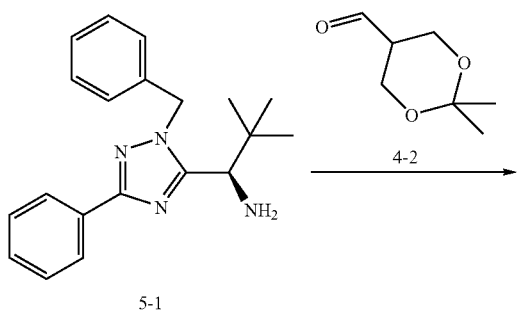

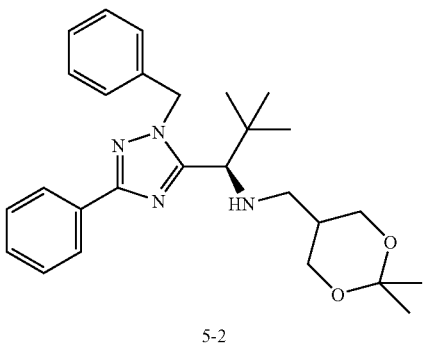

Amine 5-1 (1 eq.) dissolved in DCM is added to aldehyde 4-2 for a total concentration between 0.1-0.15 M. After 5 minutes the reaction is cooled to 0° C. and Na(OAc)₃BH (1.5 eq.) and glacial acetic acid (1 eq.) is added. The reaction is monitored by LCMS for completion. The reaction is diluted with ethyl acetate then washed three times with a saturated sodium bicarbonate solution in water. Finally, the product is dried with anhydrous sodium sulfate, filtered, and the solvent is removed in vacuo.

Step B: Acetylation

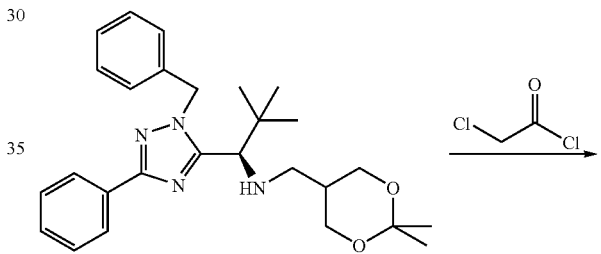

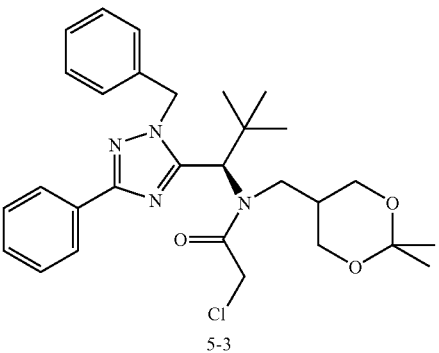

Amine 5-2 is dissolved in DCM to make a 0.2 M solution and cooled to 0° C. Slowly, TEA (5 eq.) is added and stirred for 5 minutes. Chloroacetyl chloride (3 eq.) is added dropwise. The reaction is worked-up upon completion of the reaction by diluting with ethyl acetate then washing three times with a saturated sodium bicarbonate solution in water. Finally, the product is dried with anhydrous sodium sulfate, filtered, and the solvent is removed in vacuo. The product is purified by chromatography using a gradient of about 0-70% ethyl acetate in hexane.

Step C: Diol Deprotection

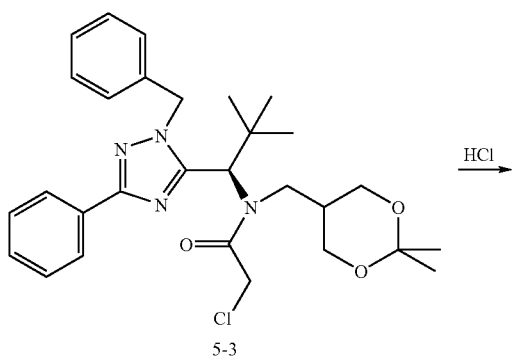

Chloride 5-3 is dissolved in acetonitrile and cooled to 0° C. 3N HCl is added dropwise and the reaction monitored by LCMS, with further addition of HCl until deprotection is complete. The solution is concentrated in vacuo, diluted with ethyl acetate, and washed three times with a saturated sodium bicarbonate solution in water. Finally, the product is dried with anhydrous sodium sulfate, filtered, and the solvent is removed in vacuo.

Step D: Cyclization

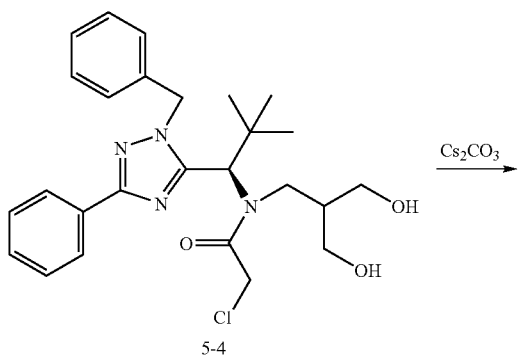

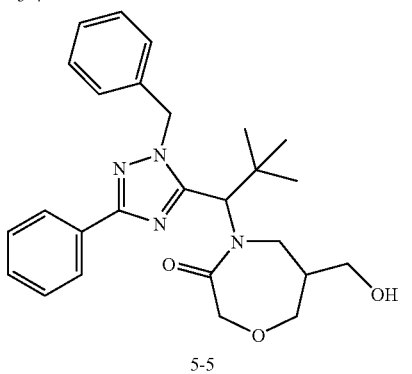

The deprotected alcohol is dissolved in DMF to make a 0.1M solution. One equivalent of $Cs_2CO_3$ and a catalytic amount of TBAI (tetrabutyl ammonium iodide) is added. The reaction is heated to approximately 40-55° C. for 4-6 hours. On completion the reaction is concentrated in vacuo, diluted with EtOAc, and washed with saturated bicarbonate. The EtOAc layer is concentrated in vacuo and purified by chromatography using a gradient of about 0-75% ethyl acetate in hexane.

Step E. Aldehyde Formation to Racemise Alcohol

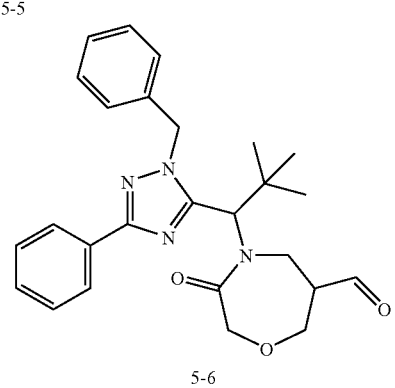

Under $N_2$ gas, oxalyl chloride (1.4 eq.) is dissolved in DCM and then cooled to −78° C. Dropwise, DMSO (2.2 eq) is added. This solution is stirred for about 10 minutes, then alcohol 5-5 (1 eq.) is dissolved in more DCM for a total concentration of 0.2M. After reacting for 5 minutes, TEA (5 eq.) is added. This mixture is stirred for 10 minutes at −78° C., then another 10 minutes at room temperature. The reaction is diluted with ethyl acetate then washed three times with a saturated sodium bicarbonate solution in water. Finally, the product is dried with anhydrous sodium sulfate, filtered, and the solvent is removed in vacuo.

Step F: Conversion to the (R) and (S) Alcohols

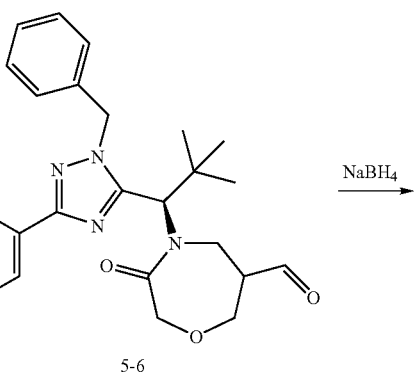

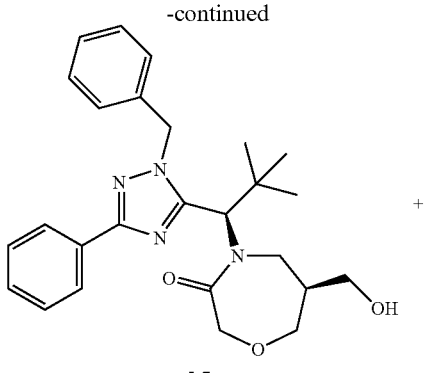

5-7a

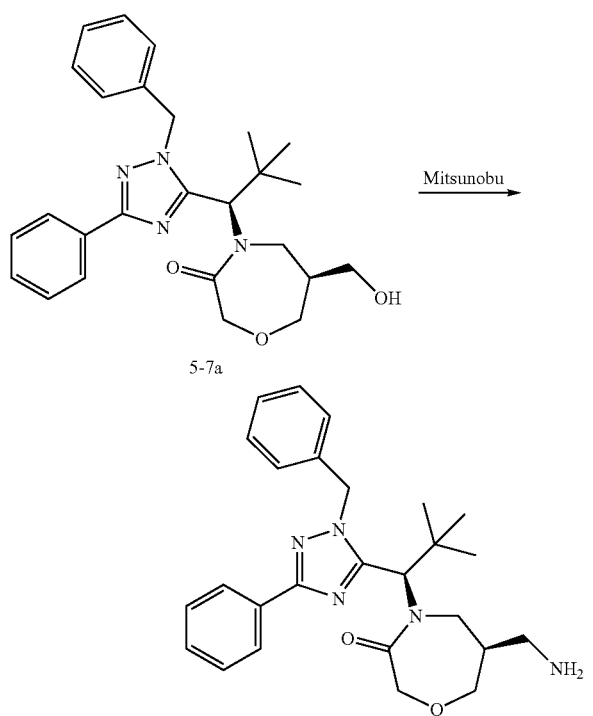

5-7b

Aldehyde 5-6 is dissolved in methanol to form a 0.2 M solution and cooled to 0° C. Sodium borohydride (1.5 eq.) is added, and the reaction is maintained for 5 to 10 minutes. The solution is concentrated in vacuo, diluted with EtOAc, and washed with saturated bicarbonate. The EtOAc layer is concentrated in vacuo and purified by chromatography. At this step the two diastereomers of the alcohol are separated by reverse phase HPLC.
Step F: Conversion to Amine To each resolved alcohol diastereomer dissolved in dry THF is added 5 eq of resin bound $PPh_3$, 5 eq of phthalimide, and 5 eq DIAD. The reaction is warmed to about 55° C. for 30 min. On complete conversion to the phthalimido derivative, the reaction is diluted with EOAc, filtered through celite, and washed with saturated $NaHCO_3$. The EtOAc layer was dried over anhydrous $Na_2SO_4$ and concentrated in vacuo, and purified by HPLC. The purified phthalimido derivatives were subjected to a final deprotection step with 2M $MeNH_2$ in methanol (used as solvent) at 60° C. for about 1 h. The crude product is purified by reverse phase HPLC.

Example 6

Preparation for Intermediate of β-Fluoro Aldehyde Side Chain (6-7)

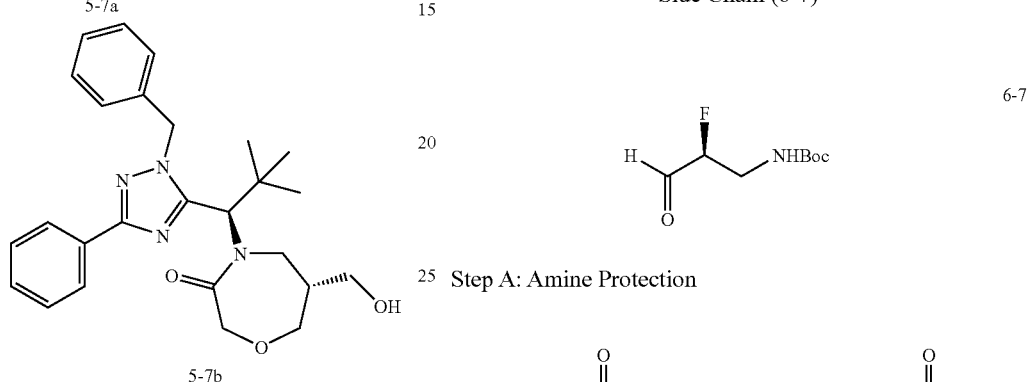

Step A: Amine Protection

To a stirred solution of anhydrous $K_2CO_3$ (46.53 g, 0.3371 mol) in DMF (500 mL), D-serine methyl ester hydrochloride (35.0 g, 0.2250 mol), KI (18.66 g, 0.1124 mol) and benzyl bromide (96.18 g, 0.5623 mol) were added in one shot. The reaction mixture was stirred vigorously for 5 h at RT. After completion of the reaction, the contents were poured into ice water and extracted with EtOAc. The combined organic layer was washed with water, brine, dried over $Na_2SO_4$ and concentrated to give a crude product 6-2. Purification was carried out by column chromatography to yield pure (61.7 g, 91.7%) as pale yellow oil.
Step B: Fluorination

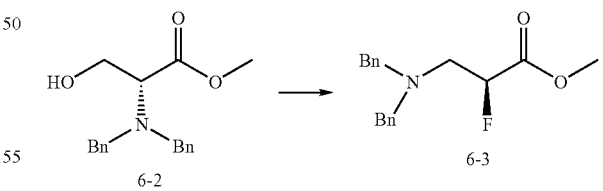

To a stirred solution of diethylamine sulphur trifluoride (32.3 mL, 0.2006 mol) in THF (400 mL), was added compound 6-2 during the span of 3 h at RT. After completion of addition, stirring was continued for further 1 h. The mixture was extracted with ethylacetate and combined organic phase was washed with saturated solution of $NaHCO_3$. Removal of solvent under vacuum lead to a crude product, which was purified by column chromatography using hexane grading to 3% EtOAc in hexane afforded product 6-3 (70.4 g, 69.9%) as pale yellow oil.

Step C: Reduction

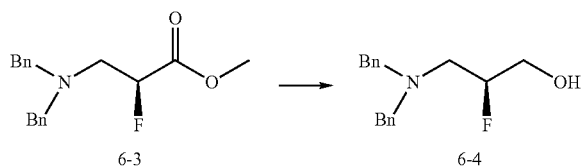

To a mechanically stirred solution of LiBH₄ (230.8 ML, 0.4651 mol) in THF (2.0 L), methyl ester (100.0 g, 0.3322 mol) in THF (1.0 L) was added dropwise 6-3 through addition funnel during the span of 3 h at −15° C. under N₂. After the completion of addition, stirring was continued for 4 h at RT. Saturated solution of NH₄Cl (500 mL) was added dropwise to the above mixture and extracted with EtOAc. The combined organic phase was washed with water, brine, dried over Na₂SO₄ and concentrated under vacuum. Residual oil was dissolved in 1N HCl (200 mL), extracted with diethylether and pH of the aq. layer was adjusted to 10 with the help of NH₄OH (50%, 300 mL). The resultant was extracted with EtOAc and combined extracts were concentrated under vacuum to give product 6-4 (86.2 g, 95.0%) as pale brown oil.

Step D: Deprotection

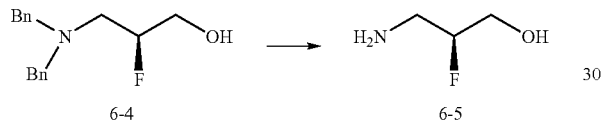

A mixture of alcohol 6-4 (50. g, 0.18315 mol) and Pd(OH)₂ on carbon (20%, 6.26 g, 0.04395 mol) in absolute ethanol (500 mL) was stirred for 7 h under the pressure of hydrogen at 50-60 psi. After the reaction, charcoal was removed by filtration and residue was concentrated on rota evaporator to provide for product 6-5 (15.8 g, 92.7%) as pale brown oil.

Step E: Boc-Protection

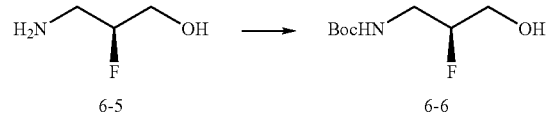

To a stirred mixture of amino alcohol 6-5 (15.0 g, 0.16129 mol) and K₂CO₃ (33.39 g, 0.24195 mol) in aq. dioxane (about 25%, 375 mL dioxane in 125 mL water), (Boc)₂O (38.66 g, 0.17733 mol) was added drop wise at 0° C. The reaction mixture was stirred overnight at RT after the addition. Saturated solution of KHSO₄ was added to the above mixture to adjust the pH 3-4 and extracted with EtOAc. The organic phase was concentrated under vacuum to give pure product 6-6 (27.7 g, 89.0%) as a pale brown oil.

Step F: Oxidation to Aldehyde

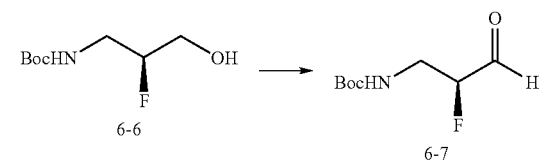

To a cooled (−78° C.), stirred solution of oxalyl chloride (84 mmol) in CH₂Cl₂ (180 mL) was added a solution of DMSO (168 mmol) in CH₂Cl₂ (90 mL). After 1 h, a solution of alcohol 6-6 (56 mmol) in CH₂Cl₂ (90 mL) was added. After 1 h, triethyl amine (281 mmol) was added and stirred for a further hour. Then a solution of saturated aq. NH₄Cl was added and allowed to warm to RT. The organics were separated, washed with H₂O (×2), saturated brine (×2), then dried, filtered and evaporated under reduced pressure to give the crude aldehyde. Purification by column chromatography afforded the pure (S)-aldehyde 6-7.

Starting from the other enantiomer, (L)-serine methyl ester leads to the (R)-enantiomer (6-8).

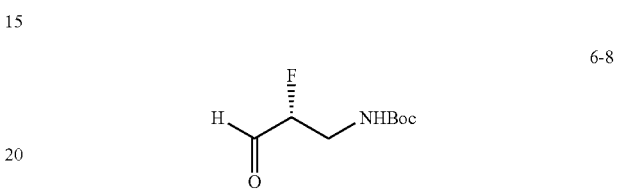

Example 7-A

Preparation for Intermediate with β-Fluoromethyl Side Chain

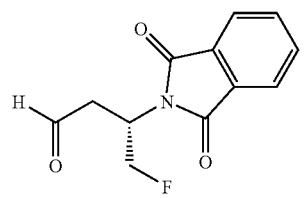

Step A: Formation of (S)-3-((benzyloxy)carbonyl)-2-(1,3-di-oxoisoindolin-2-yl)propanoic acid

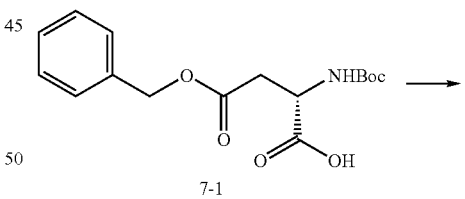

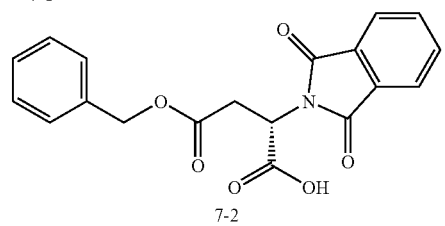

To a stirred solution of compound 7-1 (10.0 mmol) in 20 mL of DCM was added 10 mL of TFA. The mixture was stirred at RT for 24 h. The reaction progress was followed by LC/MS. After completion, the solvent and TFA were removed by evaporation under reduced pressure and lyophilization to get white solid as TFA salts. The crude solid was suspended in 50 mL of THF and N-carboethoxy phthalimide (10.5 mmol), Et₃N (10 mmol) were added. The mixture was refluxed under N₂ for 18 h. The reaction was cooled and the solvents were evaporated. DCM was added and washed with water, brine, dried over sodium sulfate, filter and concentrated. Purification by chromatography on silica gel column (hexane/EtOAc) to give 2.68 g of colorless oil, compound 7-2.

Step B: Formation of (S)-benzyl 4-hydroxy-3-(1,3-dioxoisoindolin-2-yl)butanoate

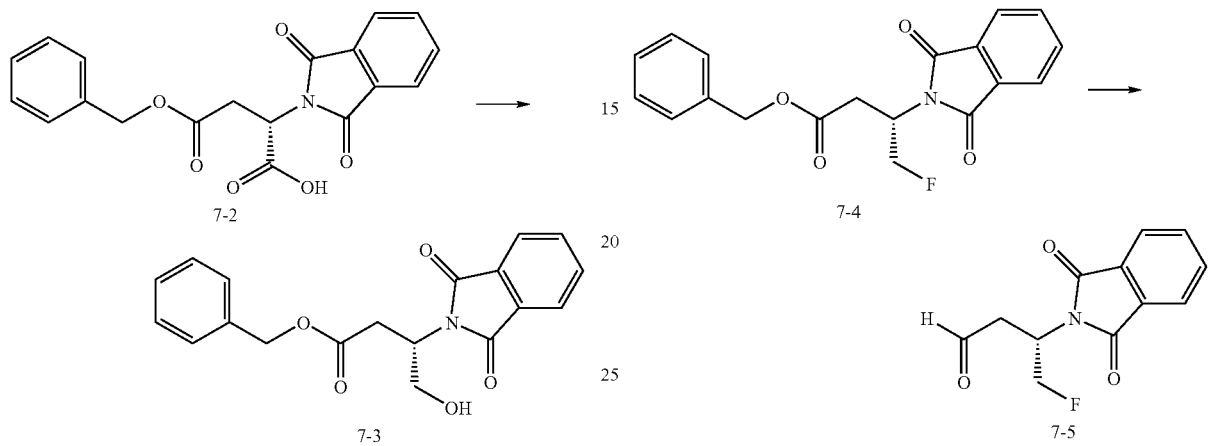

To a stirred solution of (S)-3-((benzyloxy)carbonyl)-2-(1,3-dioxoisoindolin-2-yl)propanoic acid (compound 7-2, 6.07 mmol) in 30 mL of dry THF at −15° C. were successively added N-methylmorpholine (6.07 mmol), iso-butylchloroformate (6.07 mmol). After stirring for 5 min at −15° C., a solution of NaBH₄ (689 mg, 18.21 mmol) in 2.73 mL of water were added at once. The reaction was stirred at −15° C. for 2 min, then hydrolyzed with water (30 mL). Extracted with EtOAc (×3), washed with water (×3), brine (×1), dried over sodium sulfate, filtered, concentrated. Purification by chromatography on silica gel column (hexane/EtOAc) to give 1.9 g of colorless oil, compound 7-3.

Step C: Formation of (S)-benzyl 4-fluoro-3-(1,3-dioxoisoindolin-2-yl)butanoate

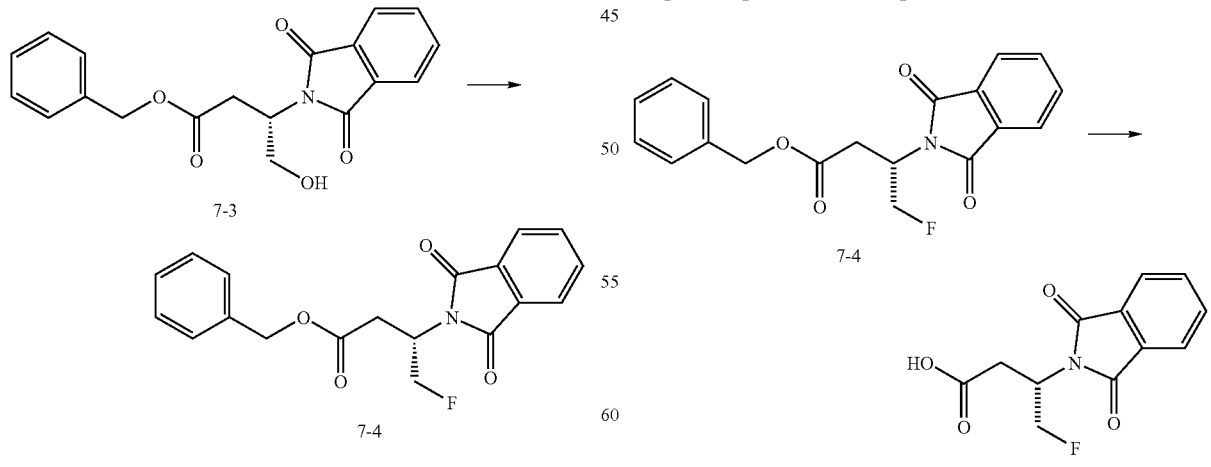

To a stirred solution of (S)-benzyl 4-hydroxy-3-(1,3-dioxoisoindolin-2-yl)butanoate (7-3, 5.6 mmol) in acetonitrile (28 mL) were added perfluoro-1-butane sulfonyl fluoride (44.8 mmol), diisopropylethylamine (44.8 mmol), and diisopropylethylamine trihydrofluoride (134 mmol). The mixture was stirred at 50° C. overnight. The reaction progress was followed by LC/MS. After completion, the reaction was cooled to RT and then evaporated under reduced pressure. The mixture was then partitioned with DCM, washed with water (×3), brine (×2), dried over sodium sulfate, filtered, concentrated. Purification by chromatography on silica gel column (hexane/EtOAc) to give light yellow oil, compound 7-4.

Step D: Formation of (S)-4-fluoro-3-(1,3-dioxoisoindolin-2-yl)butanal

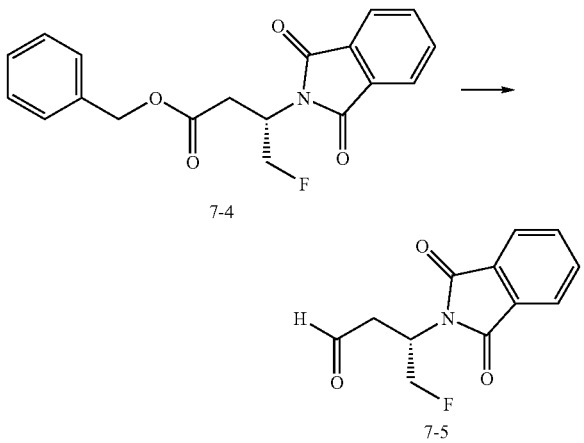

To a stirred solution of (S)-benzyl 4-fluoro-3-(1,3-dioxoisoindolin-2-yl)butanoate (compound 7-4, 0.5 mmol) in dry ether (5 mL) was added dropwise to diisobutylaluminum hydride (1.0 M in toluene, 1.5 mmol) at −78° C. The reaction was stirred at −78° C. for approximately 30 min as monitored by LC/MS. After completion, the reaction was quenched by adding water (10 mL) at −78° C. Extracted with ethyl acetate, washed with water (×3), brine (×2), dried over sodium sulfate, filtered and concentrated. The crude product, compound 7-5, was used in the next reaction step.

Example 7-B

Alternate Route for Making Compound 7-5

Step A: Preparation of Compound 7-6

To prepare (S)-4-fluoro-3-(1,3-dioxoisoindolin-2-yl)butanoic acid, compound 7-4 (0.20 mmol) was dissolved in ethanol (5 mL). This solution was purged with nitrogen for 10 minutes, then 10% palladium on carbon was added (0.02 mmol of palladium) under an atmosphere of nitrogen. Hydrogen was then bubbled rapidly through the solution, while stirring, for approximately 1 h. The reaction progress was followed with LC/MS.

The reaction mixture was filtered through celite to remove the palladium. The celite was rinsed twice with methylene chloride. The filtrate was then concentrated to give the crude product, compound 7-6. The crude product was used for the next reaction step.

Step B: Formation of (S)—S-ethyl 4-fluoro-3-(1,3-dioxoisoindolin-2-yl)butanethioate

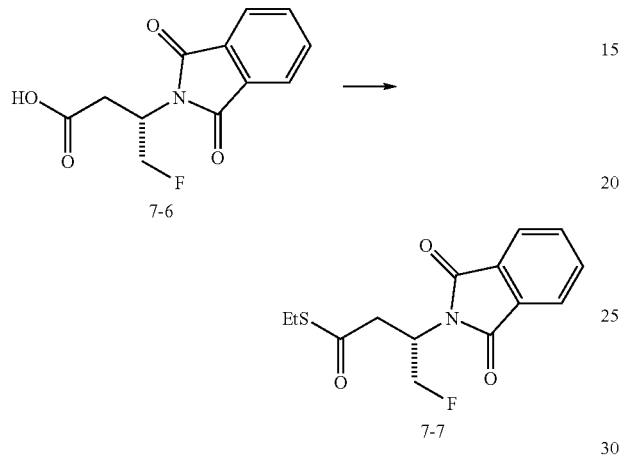

Compound 7-5 (0.20 mmol), 1,3 dicyclohexyl carbodiimide (0.30 mmol), ethanethiol (0.6 mmol), and 4-dimethylaminopyridine (0.10 mmol) were dissolved in DMF (5 mL). The mixture was stirred overnight at room temperature. The reaction was monitored with LC/MS.

EtOAc was added to the reaction mixture. This was then washed with water (2×) and brine (2×). The EtOAc layer was then dried over sodium sulfate, filtered, and concentrated. The crude product, compound 7-7, was then purified using flash chromatography.

Step C: Formation of (S)-4-fluoro-3-(1,3-dioxoisoindolin-2-yl)butanal

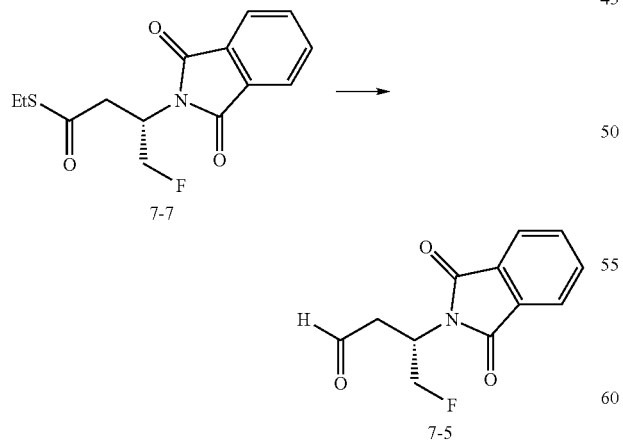

Compound 7-7 (0.20 mmol) was dissolved in dry acetone (10 mL). 10% Palladium (0.02 mmol) on carbon was then added under an atmosphere of nitrogen. Triethyl silane (0.5 mmol) was then added. Bubbling occurred after about 10 seconds, and the reaction was allowed to continue until the bubbling ceased (30 min). The reaction was monitored using LC/MS.

The reaction mixture was filtered through a celite plug. The plug was washed twice with methylene chloride, and the filtrate was then concentrated to give the crude product, compound 7-5. The crude product was used in the next reaction.

Starting from the other (R) enantiomer, (R)-3-((benzyloxy)carbonyl)-2-(1,3-dioxoisoindolin-2-yl)propanoic acid, leads to the (R) enantiomer (7-8), having the following chemical structure:

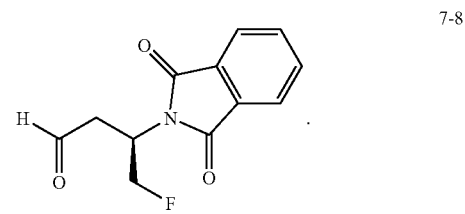

Example 7-C

Alternate Preparation for Intermediate with β-Fluoromethyl Aldehyde Side Chain

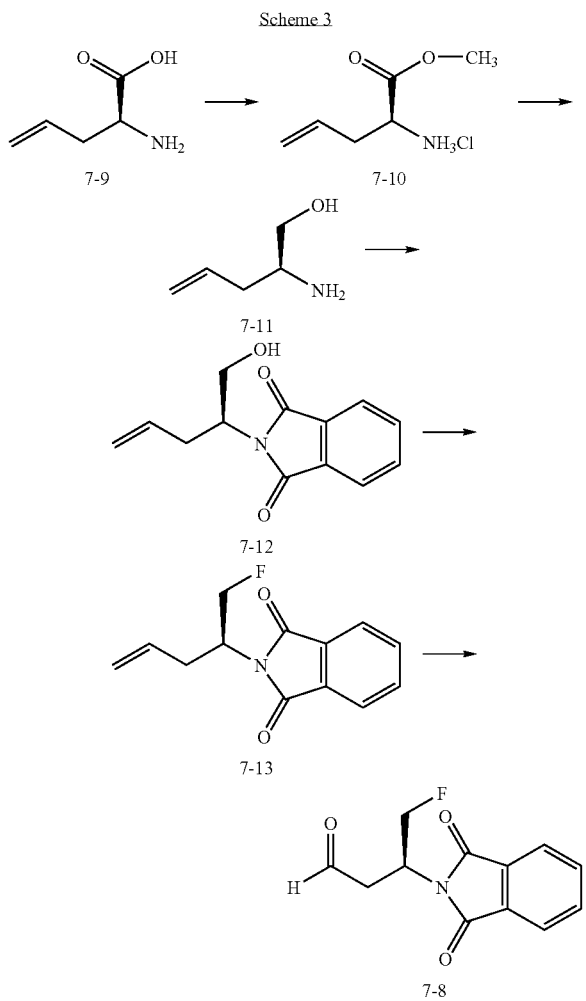

Step A: Preparation of Compound 7-10

Methanol (300 mL) was charged to a 1000 mL round bottom flask and the system was cooled with an ice bath. Acetyl chloride (89.3 mL; 1251 mmol) was added dropwise over a period of 15 minutes. The resulting solution was warmed to ambient temperature and the (S)-2-amino-4-pentenoic acid (7-9) (6.0 g; 139 mmol) was added in a single portion. The reaction mixture was heated at reflux for two hours and was then cooled to ambient temperature. The mixture was then concentrated in vacuo to provide a pale yellow oil. The product was dispersed in ethyl acetate (150 mL) and was again concentrated in vacuo; This sequence was repeated four times. The product 7-10 was an oil that solidified upon standing under vacuum overnight. $^1$H NMR analysis showed the product to be of sufficient purity for use without further purification.

TLC: $R_f$=7.1 (silica; eluant 5:3:1 CHCl$_3$:MeOH:(7:3 H$_2$O: AcOH); visualization with ninhydrin).

$^1$H NMR (400 MHz, CD$_3$OD): δ 5.84-5.73 (m, 1H), 5.32-5.26 (m, 2H), 4.17 (dd, 1H, J=7.0, 1.6 MHz), 3.84 (s, 3H), 2.73-2.65 (m, 2H); (400 MHz, d6-DMSO): δ 8.7 (br s, 3H), 5.81-5.73 (m, 1H), 5.21-5.14 (m, 2H), 4.11 (t, 1H, J=6.1 Hz), 3.72 (s, 3H), 2.60 (dd, 2H, J=7.1, 0.9 Hz).

$^{13}$C NMR (101 MHz, d6-DMSO): δ 169.33, 131.37, 119.88, 52.65, 51.65, 34.22.

Step B: Preparation of Compound 7-11

The crude (S)-methyl-2-amino-4-pentenoate hydrochloride (7-10) from the previous step was dissolved in THF (190 mL) with gentle warming. The resulting solution was added dropwise to a solution of LiAlH$_4$ in THF (280 mL of a 1.0 M solution) at a rate such that the internal temperature remained at approximately 5° C. Periodically, slight heating was used to warm the addition funnel containing the (S)-methyl-2-amino-4-pentenoate hydrochloride solution to redissolve crystallized amino ester. Upon completion of addition, the addition funnel was rinsed with an additional 20 mL portion of THF. The mixture was then diluted with diethyl ether (500 mL) and the excess LiAlH$_4$ was destroyed by the sequential addition of H$_2$O (11 mL), 15% (w/v) aqueous NaOH (11 mL) and H$_2$O (33 mL) added at a rate such that the internal temperature remained below 10° C. The mixture was filtered and the filter cake was washed with additional diethyl ether. The filtrate was dried over Na$_2$SO$_4$, filtered, and concentrated in vacuo to provide a yellow liquid (7-11; 13.4 g; 95% mass recovery based upon 139.0 mmol of (S)-2-amino-4-pentenoic acid). The amino alcohol (7-11) may be purified by distillation (110° C.; 20 torr). However, minimal improvement was observed in the subsequent step so the crude material was generally used without further purification.

$^1$H NMR (400 MHz, d6-DMSO): δ 5.87-5.77 (m, 1H), 5.05-4.97 (m, 2H), 3.26 (dd, 1H, J=10.3, 5.1 Hz), 3.14 (dd, 1H, J=10.3, 6.7 Hz), 2.69-2.63 (m, 1H), 2.15-2.09 (m, 1H), 1.92-1.86 (m, 1H).

$^{13}$C NMR (101 MHz, d6-DMSO): δ 136.49, 116.31, 66.13, 52.53, 38.51.

Step C: Preparation of Compound 7-12

(S)-2-Amino-4-pentenol (7-11; 13.4 g; 132.5 mmol) and Na$_2$CO$_3$ (70.8 g; 668.0 mmol) were dissolved in H$_2$O (400 mL). CH$_3$CN (700 mL) and methyl-2-[(succinimidooxy)carbonyl]benzoate (33.1 g; 119.4 mmol) were added and the resulting mixture was vigorously stirred at ambient temperature. After 2 hours, TLC analysis showed the consumption of methyl-2-[(succinimidooxy)carbonyl]benzoate. The majority of the CH$_3$CN was removed on a rotary evaporator and the remaining material was transferred to a separatory funnel and extracted with EtOAc (3×100 mL). The combined EtOAc extracts were washed with 0.5 M HCl (2×250 mL) and brine (250 mL). The EtOAc phase was dried over Na$_2$SO$_4$, filtered and concentrated in vacuo to provide a yellow oil (7-12; 19.3 g; 70%) that was used in the next step without further purification.

$^1$H NMR (400 MHz, d6-DMSO): δ 7.90-7.83 (m, 4H), 5.74-5.64 (m, 1H), 4.99-4.91 (m, 3H), 4.27-4.20 (m, 1H), 3.90-3.84 (m, 1H), 3.63-3.58 (m, 1H), 2.64-2.44 (m, 2H).

$^{13}$C NMR (101 MHz, d6-DMSO): δ 168.25, 134.86, 134.42, 131.37, 122.94, 117.41, 60.63, 53.47, 32.59.

Step D: Preparation of Compound 7-13

N,N-Diisopropylethylamine (215 mL; 1240 mmol), triethylamine trihydrofluoride (81 mL; 496 mmol) and perfluoro-1-butanesulfonyl fluoride (15.0 mL; 83.5 mmol) were added to a solution of 7-12 (19.1 g; 82.7 mmol) in PhCF$_3$ (310 mL) and the resulting mixture was stirred at ambient temperature. Additional perfluoro-1-butanesulfonyl fluoride (7.5 mL; 41.8 mmol) was added after each of 60, 90, 120, 150, and 180 minutes. After a total of 18 hours, the reaction mixture was transferred to a separatory funnel and was washed twice with 1.0 N HCl, twice with saturated aqueous NaHCO$_3$ and once with H$_2$O. The organic phase was dried over Na$_2$SO$_4$, filtered, and concentrated to provide an orange oil. The crude material was loaded onto a pad of silica and eluted with 4:1 hexane: EtOAc to provide the product (7-13) as a yellow oil (15.4 g; 80%).

$^1$H NMR (400 MHz, d6-DMSO): δ 7.88-7.81 (m, 4H), 5.77-5.66 (m, 1H), 5.04-4.88 (m, 2.5H), 4.80-4.73 (m, 1H), 4.65-4.61 (m, 0.5H), 4.60-4.49 (m, 1H), 2.68-2.47 (m, 2H).

$^{13}$C NMR (101 MHz, d6-DMSO): δ 167.87, 134.79, 133.77, 130.94, 123.26, 118.21, 81.82 (d, J=170 Hz), 50.47 (d, J=19 Hz), 31.40 (d, J=6 Hz).

Step E: Preparation of Compound 7-8

Compound 7-13 (15.3 mmol) was dissolved in 2:1 CH$_3$OH:H$_2$O (1500 mL) and a solution of OsO$_4$ in H$_2$O (29.3 mL of a 4% w/v solution) was added. NaIO$_4$ (42.2 g; 197.2 mmol) was then added in a single portion and the resulting mixture was stirred at ambient temperature. After 3 hours, the mixture was filtered to remove precipitated solids and the filter cake was washed with EtOAc. The filtrate was concentrated in vacuo to remove the majority of the organic solvents. The residue was extracted with three portions of EtOAc and the combined EtOAc extracts were dried over Na$_2$SO$_4$, filtered, and concentrated. The residue was dissolved in CH$_2$Cl$_2$, loaded onto a pad of silica gel and sequentially eluted with 20%, 30%, 40%, 50%, and 100% EtOAc in hexane. Compound 7-8 was present in the 30%-50% fractions but contaminated with a more-polar impurity. The fractions were combined and concentrated and the residue was applied to a second pad of silica and eluted with 30% EtOAc in hexane to provide Compound 7-8 as a light yellow solid (11.1 g; 72%):

$^1$H NMR (400 MHz, d6-DMSO): δ 9.61 (s, 1H), 7.91-7.83 (m, 4H), 4.97-4.94 (m, 1H), 4.78 (t, 0.5H, J=9.3 Hz), 4.69-4.64 (m, 1H), 4.57-4.53 (m, 0.5H), 3.28-3.02 (m, 2H).

$^{13}$C NMR (101 MHz, d6-DMSO): δ 200.14, 167.65, 134.73, 131.15, 123.24, 81.80 (d, J=171 Hz), 44.81 (d, J=21 Hz), 40.64 (d, J=6 Hz).

Example 7-D

Alternate Synthesis of Compound 7-12

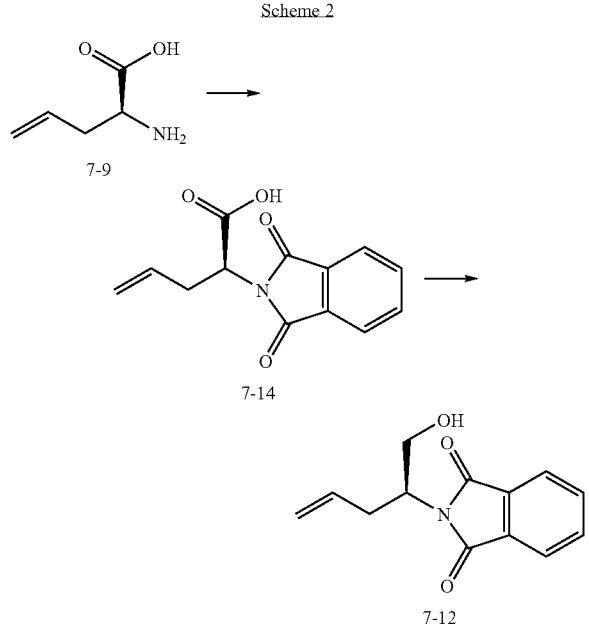

Step A: Preparation of Compound 7-14

Compound 7-9 was refluxed with 2.2 equivalents of phthalic anhydride in the presence of 2.2 equivalents triethylamine in ethyl acetate until the reaction was complete. The solvent was removed under pressure. The residual was dissolved in water with a pH of 4 and then extracted with ethyl acetate. The combined organic layers were washed twice with water having a pH of 4. Then, the organic phase was dried with sodium sulfate. The solvent was removed providing 7-14 as a white solid.

Step B: Preparation of Compound 7-12

Compound 7-14 and 1.2 equivalents of DIEA and 1.1 equivalent of BOP in THF was stirred at room temperature until a clear solution formed. The solution was cooled to 0° C., and then 1.0 equivalent of NaBH₄ was added. The reaction mixture was stirred at 0° C. under N₂ until reaction completion. The solvent to changed to DCM and the reaction was washed once with water. The DCM phase was loaded onto a silica gel plug, and flushed with 15% EtOAc in hexanes to give Compound 7-12 as a colorless oil.

Example 8

Synthesis of Intermediate (S)-tert-butyl 4-oxobutan-2-ylcarbamate

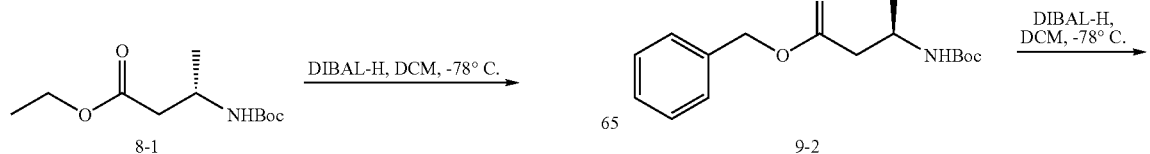

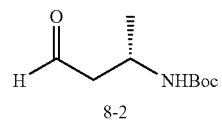

Azeotropic mixture of (S)-ethyl 3-(tert-butoxycarbonylamino) butanoate 8-1 (1 eq.) and toluene (x=3) was dissolved in dichloromethane and cooled to −78° C. Then 1M solution of DIBAL in toluene (2 eq.) was added dropwise under N₂ atmosphere and stirred at −78° C. for 2 h.

The reaction was quenched with methanol and concentrated. To the concentrated residue was added 2 M potassium sodium tartrate solution at 0° C. and stirred vigorously at room temperature for 30 min. The reaction mixture was partitioned between ethyl acetate and water. The organic layer was washed with brine, dried over sodium sulfate filtered, evaporated and dried under reduced pressure to provide compound 8-2 as a light yellow viscous liquid. MS: MH+=188.2

Example 9

Synthesis of (R)-tert-butyl 4-oxobutan-2-ylcarbamate

Step A: Synthesis of (R)-((benzyl) 3-(tert-butoxycarbonylamino)butanoate

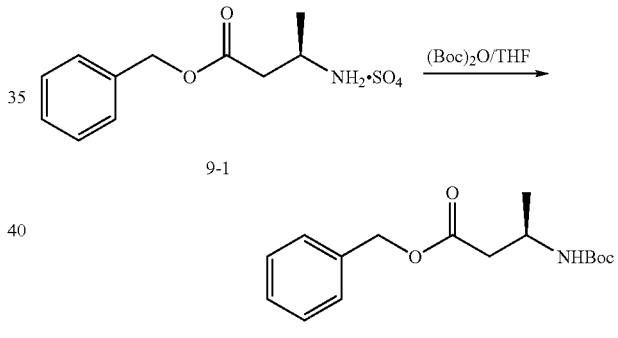

To (R)-benzyl 3-aminobutyrate sulfate salt 9-1 (1 eq.) in THF was added Boc-anhydride (2 eq.) and diisopropylethylamine (4 eq.). The reaction mixture was stirred at room temperature for 72 h. The reaction mixture was concentrated and partitioned between ethyl acetate and water. The organic layer was separated, washed with water and brine, dried over sodium sulfate, filtered, evaporated and dried under reduced pressure to provide compound 9-2 as a white solid. MS: MH+=294.0

Step B: Synthesis of (R)-tert-butyl 4-oxobutan-2-ylcarbamate

-continued

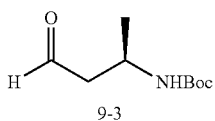

Azeotropic mixture of (R)-((benzyl) 3-(tert-butoxycarbonylamino) butanoate 9-2 (1 eq.) and toluene (x=3) was dissolved in dichloromethane and cooled to −78° C. A 1 M solution of DIBAL in toluene (2 eq.) was added dropwise under $N_2$ atmosphere and stirred at −78° C. for 2 h. The reaction was quenched with methanol and then concentrated. To the concentrated residue was added 2 M potassium sodium tartrate solution at 0° C. and stirred vigorously at room temperature for 30 min. The reaction mixture was partitioned between ethyl acetate and water. The organic layer was washed with brine, dried over sodium sulfate, filtered, evaporated and dried under reduced pressure to provide compound 9-3 as a colorless viscous liquid. MS: MH+=188.2

Example 10

Synthesis of tert-butyl 2-methyl-4-oxobutan-2-ylcarbamate

Step A: Synthesis of methyl 3-amino-3-methylbutanoate

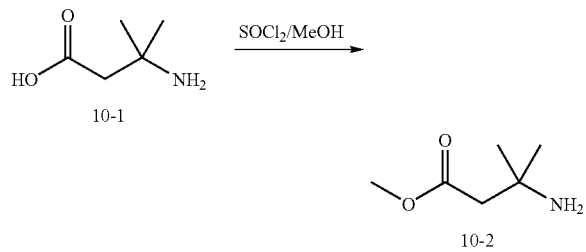

To 3-amino-3-methyl-butyric acid 10-1 (1 eq.) in methanol at 0° C. was added 2 eq. of thionyl chloride. The reaction mixture was warmed to room temperature and stirred overnight. The solvent was evaporated to give azeotropic mixture of 10-2 and toluene (x=3) which was used for Step B. MS: MH+=132.1

Step B: Synthesis of methyl 3-tert-butoxycarbonylamino)-3-methylbutanoate

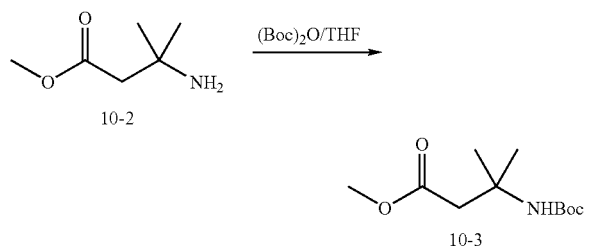

To methyl 3-amino-3-methylbutanoate HCl salt 10-2 (1 eq.) in THF was added Boc-anhydride (2 eq.) and diisopropylethylamine (4 eq.). The reaction mixture was stirred at room temperature for 48 h. The reaction mixture was concentrated and partitioned between ethyl acetate and water. The organic layer was separated, washed with water and brine, dried over sodium sulfate, filtered, evaporated and dried under reduced pressure to provide product 10-3 as a white solid. MS: MH+=232.1

Step C: Synthesis of tert-butyl 2-methyl-4-oxobutan-2-ylcarbamate

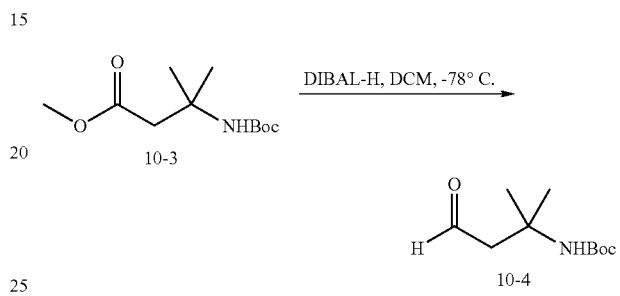

Azeotropic mixture of methyl 3-tert-butoxycarbonylamino)-3-methylbutanoate 10-3 (1 eq.) and toluene (x=3) was dissolved in dichloromethane and cooled to −78° C. To this was added dropwise 1 M solution of DIBAL in toluene (2 eq.) under $N_2$ atmosphere and stirred at −78° C. for 2 h. The reaction was quenched with methanol and concentrated. To concentrated residue was added 2 M potassium sodium tartrate solution at 0° C. and stirred vigorously at room temperature for 30 min. The mixture was partitioned between ethyl acetate and water. The organic layer was washed with brine, dried over sodium sulfate, filtered, evaporated and dried under reduced pressure to provide product 10-4 as a colorless viscous liquid. MS: MH+=202.1

Example 11

Preparation of Boc-Protected Difluoromethylaldehyde

Step A: Reductive Amination

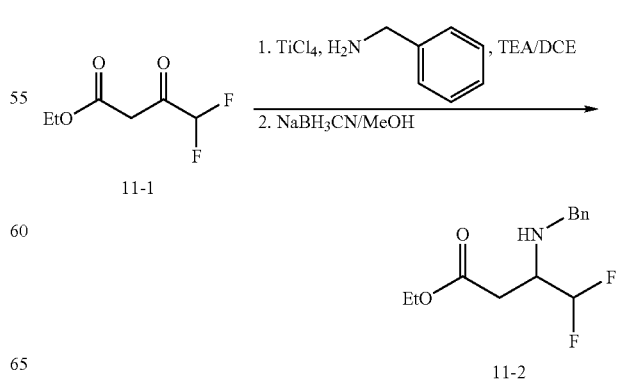

Ethyl 4,4-diflouro-3-ketobutyrate (11-1, 25 g, 15 mmol) was dissolved in dichloroethane (300 mL). Benzyl amine (49 mL, 45.2 mmol) and triethylamine (83 mL, 60.2 mmol) were then added and the solution was stirred for 1 minute. TiCl$_4$ solution (1M in DCM, 60 mL, 60.2 mmol) was then added dropwise. The mixture was stirred overnight at rt. Reaction progress was followed with TLC. Sodium cyanoborohydride dissolved in MeOH was then added dropwise over 1 hour. The reaction was stirred for an additional hour. The reaction mixture was partitioned between EtOAc and sat. sodium bicarbonate solution. Be careful to keep reaction in the hood and use a cyanide detector. The reaction was then washed with water (2×) and Brine (2×). The organic layer was dried over sodium sulfate, filtered through a fritted filter and concentrated under vacuum. Purification was done on Isco (0 to 100% EtOAc over 45 minutes) to give 11-2. Yield: 36.3 g (68%).

Step B: De-Benzylation of the Secondary Amine

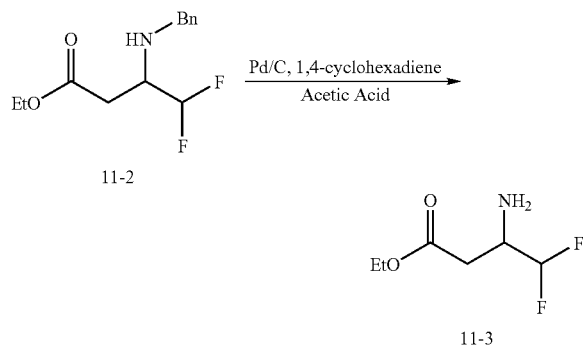

Compound 11-2 (1 eq) was dissolved in acetic acid. Palladium on carbon (0.25 eq) and 1,4-cyclohexadiene (10 eq) were added and the reaction mixture was heated to 60 degrees celsius. Stirring continued at 60 degrees for 3 hours. The reaction was followed with LCMS. The reaction was then cooled to rt and filtered through a plug of Celite. The Celite was rinsed with methanol. The filtrate was then concentrated under vacuum to yield the crude product. The crude material 11-3 was used directly in the next reaction without purification.

Step C: Protection of the Secondary Amine with Boc

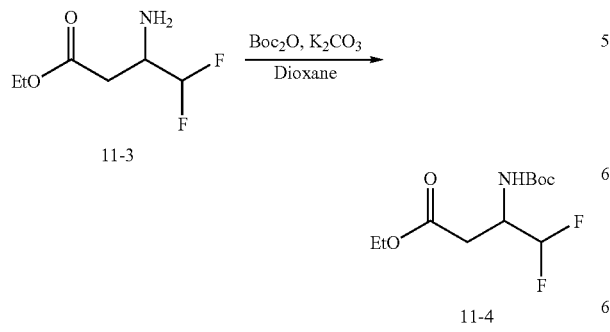

Compound 11-3 (1 eq), tert-butyl dicarbonate (1.3 eq), potassium carbonate (1.3 eq) and dioxane were all added to a flask. The reaction was stirred at rt under nitrogen for 10 hours. Reaction progress was followed with LCMS. The reaction was then evaporated to dryness. The remaining material was partitioned between water and EtOAc. The layers were separated and the aqueous layer was extracted two more times with EtOAc. The organic layers were combined, dried over sodium sulfate, filtered through a fritted filter, and concentrated under vacuum. Purification was done with ISCO column (0% to 30% EtOAc over 35 min, 30% to 100% over 5 min, 100% for 5 min).

Step D: Reduction of Ethyl Ester to Aldehyde

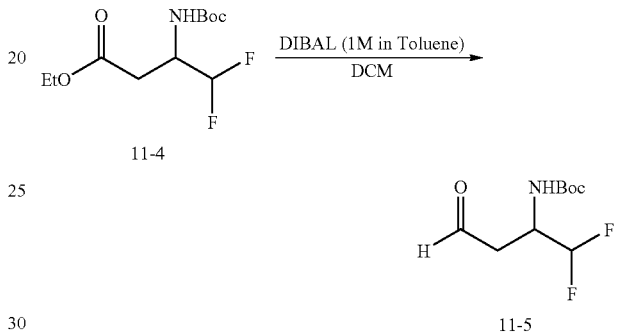

Compound 11-4 (2.8 g, 10.48 mmol) was dissolved in DCM and placed under an atmosphere of nitrogen. This solution was cooled to −78 degrees celsius in an acetone/dry ice bath. DIBAL solution (1M in toluene, 20.97 mL, 20.97 mmol) was added dropwise. The reaction was then stirred for 2 additional hours. The reaction was followed with LCMS. The reaction was then quenched with methanol and stirred for 5 min. Methanol was then evaporated under reduced pressure. The remaining aqueous phase was extracted with EtOAc (3×). The collected EtOAc extractions were dried over sodium sulfate, filtered through a fritted filter and concentrated under vacuum. Purification was done with Isco ((0% to 40% EtOAc over 35 min, 40% to 100% over 5 min, 100% for 10 min) to give 11-5. Yield: 1.8 g (77.0%).

Step E: Reductive Amination

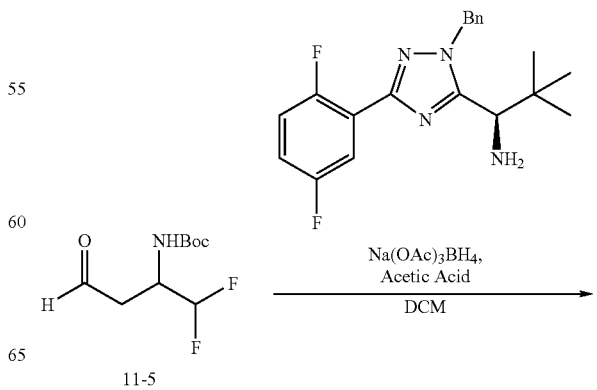

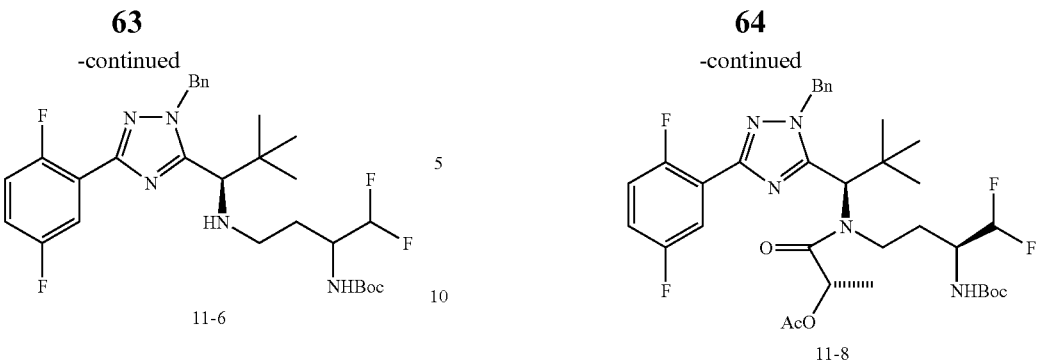

Compound 11-5 (31 mg, 0.14 mmol) was dissolved in DCM. The triazole (65 mg, 0.14 mmol), sodium triacetoxyborohydride (44 mg, 0.21 mmol), and acetic acid (0.013 mL, 0.21 mmol) were added and the reaction mixture was stirred at rt overnight. The reaction was followed with LCMS. After completion, the reaction was washed with water (2×). The DCM layer was then dried over sodium sulfate, filtered with a fritted filter, and concentrated under vacuum. Purification was done with Isco column (0% to 30% EtOAc over 25 min, 30% to 100% over 10 min, 100% for 5 min) Yield: 58.0 mg (77.0%).

Step F: Acylation

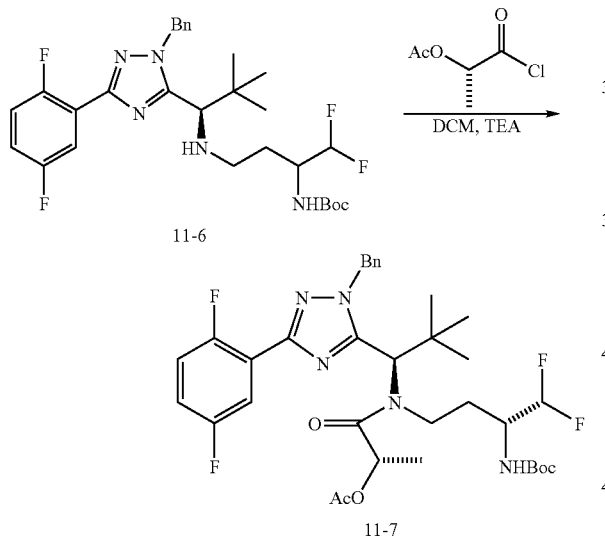

Compound 11-6 (58.0 mg, 0.11 mmol) was dissolved in DCM in a screw cap vial. (S)-2-Acetoxypropanoyl chloride (0.042 mL, 0.33 mmol) and triethylamine (0.046 mL, 0.33 mmol) were then added. The vial was sealed and heated to 40 degrees celsius. The reaction was stirred at 40 degrees celsius overnight. After reaction completion, the solvent was removed under vacuum. The reaction mixture was taken up in acetonitrile and water, and the isomers were separated using reverse phase chromatography. The S-isomer showed a retention time of 1.29 minute on LCMS; the R-isomer showed a retention time of 1.33 minute, Yield of the S-isomer: 15.4 mg (20.7%). Yield of the R-isomer: 15.9 mg (21.4%).

Compounds 1-15, and 18-86 in the table below were prepared using the methodology described in the previous Examples and Methods. Compounds 16 and 17 are prophetic compounds and can also be prepared in a similar manner. The starting materials used in the synthesis are recognizable to one of skill in the art and are commercially available or may be prepared using known methods. The compounds in Table 1 were named using AutoNom 2000 (Automatic Nomenclature) for ISIS/Base, implementing IUPAC standardized nomenclature. In one embodiment, provided is a stereoisomer of any one of the compounds in Table 1. In one aspect, the stereoisomer is an enantiomer. In another aspect, the stereoisomer is a diastereomer.

TABLE 1

| Compound | Structure | MH+ | Name |
|---|---|---|---|
| 1 | 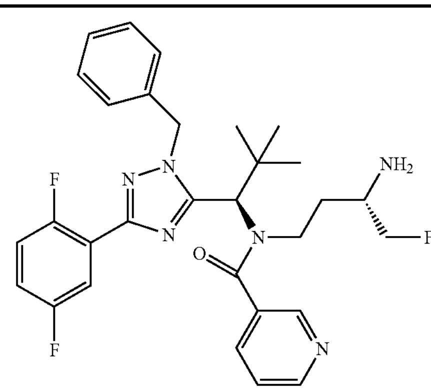 | 551.2 | N-((S)-3-amino-4-fluorobutyl)-N-((R)-1-(1-benzyl-3-(2,5-difluorophenyl)-1H-1,2,4-triazol-5-yl)-2,2-dimethylpropyl)nicotinamide |

TABLE 1-continued

| Compound | Structure | MH+ | Name |
|---|---|---|---|
| 2 | 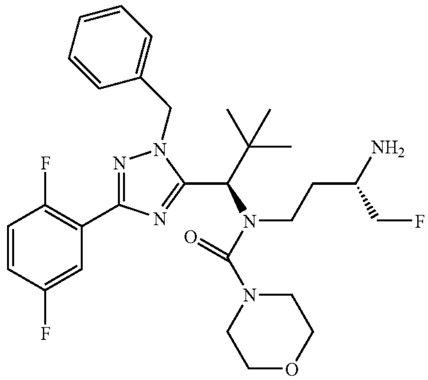 | 559.2 | N-((S)-3-amino-4-fluorobutyl)-N-((R)-1-(1-benzyl-3-(2,5-difluorophenyl)-1H-1,2,4-triazol-5-yl)-2,2-dimethylpropyl)morpholine-4-carboxamide |
| 3 | 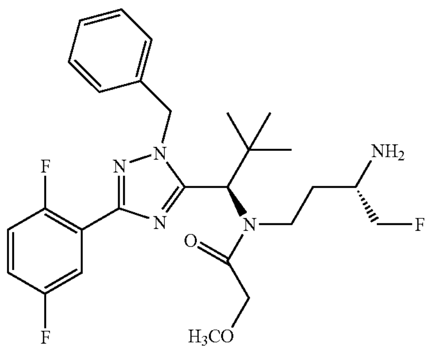 | 518.3 | N-((S)-3-amino-4-fluorobutyl)-N-((R)-1-(1-benzyl-3-(2,5-difluorophenyl)-1H-1,2,4-triazol-5-yl)-2,2-dimethylpropyl)-2-methoxyacetamide |
| 4 | 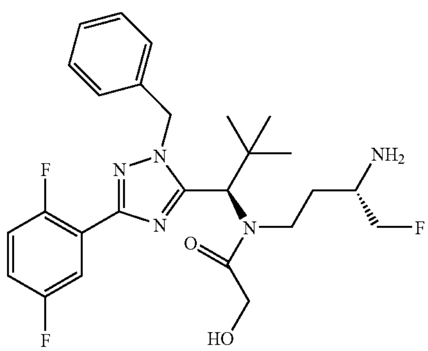 | 504.2 | N-((S)-3-amino-4-fluorobutyl)-N-((R)-1-(1-benzyl-3-(2,5-difluorophenyl)-1H-1,2,4-triazol-5-yl)-2,2-dimethylpropyl)-2-hydroxyacetamide |
| 5 | 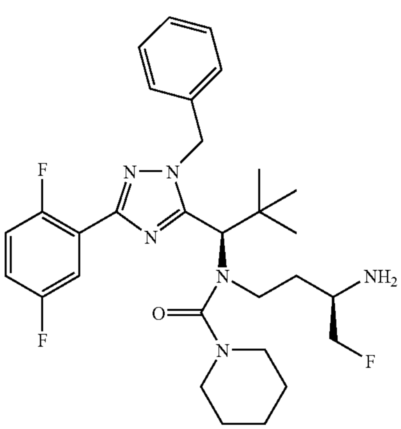 | 557.3 | N-((R)-3-amino-4-fluorobutyl)-N-((R)-1-(1-benzyl-3-(2,5-difluorophenyl)-1H-1,2,4-triazol-5-yl)-2,2-dimethylpropyl)piperidine-1-carboxamide |

TABLE 1-continued

| Compound | Structure | MH+ | Name |
|---|---|---|---|
| 6 | 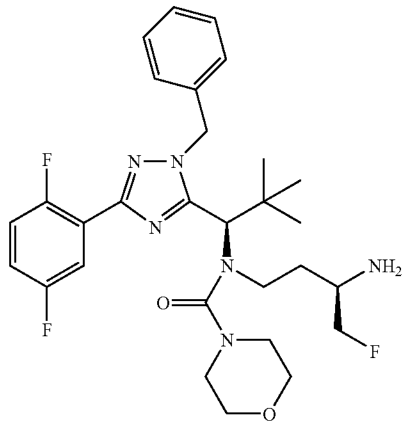 | 559.3 | N-((R)-3-amino-4-fluorobutyl)-N-((R)-1-(1-benzyl-3-(2,5-difluorophenyl)-1H-1,2,4-triazol-5-yl)-2,2-dimethylpropyl)morpholine-4-carboxamide |
| 7 | 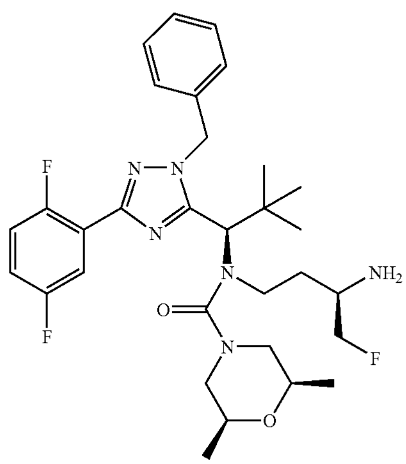 | 587.3 | (2S,6R)-N-((R)-3-amino-4-fluorobutyl)-N-((R)-1-(1-benzyl-3-(2,5-difluorophenyl)-1H-1,2,4-triazol-5-yl)-2,2-dimethylpropyl)-2,6-dimethylmorpholine-4-carboxamide |
| 8 | 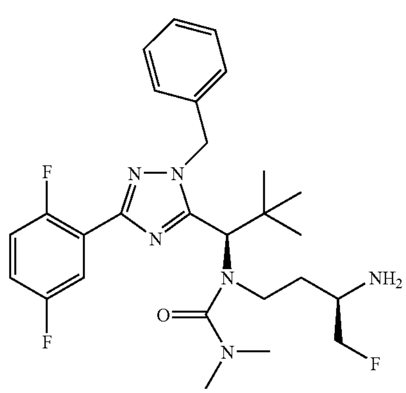 | 517.3 | 1-((R)-3-amino-4-fluorobutyl)-1-((R)-1-(1-benzyl-3-(2,5-difluorophenyl)-1H-1,2,4-triazol-5-yl)-2,2-dimethylpropyl)-3,3-dimethylurea |

TABLE 1-continued

| Compound | Structure | MH+ | Name |
|---|---|---|---|
| 9 | 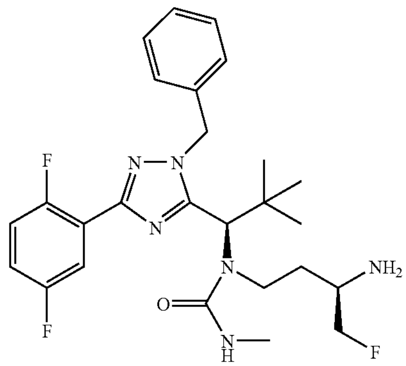 | 503.2 | 1-((R)-3-amino-4-fluorobutyl)-1-((R)-1-(1-benzyl-3-(2,5-difluorophenyl)-1H-1,2,4-triazol-5-yl)-2,2-dimethylpropyl)-3-methylurea |
| 10 | 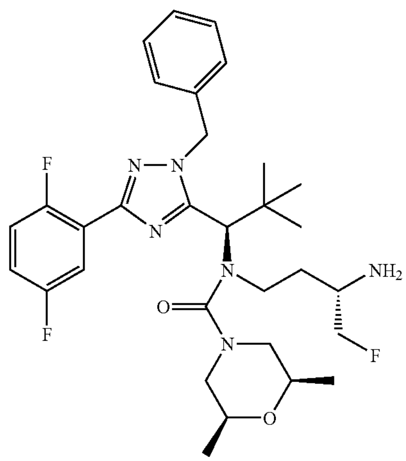 | 587.3 | (2S,6R)-N-((S)-3-amino-4-fluorobutyl)-N-((R)-1-(1-benzyl-3-(2,5-difluorophenyl)-1H-1,2,4-triazol-5-yl)-2,2-dimethylpropyl)-2,6-dimethylmorpholine-4-carboxamide |
| 11 | 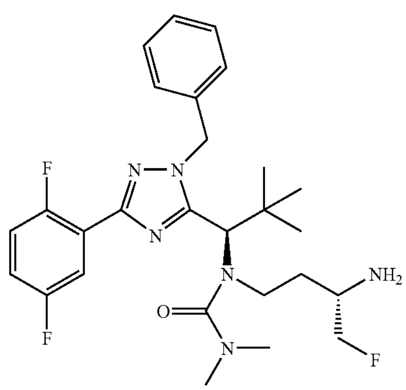 | 517.3 | 1-((S)-3-amino-4-fluorobutyl)-1-((R)-1-(1-benzyl-3-(2,5-difluorophenyl)-1H-1,2,4-triazol-5-yl)-2,2-dimethylpropyl)-3,3-dimethylurea |
| 12 | 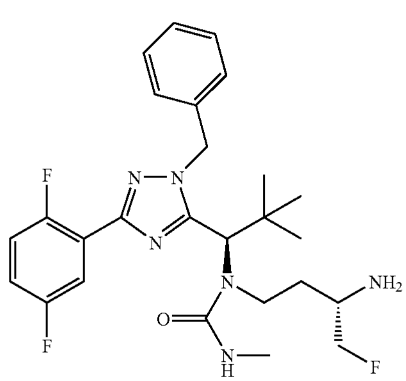 | 503.2 | 1-((S)-3-amino-4-fluorobutyl)-1-((R)-1-(1-benzyl-3-(2,5-difluorophenyl)-1H-1,2,4-triazol-5-yl)-2,2-dimethylpropyl)-3-methylurea |

TABLE 1-continued

| Compound | Structure | MH+ | Name |
|---|---|---|---|
| 13 | 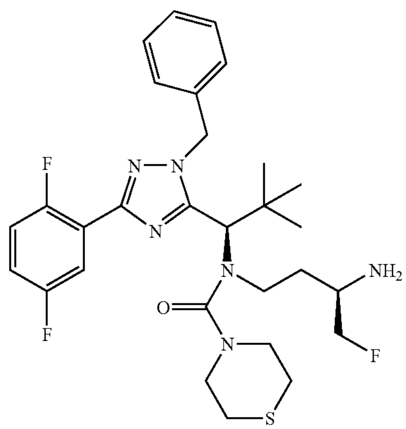 | 575.2 | N-((R)-3-amino-4-fluorobutyl)-N-((R)-1-(1-benzyl-3-(2,5-difluorophenyl)-1H-1,2,4-triazol-5-yl)-2,2-dimethylpropyl)thiomorpholine-4-carboxamide |
| 14 | 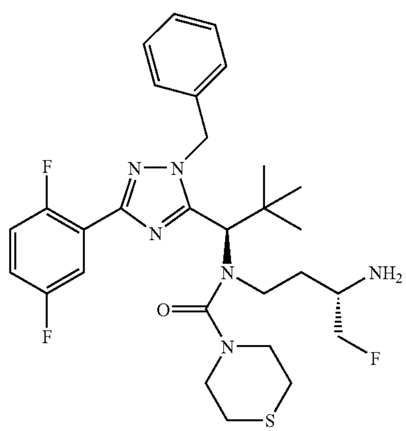 | 575.2 | N-((S)-3-amino-4-fluorobutyl)-N-((R)-1-(1-benzyl-3-(2,5-difluorophenyl)-1H-1,2,4-triazol-5-yl)-2,2-dimethylpropyl)thiomorpholine-4-carboxamide |
| 15 | 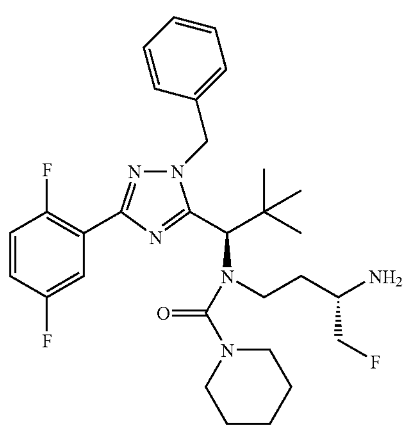 | 557.2 | N-((S)-3-amino-4-fluorobutyl)-N-((R)-1-(1-benzyl-3-(2,5-difluorophenyl)-1H-1,2,4-triazol-5-yl)-2,2-dimethylpropyl)piperidine-1-carboxamide |
| 16 | 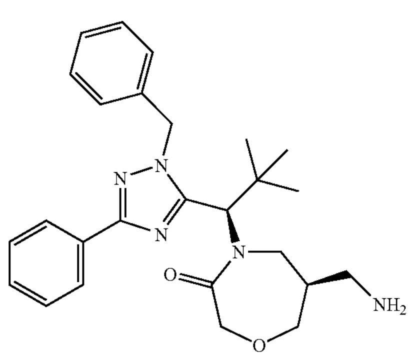 | | (R)-6-(aminomethyl)-4-((R)-1-(1-benzyl-3-phenyl-1H-1,2,4-triazol-5-yl)-2,2-dimethylpropyl)-1,4-oxazepan-3-one |

TABLE 1-continued

| Compound | Structure | MH+ | Name |
|---|---|---|---|
| 17 | 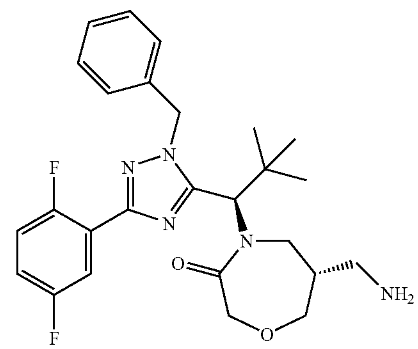 | | (S)-6-(aminomethyl)-4-((R)-1-(1-benzyl-3-(2,5-difluorophenyl)-1H-1,2,4-triazol-5-yl)-2,2-dimethylpropyl)-1,4-oxazepan-3-one |
| 18 | 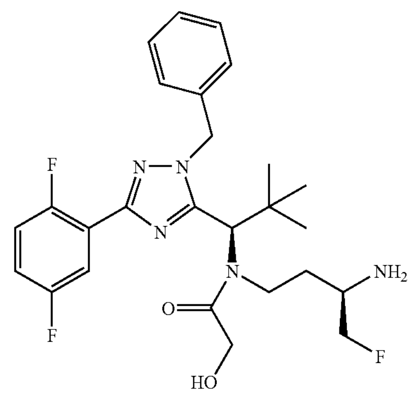 | 504.2 | N-((R)-3-amino-4-fluorobutyl)-N-((R)-1-(2-benzyl-5-(2,5-difluorophenyl)-2H-1,2,4-triazol-3-yl)-2,2-dimethylpropyl)-2-hydroxyacetamide |
| 19 | 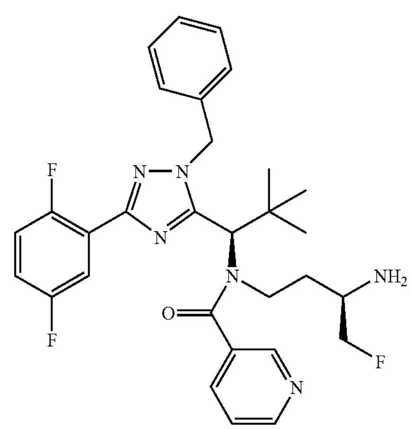 | 551.2 | N-((R)-3-amino-4-fluorobutyl)-N-((R)-1-(2-benzyl-5-(2,5-difluorophenyl)-2H-1,2,4-triazol-3-yl)-2,2-dimethylpropyl)nicotinamide |
| 20 | 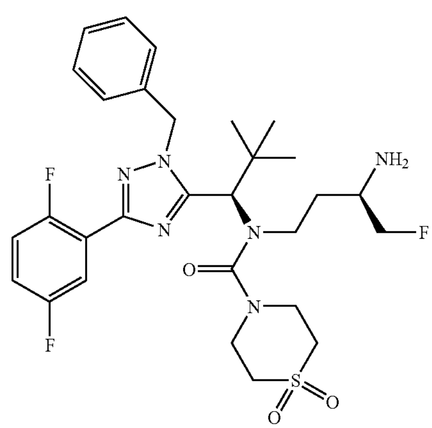 | 607.2 | N-((R)-3-amino-4-fluorobutyl)-N-((R)-1-(2-benzyl-5-(2,5-difluorophenyl)-2H-1,2,4-triazol-3-yl)-2,2-dimethylpropyl)-1,1-dioxothiomorpholine-4-carboxamide |

TABLE 1-continued

| Compound | Structure | MH+ | Name |
|---|---|---|---|
| 21 | 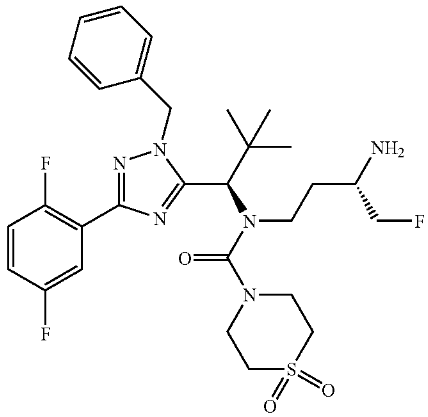 | 607.2 | N-((S)-3-amino-4-fluorobutyl)-N-((R)-1-(2-benzyl-5-(2,5-difluorophenyl)-2H-1,2,4-triazol-3-yl)-2,2-dimethylpropyl)-1,1-dioxothiomorpholine-4-carboxamide |
| 22 | 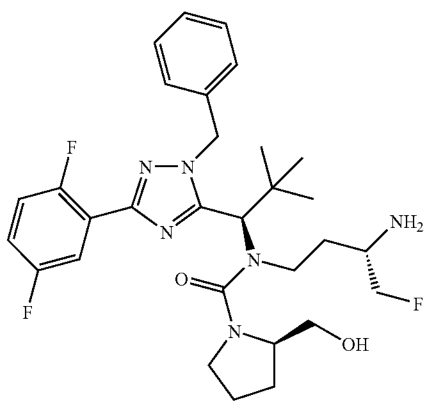 | 573.3 | (2R)-N-((S)-3-amino-4-fluorobutyl)-N-((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide |
| 23 | 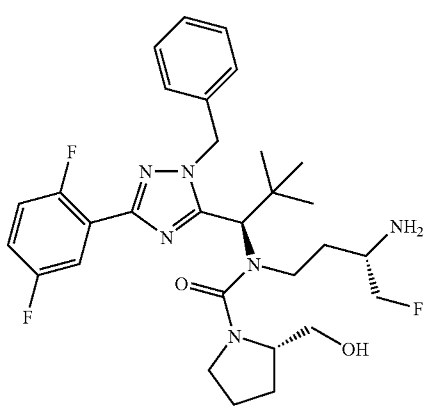 | 573.3 | (2S)-N-((S)-3-amino-4-fluorobutyl)-N-((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide |

TABLE 1-continued

| Compound | Structure | MH+ | Name |
|---|---|---|---|
| 24 | 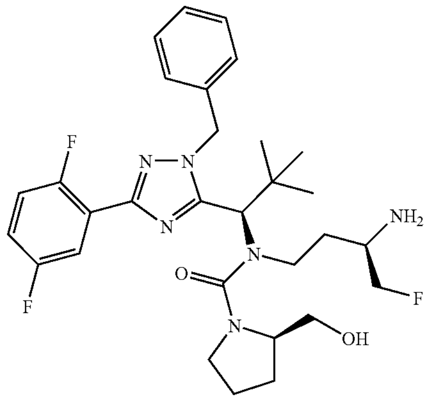 | 573.3 | (2R)-N-((R)-3-amino-4-fluorobutyl)-N-((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide |
| 25 | 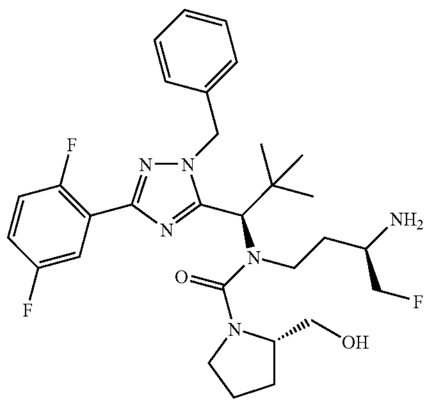 | 573.3 | (2S)-N-((R)-3-amino-4-fluorobutyl)-N-((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide |
| 26 | 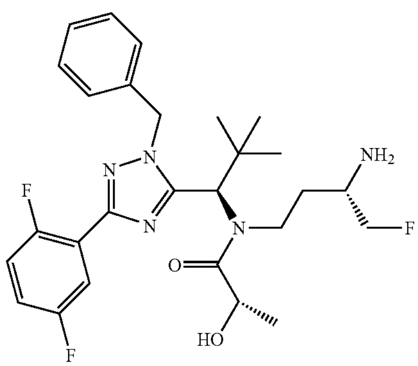 | 518.2 | (2S)-N-((S)-3-amino-4-fluorobutyl)-N-((R)-1-(2-benzyl-5-(2,5-difluorophenyl)-2H-1,2,4-triazol-3-yl)-2,2-dimethylpropyl)-2-hydroxypropanamide |
| 27 | 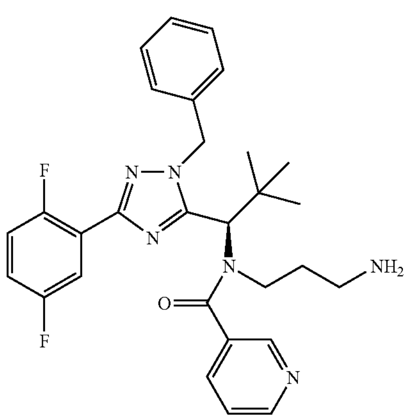 | 519.2 | N-(3-aminopropyl)-N-((R)-1-(2-benzyl-5-(2,5-difluorophenyl)-2H-1,2,4-triazol-3-yl)-2,2-dimethylpropyl)nicotinamide |

US 8,129,358 B2

TABLE 1-continued

| Compound | Structure | MH+ | Name |
|---|---|---|---|
| 28 | 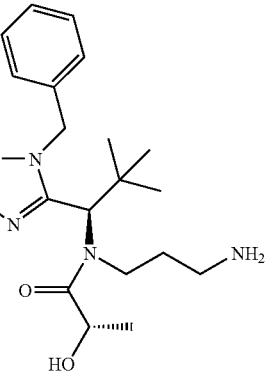 | 486.2 | (2S)-N-(3-aminopropyl)-N-((R)-1-(2-benzyl-5-(2,5-difluorophenyl)-2H-1,2,4-triazol-3-yl)-2,2-dimethylpropyl)-2-hydroxypropanamide |
| 29 | 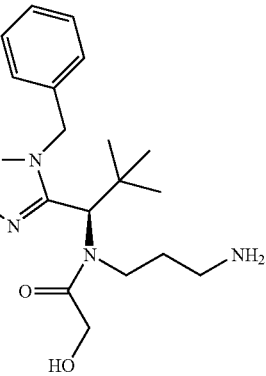 | 472.2 | N-(3-aminopropyl)-N-((R)-1-(2-benzyl-5-(2,5-difluorophenyl)-2H-1,2,4-triazol-3-yl)-2,2-dimethylpropyl)-2-hydroxyacetamide |
| 30 | 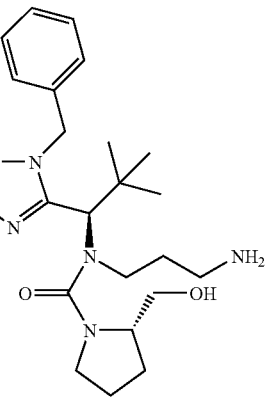 | 541.1 | (2S)-N-(3-aminopropyl)-N-((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide |
| 31 | 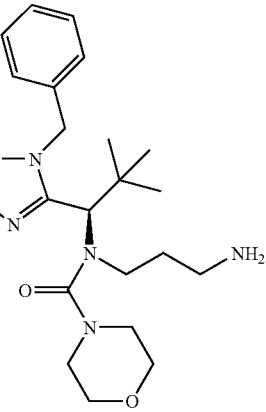 | 527.2 | N-(3-aminopropyl)-N-((R)-1-(2-benzyl-5-(2,5-difluorophenyl)-2H-1,2,4-triazol-3-yl)-2,2-dimethylpropyl)morpholine-4-carboxamide |

TABLE 1-continued

| Compound | Structure | MH+ | Name |
|---|---|---|---|
| 32 | 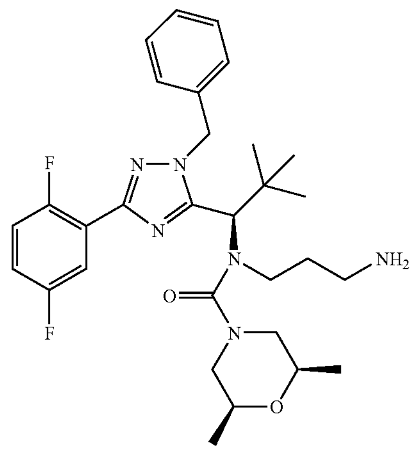 | 555.2 | (2S,6R)-N-(3-aminopropyl)-N-((R)-1-(2-benzyl-5-(2,5-difluorophenyl)-2H-1,2,4-triazol-3-yl)-2,2-dimethylpropyl)-2,6-dimethylmorpholine-4-carboxamide |
| 33 | 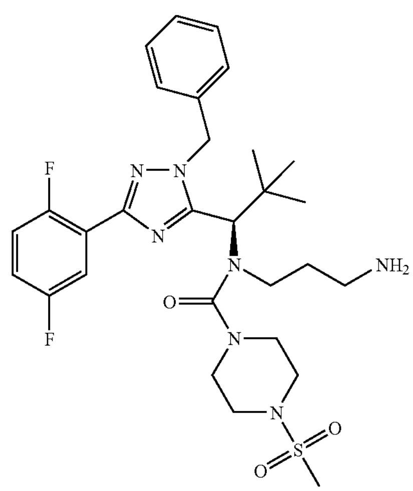 | 604.1 | N-(3-aminopropyl)-N-((R)-1-(2-benzyl-5-(2,5-difluorophenyl)-2H-1,2,4-triazol-3-yl)-2,2-dimethylpropyl)-4-(methylsulfonyl)piperazine-1-carboxamide |
| 34 | 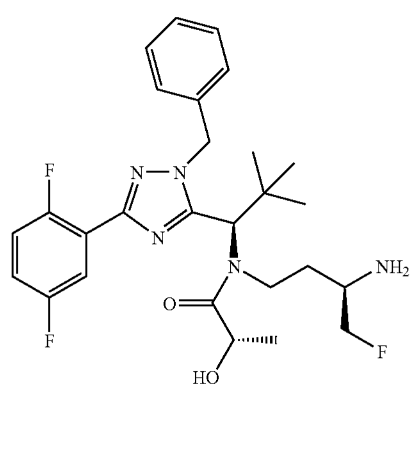 | 518.2 | (2S)-N-((R)-3-amino-4-fluorobutyl)-N-((R)-1-(2-benzyl-5-(2,5-difluorophenyl)-2H-1,2,4-triazol-3-yl)-2,2-dimethylpropyl)-2-hydroxypropanamide |

TABLE 1-continued

| Compound | MH+ | Name |
|---|---|---|
| 35 | 559.2 | (2S)-N-((S)-3-amino-2-fluoropropyl)-N-((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide |
| 36 | 573.2 | (2S,6R)-N-((S)-3-amino-2-fluoropropyl)-N-((R)-1-(2-benzyl-5-(2,5-difluorophenyl)-2H-1,2,4-triazol-3-yl)-2,2-dimethylpropyl)-2,6-dimethylmorpholine-4-carboxamide |
| 37 | 490.2 | N-((S)-3-amino-2-fluoropropyl)-N-((R)-1-(2-benzyl-5-(2,5-difluorophenyl)-2H-1,2,4-triazol-3-yl)-2,2-dimethylpropyl)-2-hydroxyacetamide |
| 38 | 544.2 | (2S)-N-((S)-3-amino-4-fluorobutyl)-N-((R)-1-(2-benzyl-5-(2,5-difluorophenyl)-2H-1,2,4-triazol-3-yl)-2,2-dimethylpropyl)-tetrahydrofuran-2-carboxamide |

TABLE 1-continued

| Compound | MH+ | Name |
|---|---|---|
| 39 | 544.2 | (2S)-N-((R)-3-amino-4-fluorobutyl)-N-((R)-1-(2-benzyl-5-(2,5-difluorophenyl)-2H-1,2,4-triazol-3-yl)-2,2-dimethylpropyl)-tetrahydrofuran-2-carboxamide |
| 40 | 565.2 | N-((S)-3-amino-4-fluorobutyl)-N-((R)-1-(2-benzyl-5-(2,5-difluorophenyl)-2H-1,2,4-triazol-3-yl)-2,2-dimethylpropyl)-6-methylpyridine-3-carboxamide |
| 41 | 551.2 | N-((S)-3-amino-4-fluorobutyl)-N-((R)-1-(2-benzyl-5-(2,5-difluorophenyl)-2H-1,2,4-triazol-3-yl)-2,2-dimethylpropyl)isonicotinamide |
| 42 | 551.2 | N-((S)-3-amino-4-fluorobutyl)-N-((R)-1-(2-benzyl-5-(2,5-difluorophenyl)-2H-1,2,4-triazol-3-yl)-2,2-dimethylpropyl)picolinamide |

TABLE 1-continued

| Compound | Structure | MH+ | Name |
|---|---|---|---|
| 43 | 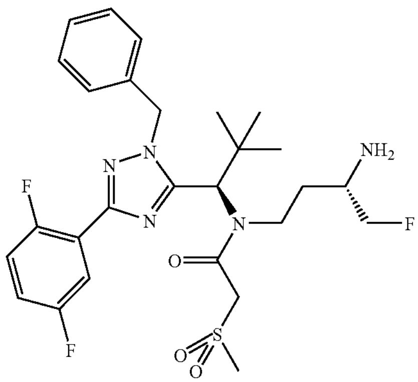 | 566.2 | N-((S)-3-amino-4-fluorobutyl)-N-((R)-1-(2-benzyl-5-(2,5-difluorophenyl)-2H-1,2,4-triazol-3-yl)-2,2-dimethylpropyl)-2-(methylsulfonyl)acetamide |
| 44 | 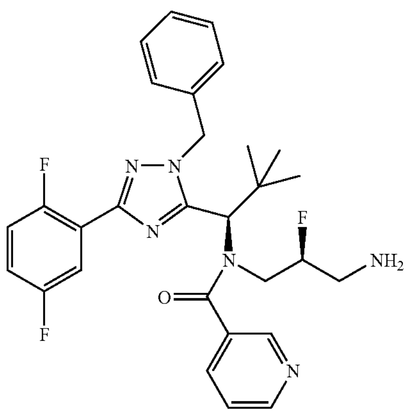 | 537.2 | N-((S)-3-amino-2-fluoropropyl)-N-((R)-1-(2-benzyl-5-(2,5-difluorophenyl)-2H-1,2,4-triazol-3-yl)-2,2-dimethylpropyl)nicotinamide |
| 45 | 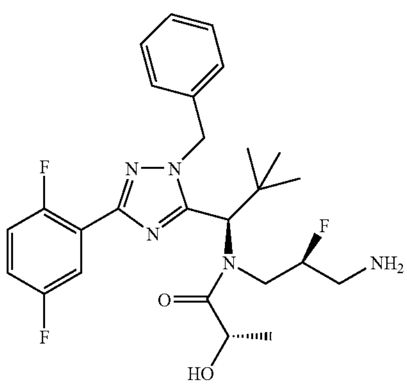 | 504.2 | (2S)-N-((S)-3-amino-2-fluoropropyl)-N-((R)-1-(2-benzyl-5-(2,5-difluorophenyl)-2H-1,2,4-triazol-3-yl)-2,2-dimethylpropyl)-2-hydroxypropanamide |
| 46 | 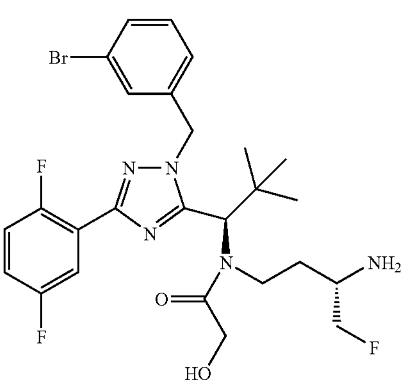 | 582.2 | N-((R)-1-(2-(3-bromobenzyl)-5-(2,5-difluorophenyl)-2H-1,2,4-triazol-3-yl)-2,2-dimethylpropyl)-N-((S)-3-amino-4-fluorobutyl)-2-hydroxyacetamide |

TABLE 1-continued

| Compound | Structure | MH+ | Name |
|---|---|---|---|
| 47 | 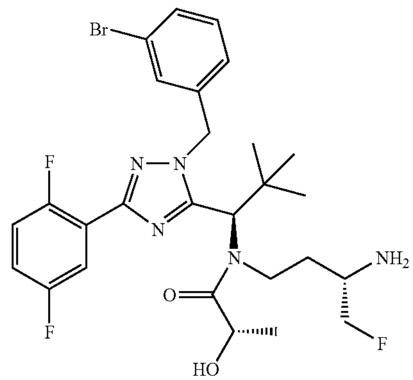 | 596.2 | (2S)-N-((R)-1-(2-(3-bromobenzyl)-5-(2,5-difluorophenyl)-2H-1,2,4-triazol-3-yl)-2,2-dimethylpropyl)-N-((S)-3-amino-4-fluorobutyl)-2-hydroxypropanamide |
| 48 | 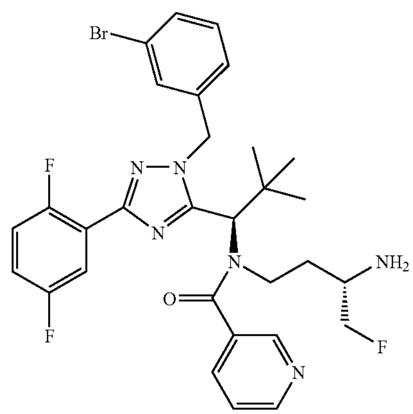 | 629.2 | N-((R)-1-(2-(3-bromobenzyl)-5-(2,5-difluorophenyl)-2H-1,2,4-triazol-3-yl)-2,2-dimethylpropyl)-N-((S)-3-amino-4-fluorobutyl)nicotinamide |
| 49 | 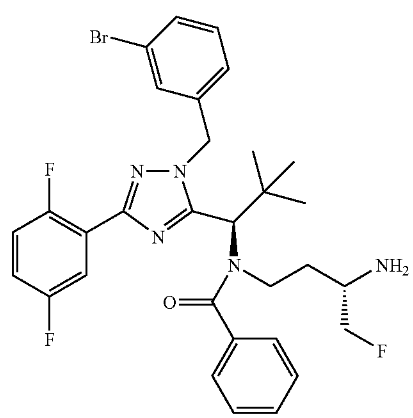 | 628.2 | N-((R)-1-(2-(3-bromobenzyl)-5-(2,5-difluorophenyl)-2H-1,2,4-triazol-3-yl)-2,2-dimethylpropyl)-N-((S)-3-amino-4-fluorobutyl)benzamide |
| 50 | 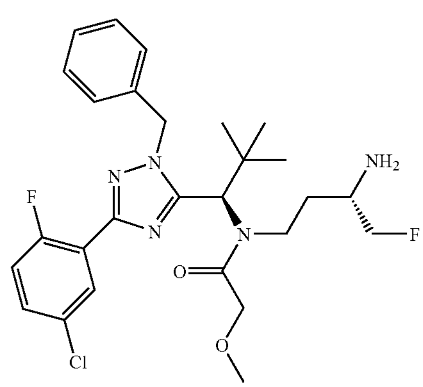 | 550.2 | N-((S)-3-amino-4-fluorobutyl)-N-((R)-1-(2-benzyl-5-(5-chloro-2-fluorophenyl)-2H-1,2,4-triazol-3-yl)-2,2-dimethylpropyl)-2-methoxyacetamide |

TABLE 1-continued

| Compound | Structure | MH+ | Name |
| --- | --- | --- | --- |
| 51 | 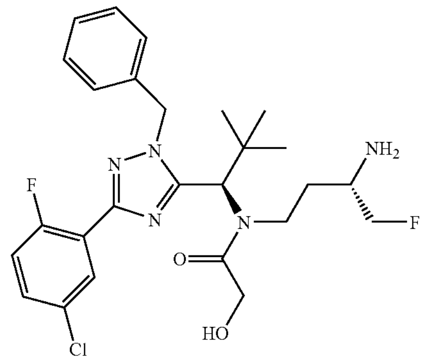 | 520.2 | N-((S)-3-amino-4-fluorobutyl)-N-((R)-1-(2-benzyl-5-(5-chloro-2-fluorophenyl)-2H-1,2,4-triazol-3-yl)-2,2-dimethylpropyl)-2-hydroxyacetamide |
| 52 | 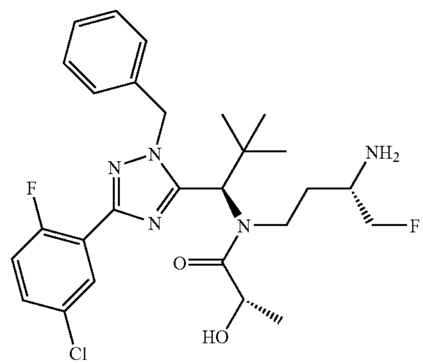 | 534.2 | (S)-N-((S)-3-amino-4-fluorobutyl)-N-((R)-1-(1-benzyl-2-(5-chloro-2-fluorophenyl)-1H-1,2,4-triazol-5-yl)-2,2-dimethylpropyl)-2-hydroxypropanamide |
| 53 | 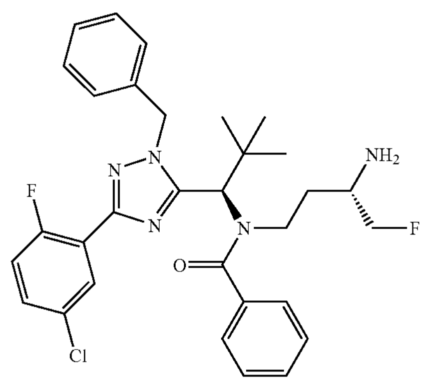 | 566.2 | N-((S)-3-amino-4-fluorobutyl)-N-((R)-1-(1-benzyl-3-(5-chloro-2-fluorophenyl)-1H-1,2,4-triazol-5-yl)-2,2-dimethylpropyl)benzamide |
| 54 | 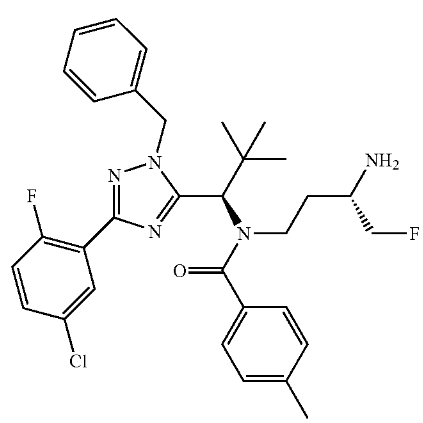 | 580.3 | N-((S)-3-amino-4-fluorobutyl)-N-((R)-1-(1-benzyl-3-(5-chloro-2-fluorophenyl)-1H-1,2,4-triazol-5-yl)-2,2-dimethylpropyl)-4-methylbenzamide |

TABLE 1-continued

| Compound | Structure | MH+ | Name |
|---|---|---|---|
| 55 | 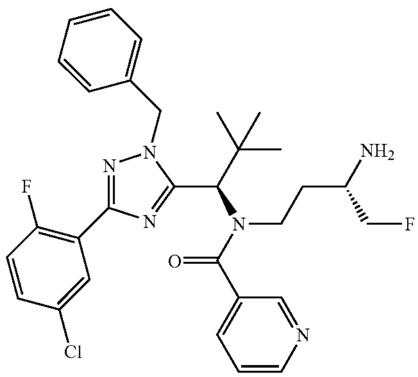 | 567.2 | N-((S)-3-amino-4-fluorobutyl)-N-((R)-1-(1-benzyl-3-(5-chloro-2-fluorophenyl)-1H-1,2,4-triazol-5-yl)-2,2-dimethylpropyl)nicotinamide |
| 56 | 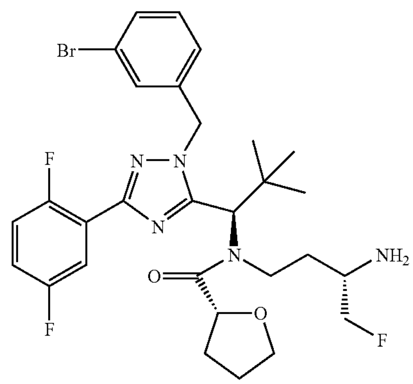 | 622.2 | (R)-N-((S)-3-amino-4-fluorobutyl)-N-((R)-1-(1-(3-bromobenzyl)-3-(2,5-difluorophenyl)-1H-1,2,4-triazol-5-yl)-2,2-dimethylpropyl)tetrahydrofuran-2-carboxamide |
| 57 | 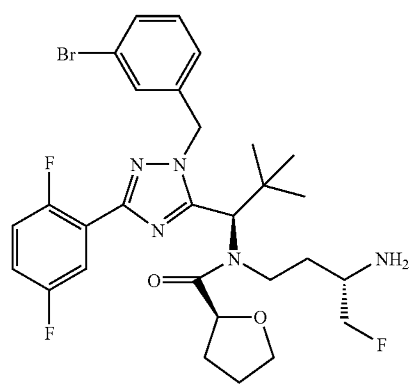 | 622.2 | (S)-N-((S)-3-amino-4-fluorobutyl)-N-((R)-1-(1-(3-bromobenzyl)-3-(2,5-difluorophenyl)-1H-1,2,4-triazol-5-yl)-2,2-dimethylpropyl)tetrahydrofuran-2-carboxamide |
| 58 | 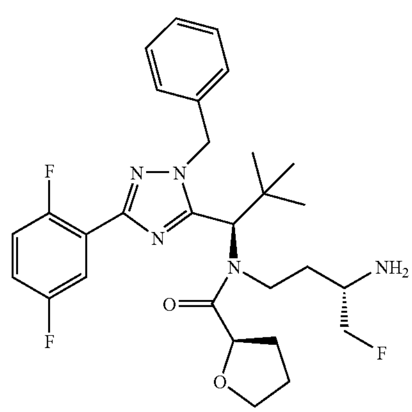 | 544.3 | (R)-N-((S)-3-amino-4-fluorobutyl)-N-((R)-1-(1-benzyl-3-(2,5-difluorophenyl)-1H-1,2,4-triazol-5-yl)-2,2-dimethylpropyl)tetrahydrofuran-2-carboxamide |

TABLE 1-continued

| Compound | Structure | MH+ | Name |
|---|---|---|---|
| 59 | 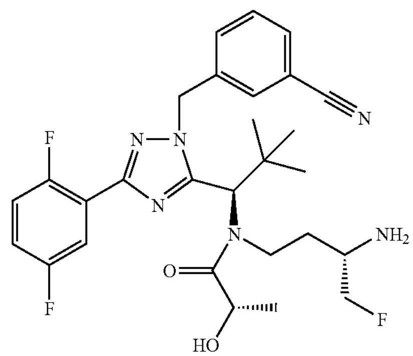 | 543.3 | (S)-N-((S)-3-amino-4-fluorobutyl)-N-((R)-1-(1-(3-cyanobenzyl)-3-(2,5-difluorophenyl)-1H-1,2,4-triazol-5-yl)-2,2-dimethylpropyl)-2-hydroxypropanamide |
| 60 | 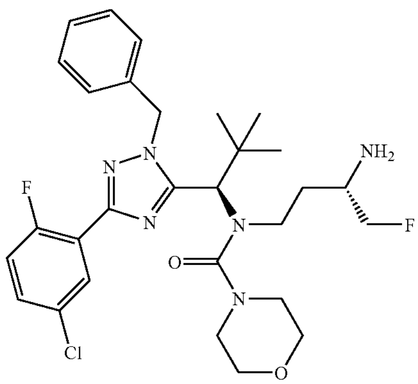 | 575.3 | N-((S)-3-amino-4-fluorobutyl)-N-((R)-1-(1-benzyl-3-(5-chloro-2-fluorophenyl)-1H-1,2,4-triazol-5-yl)-2,2-dimethylpropyl)morpholine-4-carboxamide |
| 61 | 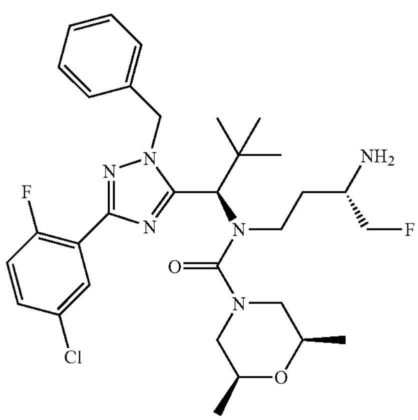 | 603.3 | (2S,6R)-N-((S)-3-amino-4-fluorobutyl)-N-((R)-1-(1-benzyl-3-(5-chloro-2-fluorophenyl)-1H-1,2,4-triazol-5-yl)-2,2-dimethylpropyl)-2,6-dimethylmorpholine-4-carboxamide |
| 62 | 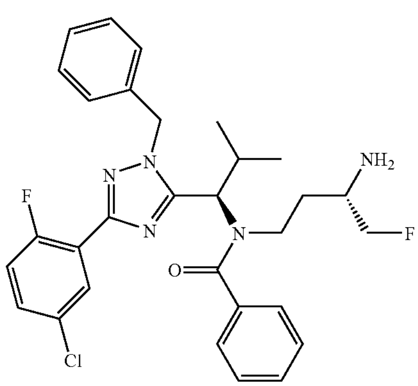 | 552.2 | N-((S)-3-amino-4-fluorobutyl)-N-((R)-1-(1-benzyl-3-(5-chloro-2-fluorophenyl)-1H-1,2,4-triazol-5-yl)-2-methylpropyl)benzamide |

TABLE 1-continued

| Compound | Structure | MH+ | Name |
|---|---|---|---|
| 63 | 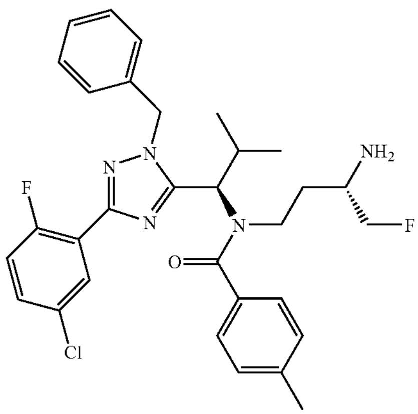 | 566.2 | N-((S)-3-amino-4-fluorobutyl)-N-((R)-1-(1-benzyl-3-(5-chloro-2-fluorophenyl)-1H-1,2,4-triazol-5-yl)-2-methylpropyl)-4-methylbenzamide |
| 64 | 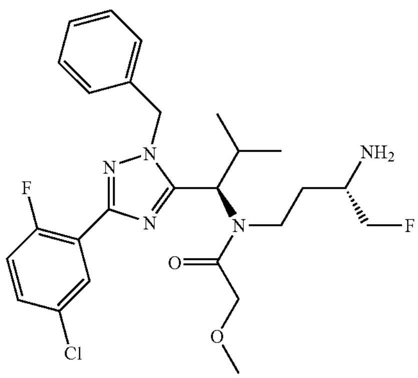 | 520.2 | N-((S)-3-amino-4-fluorobutyl)-N-((R)-1-(1-benzyl-3-(5-chloro-2-fluorophenyl)-1H-1,2,4-triazol-5-yl)-2-methylpropyl)-2-methoxyacetamide |
| 65 | 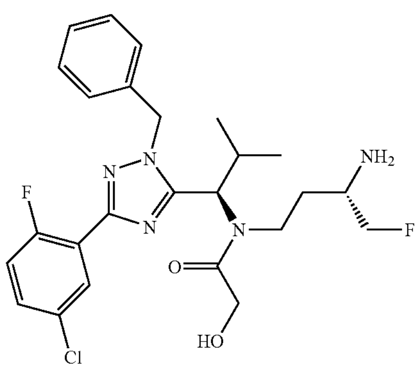 | 506.2 | N-((S)-3-amino-4-fluorobutyl)-N-((R)-1-(1-benzyl-3-(5-chloro-2-fluorophenyl)-1H-1,2,4-triazol-5-yl)-2-methylpropyl)-2-hydroxyacetamide |
| 66 | 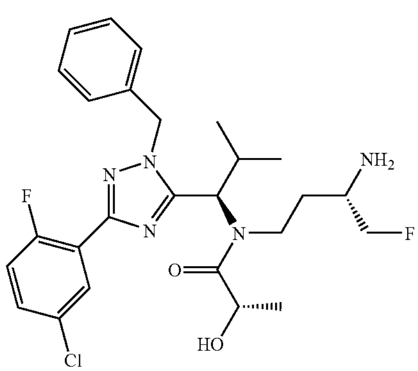 | 520.2 | (S)-N-((S)-3-amino-4-fluorobutyl)-N-((R)-1-(1-benzyl-3-(5-chloro-2-fluorophenyl)-1H-1,2,4-triazol-5-yl)-2-methylpropyl)-2-hydroxypropanamide |

TABLE 1-continued

| Compound | Structure | MH+ | Name |
|---|---|---|---|
| 67 | 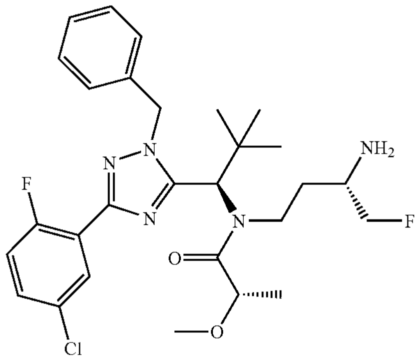 | 532.3 | (S)-N-((S)-3-amino-4-fluorobutyl)-N-((R)-1-(1-benzyl-3-(2,5-difluorophenyl)-1H-1,2,4-triazol-5-yl)-2,2-dimethylpropyl)-2-methoxypropanamide |
| 68 | 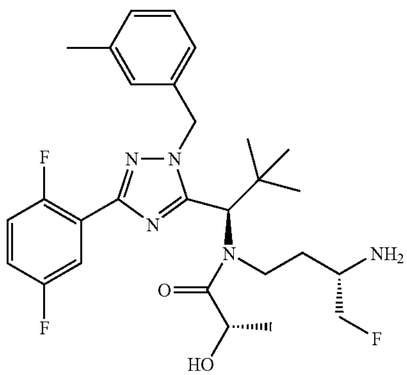 | 532.3 | (S)-N-((S)-3-amino-4-fluorobutyl)-N-((R)-1-(3-(2,5-difluorophenyl)-1-(3-methylbenzyl)-1H-1,2,4-triazol-5-yl)-2,2-dimethylpropyl)-2-hydroxypropanamide |
| 69 | 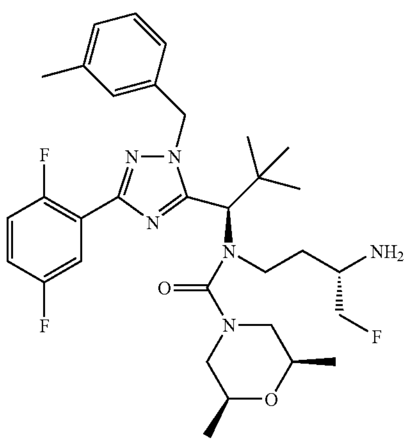 | 601.3 | (2S,6R)-N-((S)-3-amino-4-fluorobutyl)-N-((R)-1-(3-(2,5-difluorophenyl)-1-(3-methylbenzyl)-1H-1,2,4-triazol-5-yl)-2,2-dimethylpropyl)-2,6-dimethylmorpholine-4-carboxamide |
| 70 | 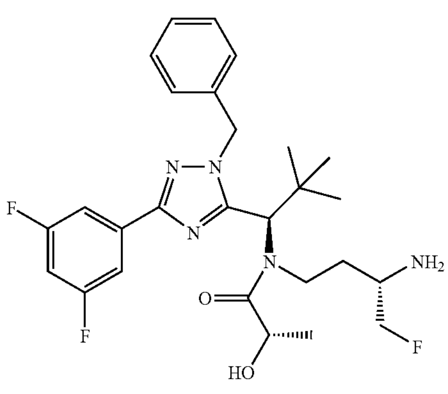 | 518.3 | (S)-N-((S)-3-amino-4-fluorobutyl)-N-((R)-1-(1-benzyl-3-(3,5-difluorophenyl)-1H-1,2,4-triazol-5-yl)-2,2-dimethylpropyl)-2-hydroxypropanamide |

TABLE 1-continued

| Compound | MH+ | Name |
|---|---|---|
| 71 | 550.2 | (S)-N-((S)-3-amino-4-fluorobutyl)-N-((R)-1-(1-benzyl-3-(3,5-dichlorophenyl)-1H-1,2,4-triazol-5-yl)-2,2-dimethylpropyl)-2-hydroxypropanamide |
| 72 | 587.3 | (2S,6R)-N-((S)-3-amino-4-fluorobutyl)-N-((R)-1-(1-benzyl-3-(3,5-difluorophenyl)-1H-1,2,4-triazol-5-yl)-2,2-dimethylpropyl)-2,6-dimethylmorpholine-4-carboxamide |
| 73 | 536.3 | (S)-N-((S)-3-amino-4,4-difluorobutyl)-N-((R)-1-(1-benzyl-3-(2,5-difluorophenyl)-1H-1,2,4-triazol-5-yl)-2,2-dimethylpropyl)-2-hydroxypropanamide |
| 74 | 536.3 | (S)-N-((R)-3-amino-4,4-difluorobutyl)-N-((R)-1-(1-benzyl-3-(2,5-difluorophenyl)-1H-1,2,4-triazol-5-yl)-2,2-dimethylpropyl)-2-hydroxypropanamide |

TABLE 1-continued

| Compound | Structure | MH+ | Name |
|---|---|---|---|
| 75 | 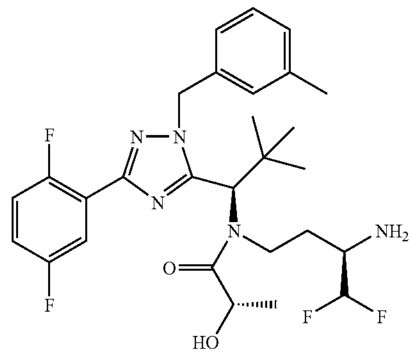 | 550.3 | (S)-N-((R)-3-amino-4,4-difluorobutyl)-N-((R)-1-(3-(2,5-difluorophenyl)-1-(3-methylbenzyl)-1H-1,2,4-triazol-5-yl)-2,2-dimethylpropyl)-2-hydroxypropanamide |
| 76 | 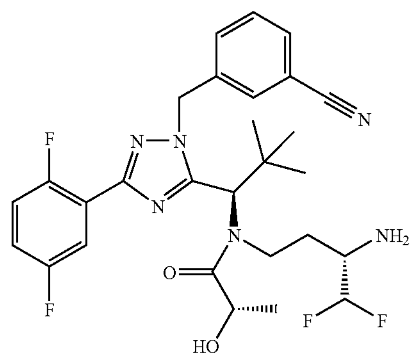 | 561.2 | (S)-N-((S)-3-amino-4,4-difluorobutyl)-N-((R)-1-(1-(3-cyanobenzyl)-3-(2,5-difluorophenyl)-1H-1,2,4-triazol-5-yl)-2,2-dimethylpropyl)-2-hydroxypropanamide |
| 77 | 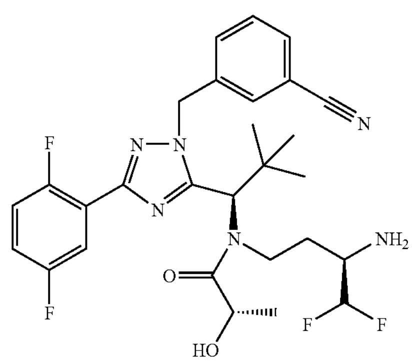 | 561.2 | (S)-N-((R)-3-amino-4,4-difluorobutyl)-N-((R)-1-(1-(3-cyanobenzyl)-3-(2,5-difluorophenyl)-1H-1,2,4-triazol-5-yl)-2,2-dimethylpropyl)-2-hydroxypropanamide |
| 78 | 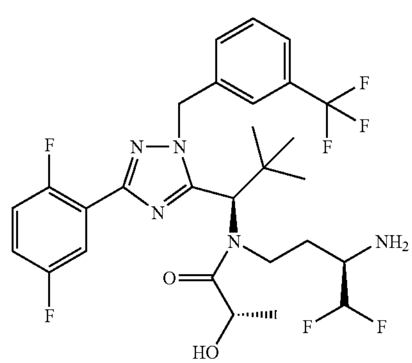 | 604.2 | (S)-N-((R)-3-amino-4,4-difluorobutyl)-N-((R)-1-(3-(2,5-difluorophenyl)-1-(3-(trifluoromethyl)benzyl)-1H-1,2,4-triazol-5-yl)-2,2-dimethylpropyl)-2-hydroxypropanamide |

TABLE 1-continued

| Compound | Structure | MH+ | Name |
|---|---|---|---|
| 79 | 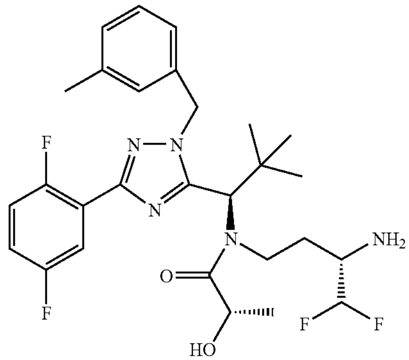 | 550.3 | (S)-N-((S)-3-amino-4,4-difluorobutyl)-N-((R)-1-(3-(2,5-difluorophenyl)-1-(3-methylbenzyl)-1H-1,2,4-triazol-5-yl)-2,2-dimethylpropyl)-2-hydroxypropanamide |
| 80 | 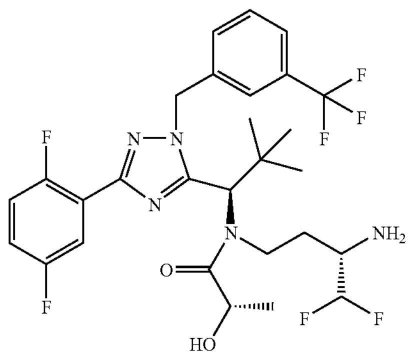 | 604.2 | (S)-N-((S)-3-amino-4,4-difluorobutyl)-N-((R)-1-(3-(2,5-difluorophenyl)-1-(3-(trifluoromethyl)benzyl)-1H-1,2,4-triazol-5-yl)-2,2-dimethylpropyl)-2-hydroxypropanamide |
| 81 | 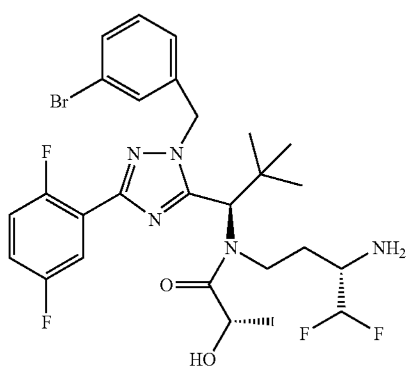 | 614.2 | (S)-N-((S)-3-amino-4,4-difluorobutyl)-N-((R)-1-(1-(3-bromobenzyl)-3-(2,5-difluorophenyl)-1H-1,2,4-triazol-5-yl)-2,2-dimethylpropyl)-2-hydroxypropanamide |
| 82 | 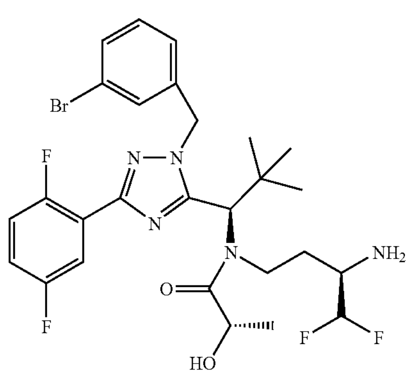 | 614.2 | (S)-N-((R)-3-amino-4,4-difluorobutyl)-N-((R)-1-(1-(3-bromobenzyl)-3-(2,5-difluorophenyl)-1H-1,2,4-triazol-5-yl)-2,2-dimethylpropyl)-2-hydroxypropanamide |

TABLE 1-continued

| Compound | Structure | MH+ | Name |
|---|---|---|---|
| 83 | 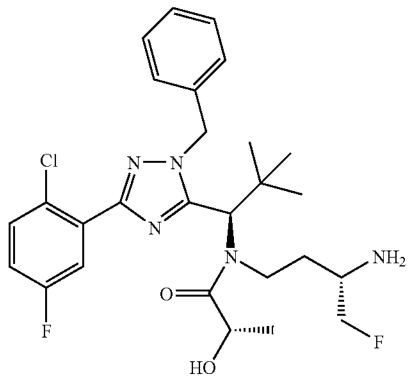 | 534.2 | (S)-N-((S)-3-amino-4-fluorobutyl)-N-((R)-1-(1-benzyl-3-(2-chloro-5-fluorophenyl)-1H-1,2,4-triazol-5-yl)-2,2-dimethylpropyl)-2-hydroxypropanamide |
| 84 | 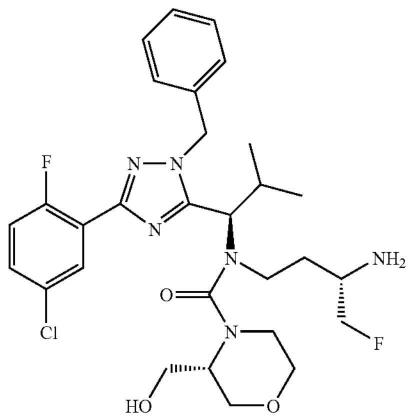 | 591.3 | (S)-N-((S)-3-amino-4-fluorobutyl)-N-((R)-1-(1-benzyl-3-(5-chloro-2-fluorophenyl)-1H-1,2,4-triazol-5-yl)-2-methylpropyl)-3-(hydroxymethyl)morpholine-4-carboxamide |
| 85 | 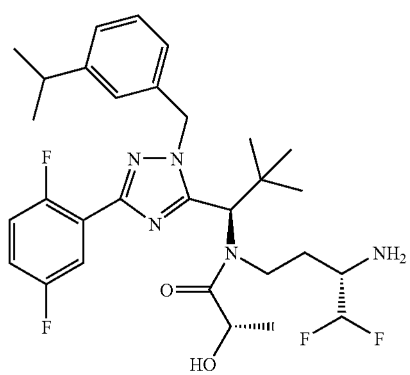 | 578.3 | (S)-N-((S)-3-amino-4,4-difluorobutyl)-N-((R)-1-(3-(2,5-difluorophenyl)-1-(3-isopropylbenzyl)-1H-1,2,4-triazol-5-yl)-2,2-dimethylpropyl)-2-hydroxypropanamide |
| 86 | 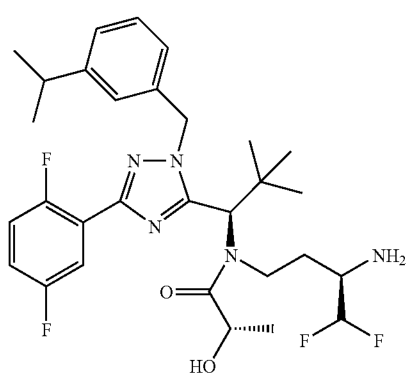 | 578.3 | (S)-N-((R)-3-amino-4,4-difluorobutyl)-N-((R)-1-(3-(2,5-difluorophenyl)-1-(3-isopropylbenzyl)-1H-1,2,4-triazol-5-yl)-2,2-dimethylpropyl)-2-hydroxypropanamide |

Example 12

Assay for Determining KSP Activity

This example provides a representative in vitro assay for determining KSP activity in vitro. Purified microtubules obtained from bovine brain were purchased from Cytoskeleton Inc. (Denver, Colo., USA). The motor domain of human KSP (Eg 5, KNSL1) was cloned, expressed, and purified to greater than 95% homogeneity. Biomol Green was purchased from Affinity Research Products Ltd. (Matford Court, Exeter, Devon, United Kingdom). Microtubules and KSP motor protein (i.e., the KSP motor domain) were diluted in assay buffer (20 mM Tris-HCl (pH 7.5), 1 mM $MgCl_2$, 10 mM DTT and 0.25 mg/mL BSA) to a final concentration of 35 µg/mL microtubules and 45 nM KSP. The microtubule/KSP mixture was then pre-incubated at 37° C. for 10 min to promote the binding of KSP to microtubules.

To each well of the testing plate (384-well plate) containing 1.25 µL of inhibitor or test compound in DMSO (or DMSO only in the case of controls) were added 25 µL of ATP solution (ATP diluted to a concentration of 300 µM in assay buffer) and 25 µL of the above-described microtubule/KSP solution. The plates were incubated at RT for 1 hour. Following incubation, 65 µL of Biomol Green (a malachite green-based dye that detects the release of inorganic phosphate) was added to each well. The plates were incubated for an additional 5-10 minutes then the absorbance at 630 nm was determined using a Victor II plate reader. The amount of absorbance at 630 nm corresponded to the amount of KSP activity in the samples. The $IC_{50}$ of each inhibitor or test compound was then determined based on the decrease in absorbance at 630 nm at each concentration, via nonlinear regression using either XLFit for Excel or Prism data analysis software by GraphPad Software Inc.

Preferred compounds of the invention have a biological activity as measured by an $IC_{50}$ of less than about 1 mM in assay protocols described in Example 12, with preferred embodiments having biological activity of less than about 25 µM, with particularly preferred embodiments having biological activity of less than about 1000 nM, and with the most preferred embodiments having biological activity of less than about 100 nM.

When tested the this assay, Compounds 71, 85 and 86 in Table 1 exhibited $IC_{50}$ values greater than 1 µM. Compounds 77, 78, and 80 exhibited $IC_{50}$ values greater than 100 nM and less than or equal to 1 µM. Compounds 1-15, 18-70, 72-76, 79, and 81-84 in Table 1 exhibited $IC_{50}$ values less than or equal to 100 nM.

Example 13

Inhibition of Cellular Proliferation in Tumor Cell Lines Treated with KSP Inhibitors Cells are plated in 96-well plates at densities of about 500 cells per well of a 96-well plate and are allowed to grow for 24 hours. The cells are then treated with various concentrations of compounds for 72 hours. Then, 100 µl of CellTiter Glo is added. CellTiter Glo is a tetrazolium-based assay using the reagent 3-(4,5-dimethylthiazol-2-yl) 5-(3-carboxymethoxyphenyl)-2-(4-sulfophenyl)-2H-tetrazolium (MTS) (U.S. Pat. No. 5,185,450) (see Promega product catalog #G3580, CellTiter 96 Aqueous One Solution Cell Proliferation Assay). The cells are then incubated in the dark for 30 minutes. The amount of luminescence is determined for each well using a Walloc Trilux plate reader, which correlates with the number of cells per well. The number of viable cells in the wells that receive only DMSO (0.5%) serve as an indication of 0% inhibition, while wells without cells serve as 100% inhibition of cell growth. The compound concentration that results in a 50% growth inhibition ($GI_{50}$) is determined graphically from sigmoidal dose-response curves of log-transformed dose values versus cell counts (percent of control) at 72 hours of continuous compound exposure.

The cell lines used are listed below.

The cell proliferation assay is performed as described above.

Cancer Cell Lines
Colo 205—colon carcinoma
    RPMI 1640+10% FBS+1% L-glutamine+1% P/S+1% NaPyr.+Hepes
    +4.5 g/L Glucose+1% NaBicarb.
MDA 435—breast cancer—high met
    EMEM+10% FBS+1% P/S+1% L-Glutamine+1% NEAA+1% NaPyr+1% vitamins
HCT-15 and HCT116—colon carcinoma
    RPMI 1640+10% FBS+1% L-glutamine+1% P/S
Drug Resistant Cell Lines
KB3.1—colon epidermal carcinoma; parental cell line
    Iscove's+10% FBS+1% L-glutamine+1% P/S
KBV1—p-glycoprotein associated multi-drug resistant cell line
    RPMI 1640+10% FBS+1% L-glutamine+1% P/S+0.2 ug/mL Vinblastine
KB85—p-glycoprotein associated multi-drug resistant cell line DMEM+10% FBS+1% L-glutamine+1% P/S+ 10 ng/mL Colchicine Preferred compounds of the invention have a biological activity as measured by an GI50 of less than about 1 mM in assay protocols described with some embodiments having biological activity of less than about 25 µM, with other embodiments having biological activity of less than about 1000 nM, and with still other embodiment having a GI50 of less than about 100 nM.

Example 14

Clonogenic Softagar Assay Protocol

Human cancer cells are plated at a density of $3 \times 10^5$ cells per well in a 6-well plate. The next day, a compound of interest at a certain concentration is added to each well. After 24 and 48 hours of incubation, the cells are harvested, washed and counted. The following steps are performed using the Multimek 96 robot. Then, 500 viable cells per well are plated in a 96-well plate that is coated with PolyHema to prevent attachment of the cells to the bottom of the well. Agarose (3% stock) is melted, diluted in warmed media and added to the cells to a final concentration of 0.5%. After the soft agar solidified, the plates are incubated at 37° C. for 6 days.

Alamar blue dye is added to cells and plates are incubated for an additional 6 hours. The optical density change is measured on a Tecan plate reader and is considered to correlate with the number of colonies formed in soft agar. A cancerous cell is able to grow on the agar and thus will show an increase in optical density. A reading of decreased optical density means that the cancer cells are being inhibited. It is contemplated that compounds of this invention will exhibit a decrease in optical density.

What is claimed is:

1. A compound of Formula (I) or a pharmaceutically acceptable salt, ester, or prodrug thereof:

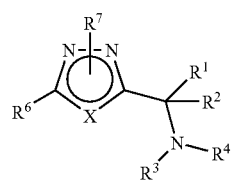

(I)

wherein:
$R^1$ is selected from the group consisting of alkyl and substituted alkyl;
$R^2$ is selected from the group consisting of hydrogen, alkyl, and substituted alkyl;
$R^3$ is selected from the group consisting of -$L^1$-$A^1$, wherein $L^1$ is selected from the group consisting of —C(O)—, —C(S)—, —S(O)—, and —S(O)$_2$— and $A^1$ is selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, substituted heterocycloalkyl, and $NR^8R^9$;
$R^4$ is selected from the group consisting of hydrogen, alkyl, substituted alkyl, alkenyl, substituted alkenyl, alkynyl, and substituted alkynyl;
or $R^3$ and $R^4$ together with the nitrogen atom bound thereto join to form a five to seven membered heterocycloalkyl or substituted heterocycloalkyl group where optionally one additional ring atom is selected from the group consisting of O, S, or $NR^{11}$;
X is $CR^5$ or N;
$R^5$ is selected from the group consisting of hydrogen, halo, alkyl, and substituted alkyl;
$R^6$ is selected from the group consisting of cycloalkyl, heterocycloalkyl, aryl, and heteroaryl, all of which may be optionally substituted with)-$(R^{10})_m$ where $R^{10}$ is as defined herein, m is 1, 2, 3, or 4, and each $R^{10}$ may be the same or different when m is 2, 3, or 4;
$R^7$ is -$L^2$-$A^2$ wherein $L^2$ is $C_1$-$C_5$ alkylene and $A^2$ is selected from the group consisting of aryl, substituted aryl, heteroaryl, substituted heteroaryl, cycloalkyl, substituted cycloalkyl, heterocycloalkyl, and substituted heterocycloalkyl, provided that $R^7$ is not attached to X;
$R^8$ is selected from the group consisting of hydrogen and alkyl;
$R^9$ is selected from the group consisting of hydrogen, hydroxy, alkyl, substituted alkyl, aryl, substituted aryl, heteroaryl, substituted heteroaryl, cycloalkyl, substituted cycloalkyl, heterocycloalkyl, and substituted heterocycloalkyl;
or $R^8$ and $R^9$ together with the nitrogen atom pendent thereto join to form a heterocycloalkyl or substituted heterocycloalkyl;
$R^{10}$ is selected from the group consisting of cyano, alkyl, substituted alkyl, alkenyl, substituted alkenyl, alkynyl, substituted alkynyl, —$CF_3$, alkoxy, substituted alkoxy, halo, and hydroxy; and
$R^{11}$ is selected from the group consisting of hydrogen, alkyl, substituted alkyl, —$SO_2$alkyl, and —$SO_2$ substituted alkyl.

2. A compound of claim 1, wherein $R^2$ is alkyl.

3. A compound of claim 2, wherein $R^2$ is methyl.

4. A compound of claim 1, wherein $R^1$ and $R^2$ are methyl.

5. A compound of claim 1, having Formula (Ia)-(Ie) or a pharmaceutically acceptable salt, ester, or prodrug thereof:

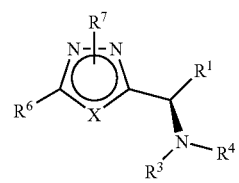

(Ia)

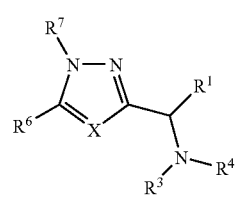

(Ib)

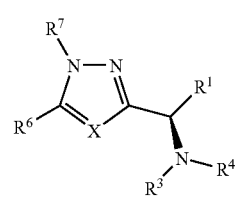

(Ic)

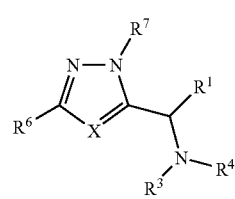

(Id)

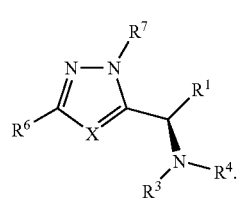

(Ie)

6. A compound of claim 1 or 5, wherein X is N.

7. A compound of claim 1 or 5, wherein X is $CR^5$.

8. A compound of claim 7, wherein R⁵ is hydrogen.

9. A compound of claim 1, wherein L¹ is —CO—.

10. A compound of claim 1, having Formula (II) or a pharmaceutically acceptable salt, ester, or prodrug thereof:

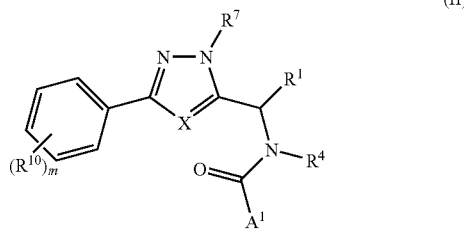

(II)

wherein:
R¹ is selected from the group consisting of alkyl and substituted alkyl;
R⁴ is alkyl substituted with one to five substituents selected from the group consisting of hydroxy, alkoxy, substituted alkoxy, amino, substituted amino, acylamino, halo, nitrogen-containing heterocycloalkyl, substituted nitrogen-containing heterocycloalkyl, nitrogen-containing heteroaryl, and substituted nitrogen-containing heteroaryl;
A¹ is selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, substituted heterocycloalkyl, and NR⁸R⁹;
or A¹ and R⁴ together with the atoms bound respectively thereto join to form a heterocycloalkyl or substituted heterocycloalkyl group where optionally one additional ring atom is selected from the group consisting of O, S, or NR¹¹;
X is CR⁵ or N;
R⁵ is selected from the group consisting of hydrogen, halo, alkyl, and substituted alkyl;
R⁷ is -L²-A² wherein L² is C₁-C₅ alkylene and A² is selected from the group consisting of aryl, substituted aryl, heteroaryl, substituted heteroaryl, cycloalkyl, substituted cycloalkyl, heterocycloalkyl, and substituted heterocycloalkyl;
R⁸ is selected from the group consisting of hydrogen and alkyl;
R⁹ is selected from the group consisting of hydrogen, hydroxy, alkyl, substituted alkyl, aryl, substituted aryl, heteroaryl, substituted heteroaryl, cycloalkyl, substituted cycloalkyl, heterocycloalkyl, and substituted heterocycloalkyl;
or R⁸ and R⁹ together with the nitrogen atom pendent thereto join to form a heterocycloalkyl or substituted heterocycloalkyl;
m is 1, 2, 3, or 4, and each R¹⁰ may be the same or different when m is 2, 3, or 4; and
R¹⁰ is selected from the group consisting of cyano, alkyl, substituted alkyl, alkenyl, substituted alkenyl, alkynyl, substituted alkynyl, —CF₃, alkoxy, substituted alkoxy, halo, and hydroxy; and
R¹¹ is selected from the group consisting of hydrogen, alkyl, substituted alkyl, —SO₂alkyl, and —SO₂ substituted alkyl.

11. A compound of claim 10, wherein X is N.

12. A compound of claim 10, wherein X is CR⁵.

13. A compound of claim 12, wherein R⁵ is hydrogen.

14. A compound of claim 10, having Formula (IIa) or a pharmaceutically acceptable salt, ester, or prodrug thereof:

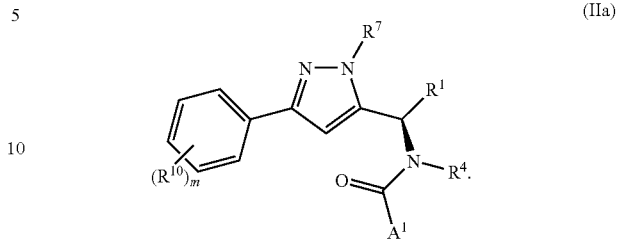

(IIa)

15. A compound of claim 10, having Formula (IIb) or a pharmaceutically acceptable salt, ester, or prodrug thereof:

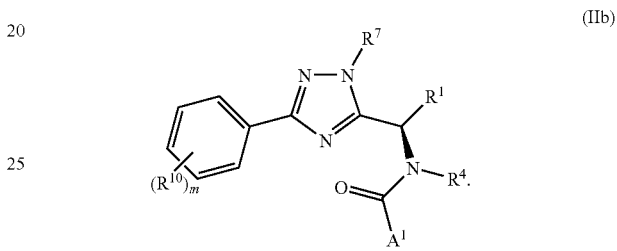

(IIb)

16. A compound according to any one of claims 1, 5, or 10, wherein R¹ is alkyl.

17. A compound of claim 16 wherein R¹ is selected from the group consisting of isopropyl, t-butyl, and propyl.

18. A compound according to any one of claims 1, 5, or 10, wherein A¹ is aryl or substituted aryl.

19. A compound of claim 18, wherein A¹ is substituted or unsubstituted phenyl.

20. A compound according to any one of claims 1, 5, or 10, wherein A¹ is heteroaryl or substituted heteroaryl.

21. A compound of claim 20, wherein A¹ is substituted or unsubstituted pyridyl.

22. A compound according to any one of claims 1, 5, or 10, wherein A¹ is heterocycloalkyl or substituted heterocycloalkyl.

23. A compound of claim 22, wherein A¹ is substituted or unsubstituted morpholino.

24. A compound according to any one of claims 1, 5, or 10, wherein A¹ is alkyl or substituted alkyl.

25. A compound of claim 24, wherein said substituted alkyl is substituted with alkoxy or hydroxy.

26. A compound according to any one of claims 1, 5, or 10, wherein A¹ is 1,3-benzothiadiazol-4-yl, t-butoxy, butoxy, n-butoxy, cyclohexyl, 2,2-dimethylpropoxy, ethoxy, furan-3-yl, isoxazol-3-yl, methoxy, methyl, 2-methylpropoxy, phenyl, piperidin-3-yl, piperidin-4-yl, n-propoxy, pyridin-2-yl, pyridin-3-yl, pyridin-4-yl, pyrazin-2-yl, tetrahydrofuran-2-yl, tetrahydrofuran-3-yl, tetrahydro-2H-pyran-4-yl, 1H-tetrazol-1-yl, 2H-tetrazol-2-yl, thiazol-4-yl, 1,3,4-thiadiazol-2-yl, 1,3-benzothiadiazol-6-yl, 3,3-dihydrobenzo[1,2,3]thiadiazol-4-yl, benzimidazol-2-yl, benzimidazol-6-yl, benzo[1,2,5]thiadiazole, benzoxadiazol-4-yl, cyclopentyl, imidazol-4-yl, indazol-6-y, isooxazol-5-yl, morpholin-2-yl, morpholino, oxazol-4-yl, piperidin-N-yl, pyrazol-3-yl, pyrrolidin-2-yl, pyrrolidin-3-yl, pyrrolidin-N-yl, tetrazol-5-yl, or thiadiazol-4-yl.

27. A compound according to any one of claims 1, 5, or 10, wherein $A^1$ is a substituted aryl or heteroaryl group selected from the group consisting of 5-methyl-2H-imidazol-4-yl, 2-aminothiazol-4-yl, 4-t-butylphenyl, 2-chlorophenyl, 2-chloro-6-methylpyrid-4-yl, 3-chlorophenyl, 4-chlorophenyl, 6-chloropyridin-3-yl, 3,4-dichlorophenyl, 2,4-difluorophenyl, 1,5-dimethyl-1H-pyrazol-3-yl, 2,4-dimethylthiazol-5-yl, 1-ethyl-3-methyl-1H-pyrazol-5-yl, 2-methoxyphenyl, 4-methoxyphenyl, 4-methylisoxazol-3-yl, 5-methylisoxazol-4-yl, 4-methylphenyl, 1-methyl-3-trifluoromethyl-1H-pyrazol-4-yl, 1-methyl-5-chloro-1H-pyrazol-4-yl, 5-methyl-1H-pyrazol-3-yl, 6-methylpyridin-3-yl, 2-pyrrolidin-3-ylphenyl, 4-(trifluoromethyl)phenyl, 6-(trifluoromethyl)pyridin-3-yl, 2,5-dimethyloxazol-4-yl, 2-aminothiazol-4-yl, 4-methylpyrazol-5-yl, 3-trifluoromethylpyrazol-4-yl, 2-methyl-3-trifluoromethylpyrazol-5-yl, 4-chloro-1,3-dimethylpyrazolo[3,4]pyridine, and 1-methylbenzimidazol-2-yl.

28. A compound according to any one of claims 1, 5, or 10, wherein $A^1$ is a substituted heterocyclic or cycloalkyl selected from the group consisting of 3-[(aminoacetyl)amino]cyclohexyl, 3-(2-aminoethylsulfonylamino)cyclohexyl, 1-methylpiperazin-4-yl, 1-methylcarbonylpiperidin-4-yl, 1-methoxycarbonylpiperidin-4-yl, quinuclidin-3-yl, 2-oxopyrrolidin-5-yl, 2-oxopyrrolidin-4-yl, 2-oxo-dihydrofuran-5-yl, 2-oxothiazolidin-4-yl, and 3-hydroxypyrrolidin-5-yl.

29. A compound according to any one of claims 1, 5, or 10, wherein $A^1$ is a substituted alkyl selected from the group consisting of 3-amino-2-oxo-1(2H)-pyridinylmethyl, cyanomethyl, (N,N-dimethylamino)methyl, ethoxymethyl, p-fluorophenoxymethyl, hydroxymethyl, 1H-imidazol-1-ylmethyl, methoxymethyl, (N-methylamino)methyl, methylsulfonylmethyl, (5-methyl-1H-tetrazol-1-yl)methyl, (5-methyl-2H-tetrazol-2-yl)methyl, morpholin-4-ylmethyl, 1H-pyrazol-1-ylmethyl, 1H-1,2,3-triazol-1-ylmethyl, 2H-1,2,3-triazol-2-ylmethyl, 1H-1,2,4-triazol-1-ylmethyl, 2H-1,2,4-triazol-2-ylmethyl, 4H-1,2,4-triazol-4-ylmethyl, 1H-tetrazol-1-ylmethyl, 1H-tetrazol-5-ylmethyl, 2H-tetrazol-2-ylmethyl, imidazol-4-ylmethyl, 1-methylpyrazol-3-ylmethyl, piperidin-4-ylmethyl, trifluoromethyl, dimethylaminoethyl, and 2-oxo-3-aminopyrrolidin-1-ylmethyl.

30. A compound according to any one of claims 1, 5, or 10, wherein $A^1$ is $NR^8R^9$.

31. A compound of claim 30, wherein $R^8$ is hydrogen.

32. A compound of claim 30, wherein $R^8$ and $R^9$ are hydrogen.

33. A compound of claim 30, wherein $R^9$ is selected from the group consisting of alkyl, substituted alkyl, and cycloalkyl.

34. A compound of claim 33, wherein $R^9$ is selected from the group consisting of methyl, hydroxymethyl, methoxymethyl, methoxyethyl, furan-2-ylmethyl, 2-hydroxyethyl, cyclopropyl and isopropyl.

35. A compound of claim 30, wherein $R^9$ is aryl or substituted aryl.

36. A compound of claim 35, wherein $R^9$ is selected from the group consisting of 4-cyanophenyl, 3,4-difluorophenyl, 2,3,5-trifluorophenyl, 3,5-dinitrophenyl, and phenyl.

37. A compound of claim 30, wherein $R^9$ is heteroaryl or substituted heteroaryl.

38. A compound of claim 37, wherein $R^9$ is selected from the group consisting of thiophen-2-yl, 3,5-dimethylisoxazol-4-yl, and 2,6-dichloropyridin-4-yl.

39. A compound of claim 30, wherein $R^9$ is a heterocycloalkyl or substituted heterocycloalkyl group.

40. A compound of claim 39, wherein $R^9$ is tetrahydropyran-4-yl or 4-(ethoxycarbonyl)piperidin-4-yl.

41. A compound of claim 30, wherein $R^9$ is a hydroxy.

42. A compound of claim 30, wherein $R^8$ and $R^9$ are cyclized with the nitrogen atom bound thereto to form a heterocyclic or substituted heterocyclic $—NR^8R^9$ that is selected from the group consisting of thiamorpholin-N-yl, 1,1-dioxothiamorpholin-N-yl, 1-oxothiamorpholin-1-yl, 2-(aminomethylene)pyrrolidin-N-yl, 2-(methoxycarbonyl)pyrrolidin-N-yl, 2,6-dimethylmorpholin-N-yl, 3-hydroxypiperidin-N-yl, 3-hydroxypyrrolidin-N-yl, 4-(butylsulfonyl)piperazin-N-yl, 4-(cyclopropylsulfonyl)piperazin-N-yl, 4-(dimethylamino)piperidin-N-yl, 4-(ethoxycarbonyl)piperazin-N-yl, 4-(ethylsulfonyl)piperazin-N-yl, 4-(isopropylsulfonyl)piperazin-N-yl, 4-(methylcarbonyl)piperazin-N-yl, 4-(methylsulfonyl)piperidin-N-yl, 4-(methysulfonyl)piperazin-N-yl, 4-(morpholin-N-yl)piperidin-N-yl, 4-(piperidin-N-yl)piperidin-N-yl, 4-(propylsulfonyl)piperazin-N-yl, 4-cyclohexylpiperazin-N-yl, 4-hydroxypiperidin-N-yl, 4-isopropylpiperazin-4-yl, 4-methylpiperidin-N-yl, isoxazolidin-2-yl, morpholin-N-yl, piperazin-N-yl, piperidin-N-yl, 2-(hydrazinocarbonyl)pyrrolidin-N-yl, and pyrrolidin-N-yl.

43. A compound according to any one of claims 1, 5, or 10, wherein $R^4$ is substituted alkyl.

44. A compound of claim 43, wherein $R^4$ is alkyl substituted with 1 to 5 substituents selected from the group consisting of amino, substituted amino, halo, alkoxy, substituted alkoxy, and hydroxy.

45. A compound according to any one of claims 1, 5, or 10, wherein $R^4$ is selected from the group consisting of hydrogen, piperidin-4-yl, $—(CH_2)_2—NH_2$, $—CH_2$-azetidin-3-yl, $—CH_2$-(2,5-dihydropyrrol-3-yl), $—(CH_2)_3$-imidazol-1-yl, $—CH_2$-(1H-imidazol-4-yl), $—CH_2$-pyridin-3-yl, $—CH_2$-(2-hydroxypyridin-4-yl), $—CH_2$-(6-hydroxypyridin-3-yl), $—CH_2$-morpholin-2-yl, $—CH_2$-pyrrolidin-3-yl, $—CH_2$-(3-fluoropyrrolidin-3-yl), $—CH_2$-(3-hydroxypyrrolidin-3-yl), $—CH_2$-(4-fluoropyrrolidin-3-yl), $—CH_2$-(4-hydroxypyrrolidin-3-yl), $—CH_2$-(2-hydroxymethylpyrrolidin-3-yl), $—CH_2$-piperidin-3-yl, $—CH_2$-[1H-(1,2,3-triazol-4-yl)], $—CH_2CH(NH_2)CH_2OH$, $—(CH_2)_3—OH$, $—(CH_2)_3—O(CO)$-phenyl, $—(CH_2)_3—NH_2$, $—(CH_2)_3—NHCH_3$, $—(CH_2)_3—N(CH_3)_2$, $—(CH_2)_3—NHOCH_3$, $—(CH_2)_3—NHSO_2CH_3$, $—(CH_2)_3NH$-(5-cyanopyridin-2-yl), $—(CH_2)_3NH$-cyclopropyl, $—(CH_2)_3NH$-cyclobutyl, $—(CH_2)_3$-(1H-imidazol-2-yl), $—(CH_2)_3$(2-hydroxyethylpiperidin-1-yl), $—(CH_2)_3NH$(2-hydroxymethylphenyl), $—(CH_2)_3NH$-(5-trifluoromethylpyridin-2-yl), $—(CH_2)_3NHCH_2$-cyclopropyl, $—(CH_2)_3NHCH_2$-{5-(pyridin-3-yloxy)-1H-indazol-3-yl}, $—(CH_2)_3NHCH_2$-(5-methoxy-1H-indazol-3-yl), $—(CH_2)_3NHCH_2$-(6-fluoro-1H-indazol-3-yl), $—CH_2CHOHCH_2NH_2$, $—CH_2CH(CH_2OH)CH_2NH_2$, $—CH_2C(CH_3)_2CH_2—N(CH_3)_2$, $—CH_2C(CH_3)_2CH_2$-(4-methylpiperazin-1-yl), $—(CH_2)_2C(O)NH_2$, $—(CH_2)_2CH(NH_2)C(O)NH_2$, $—(CH_2)_2CH(NH_2)C(O)OH$, $—(CH_2)_2CH(NH_2)CH_2C(O)NH_2$, $—(CH_2)_2CH(NH_2)CH_2OH$, $—(CH_2)_2CH(NH_2)CH_3$, $—(CH_2)_3NHC(O)CH_2NH_2$, $—(CH_2)_3NHC(O)CH(NH_2)CH(CH_3)_2$, $—CH_2CHFCH_2NH_2$, $—(CH_2)_2NHC(O)CH_2NH_2$, $—(CH_2)_3—NHCH_2CH_2OH$, $—(CH_2)_3—NHCH_2CO_2H$, $—(CH_2)_3NHCH_2CO_2CH_2CH_3$, $—(CH_2)_3—N(CH_2CH_2OH)_2$, $—(CH_2)_3—NHCH(CH_2OH)_2$, $—(CH_2)_3CH_3$, $—(CH_2)_2CH(NH_2)CH_2OH$, $—(CH_2)_2C(CH_3)_2NH_2$, $—(CH_2)_2CH(NH_2)CH_2OCH_3$, $—(CH_2)_2CH(NH_2)CH_2F$, $—CH_2CHFCH(NH_2)CH_2OH$, and $—(CH_2)_2$-spirocylcopropyl-$NH_2$.

46. A compound according to any one of claims 1, 5, or 10, wherein $R^4$ is selected from the group consisting of $—(CH_2)_3NH_2$, $—(CH_2)_2CH(CH_2OH)NH_2$, $—CH_2CH(F)CH_2NH_2$, —CH$_2$-[2-(CH$_2$OH)pyrrolidin-3-yl], —CH$_2$-[4-(OH)pyrrolidin-3-yl], —CH$_2$—C(F)(spiropyrrolidin-3-yl), —(CH$_2$)$_2$CH(CH$_2$F)NH$_2$, —(CH$_2$)$_2$C(CH$_3$)$_2$NH$_2$, —(CH$_2$)$_2$CH(CH$_3$)NH$_2$, and —(CH$_2$)CH(CH$_2$OCH$_3$)NH$_2$.

47. A compound according to any one of claims 1, 5, or 10, wherein R$^3$ and R$^4$ or A$^1$ and R$^4$ together with the atoms bound respectively thereto join to form a five to seven membered heterocycloalkyl or substituted heterocycloalkyl group.

48. A compound of claim 47, wherein the heterocycloalkyl or substituted heterocycloalkyl group is selected from the group consisting of:

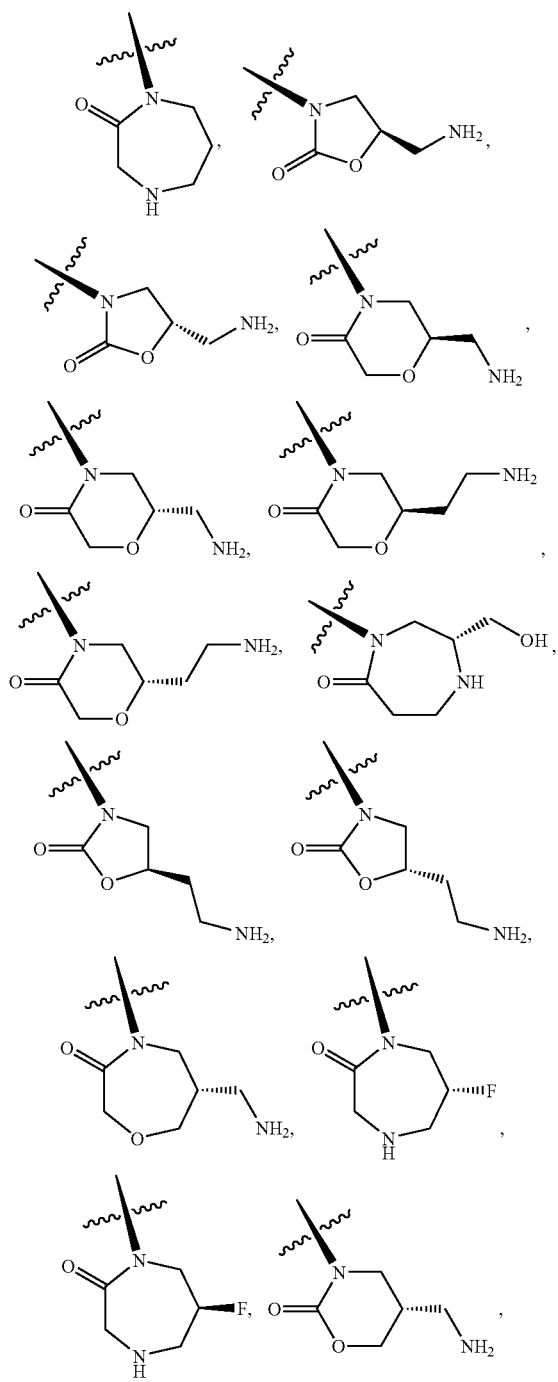
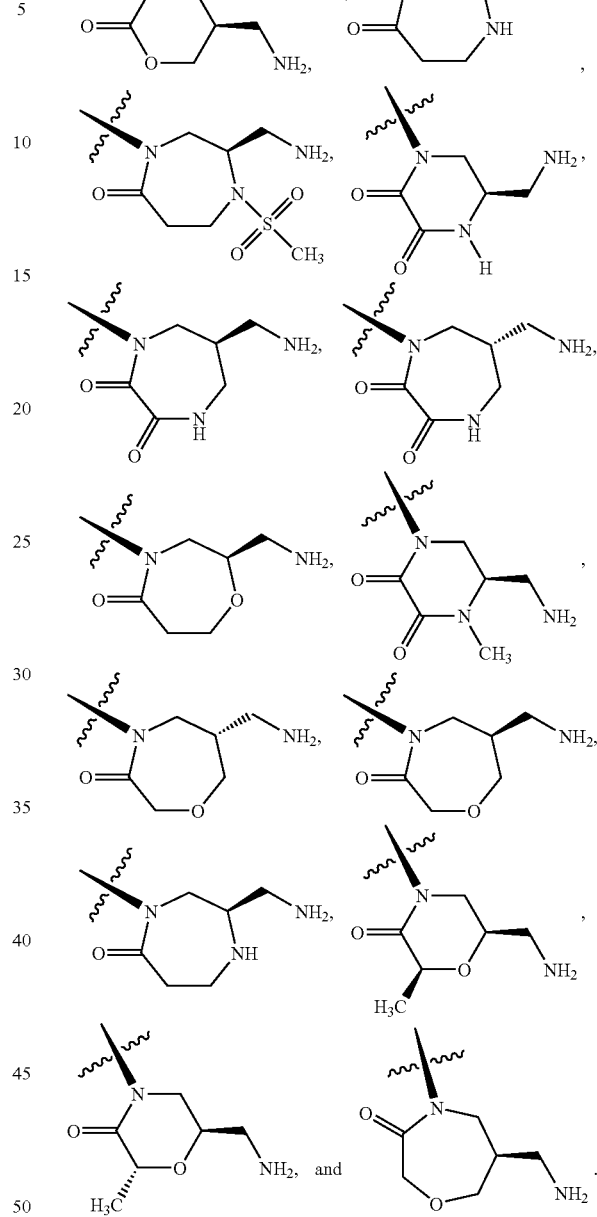

49. A compound according to any one of claims 1, 5, or 10, wherein R$^6$ is aryl or substituted aryl and is selected from the group consisting of phenyl, 3-chlorophenyl, 3-fluorophenyl, 2,5-difluorophenyl, and 2,3,5-trifluorophenyl.

50. A compound according to any one of claims 1, 5, or 10, wherein R$^6$ is selected from the group consisting of phenyl, 3-bromophenyl, 3-chlorophenyl, 4-cyanophenyl, 3,5-difluorophenyl, 3-fluorophenyl, 2-methoxyphenyl, 3-methoxyphenyl, 4-methoxyphenyl, 4-methylphenyl, pyrazin-2-yl, pyridin-2-yl, thiazol-2-yl, 2-trifluoromethylphenyl, and 3-trifluoromethylphenyl.

51. A compound according to any one of claims 1, 5, or 10, wherein A$^2$ is selected from the group consisting of phenyl, 6-aminopyridin-2-yl, 3-chlorophenyl, 3-cyanophenyl, 2,4-difluorophenyl, 2,5-difluorophenyl, 3,5-difluorophenyl, 2-fluorophenyl, 3-fluorophenyl, 4-fluorophenyl, 3-hydroxyphenyl, 3-methoxyphenyl, 1-(5-methyl)-isoxazol-3-yl, 2-methylphenyl, 3-methylphenyl, 4-methylphenyl, pyridin-2-yl, pyridin-3-yl, pyridin-4-yl, tetrahydropyran-4-yl, thiazol-4-yl, and 5-trifluoromethylfuran-2-yl.

52. A compound according to any one of claims 1, 5, or 10, wherein $L^2$ is methylene and $A^2$ is selected from the group consisting of phenyl, 3-fluorophenyl, or 3-hydroxyphenyl.

53. A compound according to any one of claims 1, 5, or 10, wherein $R^7$ is benzyl.

54. A compound according to any one of claims 1, 5, or 10, wherein $R^1$ is t-butyl, $L^2$ is methylene, $A^2$ is phenyl, and $R^6$ is phenyl or substituted phenyl.

55. A compound of claim 54, wherein $R^1$ is t-butyl, $L^2$ is methylene, $A^1$ is phenyl, $R^6$ is phenyl substituted with 1 to 2 halo substituents.

56. A compound according to any one of claims 1, 5, or 10, wherein $R^1$ is t-butyl, $R^2$ is hydrogen, $L^2$ is methylene, $A^2$ is phenyl, $R^4$ is substituted alkyl.

57. A compound of claim 56, wherein $R^4$ is —$(CH_2)_3NH_2$, —$CH_2CH(F)CH_2NH_2$, —$(CH_2)_2CH(CH_2F)NH_2$, —$(CH_2)_2CH(CH_2OCH_3)NH_2$, —$(CH_2)_2CH(CH_3)NH_2$, —$(CH_2)_2C(CH_3)_2NH_2$ or —$(CH_2)_2CH(CH_2OH)NH_2$.

58. A pharmaceutical composition comprising a therapeutically effective amount of a compound of claim 1 and a pharmaceutically acceptable carrier.

59. The composition of claim 58 further comprising at least one agent for the treatment of cancer.

60. The composition of claim 59, wherein the agent for the treatment of cancer is selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

61. A method for inhibiting KSP kinesin in a mammalian patient, wherein said method comprises administering to the patient an effective KSP-inhibiting amount of a compound of claim 1.

62. A compound of claim 1 selected from
N—((S)-3-amino-4-fluorobutyl)-N—((R)-1-(1-benzyl-3-(2,5-difluorophenyl)-1H-1,2,4-triazol-5-yl)-2,2-dimethylpropyl)nicotinamide;
N—((S)-3-amino-4-fluorobutyl)-N—((R)-1-(1-benzyl-3-(2,5-difluorophenyl)-1H-1,2,4-triazol-5-yl)-2,2-dimethylpropyl)morpholine-4-carboxamide;
N—((S)-3-amino-4-fluorobutyl)-N—((R)-1-(1-benzyl-3-(2,5-difluorophenyl)-1H-1,2,4-triazol-5-yl)-2,2-dimethylpropyl)-2-methoxyacetamide;
N—((S)-3-amino-4-fluorobutyl)-N—((R)-1-(1-benzyl-3-(2,5-difluorophenyl)-1H-1,2,4-triazol-5-yl)-2,2-dimethylpropyl)-2-hydroxyacetamide;
N—((R)-3-amino-4-fluorobutyl)-N—((R)-1-(1-benzyl-3-(2,5-difluorophenyl)-1H-1,2,4-triazol-5-yl)-2,2-dimethylpropyl)piperidine-1-carboxamide;
N—((R)-3-amino-4-fluorobutyl)-N—((R)-1-(1-benzyl-3-(2,5-difluorophenyl)-1H-1,2,4-triazol-5-yl)-2,2-dimethylpropyl)morpholine-4-carboxamide;
(2S,6R)—N—((R)-3-amino-4-fluorobutyl)-N—((R)-1-(1-benzyl-3-(2,5-difluorophenyl)-1H-1,2,4-triazol-5-yl)-2,2-dimethylpropyl)-2,6-dimethylmorpholine-4-carboxamide;
1-((R)-3-amino-4-fluorobutyl)-1-((R)-1-(1-benzyl-3-(2,5-difluorophenyl)-1H-1,2,4-triazol-5-yl)-2,2-dimethylpropyl)-3,3-dimethylurea;
1-((R)-3-amino-4-fluorobutyl)-1-((R)-1-(1-benzyl-3-(2,5-difluorophenyl)-1H-1,2,4-triazol-5-yl)-2,2-dimethylpropyl)-3-methylurea;
(2S,6R)—N—((S)-3-amino-4-fluorobutyl)-N—((R)-1-(1-benzyl-3-(2,5-difluorophenyl)-1H-1,2,4-triazol-5-yl)-2,2-dimethylpropyl)-2,6-dimethylmorpholine-4-carboxamide;
1-((S)-3-amino-4-fluorobutyl)-1-((R)-1-(1-benzyl-3-(2,5-difluorophenyl)-1H-1,2,4-triazol-5-yl)-2,2-dimethylpropyl)-3,3-dimethylurea;
1-((S)-3-amino-4-fluorobutyl)-1-((R)-1-(1-benzyl-3-(2,5-difluorophenyl)-H-1,2,4, triazol-5-yl)-2,2-dimethylpropyl)-3-methylurea;
N—((R)-3-amino-4-fluorobutyl)-N—((R)-1-(1-benzyl-3-(2,5-difluorophenyl)-1H-1,2,4-triazol-5-yl)-2,2-dimethylpropyl)thiomorpholine-4-carboxamide;
N—((S)-3-amino-4-fluorobutyl)-N—((R)-1-(1-benzyl-3-(2,5-difluorophenyl)-1H-1,2,4-triazol-5-yl)-2,2-dimethylpropyl)thiomorpholine-4-carboxamide;
N—((S)-3-amino-4-fluorobutyl)-N((R)-1-(1-benzyl-3-(2,5-difluorophenyl)-1H-1,2,4-triazol-5-yl)-2,2-dimethylpropyl)piperidine-1-carboxamide;
(R)-6-(aminomethyl)-4-((R)-1-(1-benzyl-3-phenyl-1H-1,2,4-triazol-5-yl)-2,2-dimethylpropyl)-1,4-oxazepan-3-one; and
(S)-6-(aminomethyl)-4-((R)-1-(1-benzyl-3-(2,5-difluorophenyl)-1H-1,2,4-triazol-5-yl)-2,2-dimethylpropyl)-1,4-oxazepan-3-one;
or a pharmaceutically acceptable salt, ester, or prodrug thereof.

63. A compound of claim 1 selected from
N—((R)-3-amino-4-fluorobutyl)-N—((R)-1-(2-benzyl-5-(2,5-difluorophenyl)-2H-1,2,4-triazol-3-yl)-2,2-dimethylpropyl)-2-hydroxyacetamide;
N—((R)-3-amino-4-fluorobutyl)-N—((R)-1-(2-benzyl-5-(2,5-difluorophenyl)-2H-1,2,4-triazol-3-yl)-2,2-dimethylpropyl)nicotinamide;
N—((R)-3-amino-4-fluorobutyl)-N—((R)-1-(2-benzyl-5-(2,5-difluorophenyl)-2H-1,2,4-triazol-3-yl)-2,2-dimethylpropyl)-1,1-dioxothiomorpholine-4-carboxamide;
N—((S)-3-amino-4-fluorobutyl)-N—((R)-1-(2-benzyl-5-(2,5-difluorophenyl)-2H-1,2,4-triazol-3-yl)-2,2-dimethylpropyl)-1,1-dioxothiomorpholine-4-carboxamide;
(2R)—N—((S)-3-amino-4-fluorobutyl)-N—((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide;
(2S)—N—((S)-3-amino-4-fluorobutyl)-N—((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide;
(2R)—N—((R)-3-amino-4-fluorobutyl)-N—((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide;
(2S)—N—((R)-3-amino-4-fluorobutyl)-N—((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide;
(2S)—N—((S)-3-amino-4-fluorobutyl)-N—((R)-1-(2-benzyl-5-(2,5-difluorophenyl)-2H-1,2,4-triazol-3-yl)-2,2-dimethylpropyl)-2-hydroxypropanamide;
N-(3-aminopropyl)-N—((R)-1-(2-benzyl-5-(2,5-difluorophenyl)-2H-1,2,4-triazol-3-yl)-2,2-dimethylpropyl)nicotinamide;
(2S)—N-(3-aminopropyl)-N—((R)-1-(2-benzyl-5-(2,5-difluorophenyl)-2H-1,2,4-triazol-3-yl)-2,2-dimethylpropyl)-2-hydroxypropanamide;

N-(3-aminopropyl)-N—((R)-1-(2-benzyl-5-(2,5-difluorophenyl)-2H-1,2,4-triazol-3-yl)-2,2-dimethylpropyl)-2-hydroxyacetamide;
(2S)—N-(3-aminopropyl)-N—((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide;
N-(3-aminopropyl)-N—((R)-1-(2-benzyl-5-(2,5-difluorophenyl)-2H-1,2,4-triazol-3-yl)-2,2-dimethylpropyl)morpholine-4-carboxamide;
(2S,6R)—N-(3-aminopropyl)-N—((R)-1-(2-benzyl-5-(2,5-difluorophenyl)-2H-1,2,4-triazol-3-yl)-2,2-dimethylpropyl)-2,6-dimethylmorpholine-4-carboxamide;
N-(3-aminopropyl)-N—((R)-1-(2-benzyl-5-(2,5-difluorophenyl)-2H-1,2,4-triazol-3-yl)-2,2-dimethylpropyl)-4-(methylsulfonyl)piperazine-1-carboxamide;
(2S)—N—((R)-3-amino-4-fluorobutyl)-N—((R)-1-(2-benzyl-5-(2,5-difluorophenyl)-2H-1,2,4-triazol-3-yl)-2,2-dimethylpropyl)-2-hydroxypropanamide;
(2S)—N—((S)-3-amino-2-fluoropropyl)-N—((R)-1-(2-benzyl-5-(2,5-difluorophenyl)-2H-1,2,4-triazol-3-yl)-2,2-dimethylpropyl)-2-(hydroxymethyl)pyrrolidine-1-carboxamide;
(2S,6R)—N—((S)-3-amino-2-fluoropropyl)-N—((R)-1-(2-benzyl-5-(2,5-difluorophenyl)-2H-1,2,4-triazol-3-yl)-2,2-dimethylpropyl)-2,6-dimethylmorpholine-4-carboxamide;
N—((S)-3-amino-2-fluoropropyl)-N—((R)-1-(2-benzyl-5-(2,5-difluorophenyl)-2H-1,2,4-triazol-3-yl)-2,2-dimethylpropyl)-2-hydroxyacetamide;
(2S)—N—((S)-3-amino-4-fluorobutyl)-N—((R)-1-(2-benzyl-5-(2,5-difluorophenyl)-2H-1,2,4-triazol-3-yl)-2,2-dimethylpropyl)-tetrahydrofuran-2-carboxamide;
(2S)—N—((R)-3-amino-4-fluorobutyl)-N—((R)-1-(2-benzyl-5-(2,5-difluorophenyl)-2H-1,2,4-triazol-3-yl)-2,2-dimethylpropyl)-tetrahydrofuran-2-carboxamide;
N—((S)-3-amino-4-fluorobutyl)-N—((R)-1-(2-benzyl-5-(2,5-difluorophenyl)-2H-1,2,4-triazol-3-yl)-2,2-dimethylpropyl)-6-methylpyridine-3-carboxamide;
N—((S)-3-amino-4-fluorobutyl)-N—((R)-1-(2-benzyl-5-(2,5-difluorophenyl)-2H-1,2,4-triazol-3-yl)-2,2-dimethylpropyl)isonicotinamide;
N—((S)-3-amino-4-fluorobutyl)-N—((R)-1-(2-benzyl-5-(2,5-difluorophenyl)-2H-1,2,4-triazol-3-yl)-2,2-dimethylpropyl)picolinamide;
N—((S)-3-amino-4-fluorobutyl)-N—((R)-1-(2-benzyl-5-(2,5-difluorophenyl)-2H-1,2,4-triazol-3-yl)-2,2-dimethylpropyl)-2-(methyl sulfonyl)acetamide;
N—((S)-3-amino-2-fluoropropyl)-N—((R)-1-(2-benzyl-5-(2,5-difluorophenyl)-2H-1,2,4-triazol-3-yl)-2,2-dimethylpropyl)nicotinamide;
(2S)—N—((S)-3-amino-2-fluoropropyl)-N—((R)-1-(2-benzyl-5-(2,5-difluorophenyl)-2H-1,2,4-triazol-3-yl)-2,2-dimethylpropyl)-2-hydroxypropanamide;
N—((R)-1-(2-(3-bromobenzyl)-5-(2,5-difluorophenyl)-2H-1,2,4-triazol-3-yl)-2,2-dimethylpropyl)-N—((S)-3-amino-4-fluorobutyl)-2-hydroxyacetamide;
(2S)—N—((R)-1-(2-(3-bromobenzyl)-5-(2,5-difluorophenyl)-2H-1,2,4-triazol-3-yl)-2,2-dimethylpropyl)-N—((S)-3-amino-4-fluorobutyl)-2-hydroxypropanamide;
N—((R)-1-(2-(3-bromobenzyl)-5-(2,5-difluorophenyl)-2H-1,2,4-triazol-3-yl)-2,2-dimethylpropyl)-N—((S)-3-amino-4-fluorobutyl)nicotinamide;
N—((R)-1-(2-(3-bromobenzyl)-5-(2,5-difluorophenyl)-2H-1,2,4-triazol-3-yl)-2,2-dimethylpropyl)-N—((S)-3-amino-4-fluorobutyl)benzamide;
N—((S)-3-amino-4-fluorobutyl)-N—((R)-1-(2-benzyl-5-(5-chloro-2-fluorophenyl)-2H-1,2,4-triazol-3-yl)-2,2-dimethylpropyl)-2-methoxyacetamide;
N—((S)-3-amino-4-fluorobutyl)-N—((R)-1-(2-benzyl-5-(5-chloro-2-fluorophenyl)-2H-1,2,4-triazol-3-yl)-2,2-dimethylpropyl)-2-hydroxyacetamide;
(S)—N—((S)-3-amino-4-fluorobutyl)-N—((R)-1-(1-benzyl-3-(5-chloro-2-fluorophenyl)-1H-1,2,4-triazol-5-yl)-2,2-dimethylpropyl)-2-hydroxypropanamide;
N—((S)-3-amino-4-fluorobutyl)-N—((R)-1-(1-benzyl-3-(5-chloro-2-fluorophenyl)-1H-1,2,4-triazol-5-yl)-2,2-dimethylpropyl)benzamide;
N—((S)-3-amino-4-fluorobutyl)-N—((R)-1-(1-benzyl-3-(5-chloro-2-fluorophenyl)-1H-1,2,4-triazol-5-yl)-2,2-dimethylpropyl)-4-methylbenzamide;
N—((S)-3-amino-4-fluorobutyl)-N—((R)-1-(1-benzyl-3-(5-chloro-2-fluorophenyl)-1H-1,2,4-triazol-5-yl)-2,2-dimethylpropyl)nicotinamide;
(R)—N—((S)-3-amino-4-fluorobutyl)-N—((R)-1-(1-(3-bromobenzyl)-3-(2,5-difluorophenyl)-1H-1,2,4-triazol-5-yl)-2,2-dimethylpropyl)tetrahydrofuran-2-carboxamide;
(S)—N—((S)-3-amino-4-fluorobutyl)-N—((R)-1-(1-(3-bromobenzyl)-3-(2,5-difluorophenyl)-1H-1,2,4-triazol-5-yl)-2,2-dimethylpropyl)tetrahydrofuran-2-carboxamide;
(R)—N—((S)-3-amino-4-fluorobutyl)-N—((R)-1-(1-benzyl-3-(2,5-difluorophenyl)-1H-1,2,4-triazol-5-yl)-2,2-dimethylpropyl)tetrahydrofuran-2-carboxamide;
(S)—N—((S)-3-amino-4-fluorobutyl)-N—((R)-1-(1-(3-cyanobenzyl)-3-(2,5-difluorophenyl)-1H-1,2,4-triazol-5-yl)-2,2-dimethylpropyl)-2-hydroxypropanamide;
N—((S)-3-amino-4-fluorobutyl)-N—((R)-1-(1-benzyl-3-(5-chloro-2-fluorophenyl)-1H-1,2,4-triazol-5-yl)-2,2-dimethylpropyl)morpholine-4-carboxamide;
(2S,6R)—N—((S)-3-amino-4-fluorobutyl)-N—((R)-1-(1-benzyl-3-(5-chloro-2-fluorophenyl)-1H-1,2,4-triazol-5-yl)-2,2-dimethylpropyl)-2,6-dimethylmorpholine-4-carboxamide;
N—((S)-3-amino-4-fluorobutyl)-N—((R)-1-(1-benzyl-3-(5-chloro-2-fluorophenyl)-1H-1,2,4-triazol-5-yl)-2-methylpropyl)benzamide;
N—((S)-3-amino-4-fluorobutyl)-N—((R)-1-(1-benzyl-3-(5-chloro-2-fluorophenyl)-1H-1,2,4-triazol-5-yl)-2-methylpropyl)-4-methylbenzamide;
N—((S)-3-amino-4-fluorobutyl)-N—((R)-1-(1-benzyl-3-(5-chloro-2-fluorophenyl)-1H-1,2,4-triazol-5-yl)-2-methylpropyl)-2-methoxyacetamide;
N—((S)-3-amino-4-fluorobutyl)-N—((R)-1-(1-benzyl-3-(5-chloro-2-fluorophenyl)-1H-1,2,4-triazol-5-yl)-2-methylpropyl)-2-hydroxyacetamide;
(S)—N—((S)-3-amino-4-fluorobutyl)-N—((R)-1-(1-benzyl-3-(5-chloro-2-fluorophenyl)-1H-1,2,4-triazol-5-yl)-2-methylpropyl)-2-hydroxypropanamide;
(S)—N—((S)-3-amino-4-fluorobutyl)-N((R)-1-(1-benzyl-3-(2,5-difluorophenyl)-1H-1,2,4-triazol-5-yl)-2,2-dimethylpropyl)-2-methoxypropanamide;
(S)—N—((S)-3-amino-4-fluorobutyl)-N—((R)-1-(3-(2,5-difluorophenyl)-1-(3-methylbenzyl)-1H-1,2,4-triazol-5-yl)-2,2-dimethylpropyl)-2-hydroxypropanamide;
(2S,6R)—N—((S)-3-amino-4-fluorobutyl)-N—((R)-1-(3-(2,5-difluorophenyl)-1-(3-methylbenzyl)-1H-1,2,4-triazol-5-yl)-2,2-dimethylpropyl)-2,6-dimethylmorpholine-4-carboxamide;
(S)—N—((S)-3-amino-4-fluorobutyl)-N((R)-1-(1-benzyl-3-(3,5-difluorophenyl)-1H-1,2,4-triazol-5-yl)-2,2-dimethylpropyl)-2-hydroxypropanamide;

(S)—N—((S)-3-amino-4-fluorobutyl)-N—((R)-1-(1-benzyl-3-(3,5-dichlorophenyl)-1H-1,2,4-triazol-5-yl)-2,2-dimethylpropyl)-2-hydroxypropanamide;

(2S,6R)—N—((S)-3-amino-4-fluorobutyl)-N—((R)-1-(1-benzyl-3-(3,5-difluorophenyl)-1H-1,2,4-triazol-5-yl)-2,2-dimethylpropyl)-2,6-dimethylmorpholine-4-carboxamide;

(S)—N—((S)-3-amino-4,4-difluorobutyl)-N—((R)-1-(1-benzyl-3-(2,5-difluorophenyl)-1H-1,2,4-triazol-5-yl)-2,2-dimethylpropyl)-2-hydroxypropanamide;

(S)—N—((R)-3-amino-4,4-difluorobutyl)-N—((R)-1-(1-benzyl-3-(2,5-difluorophenyl)-1H-1,2,4-triazol-5-yl)-2,2-dimethylpropyl)-2-hydroxypropanamide;

(S)—N—((R)-3-amino-4,4-difluorobutyl)-N—((R)-1-(3-(2,5-difluorophenyl)-1-(3-methylbenzyl)-1H-1,2,4-triazol-5-yl)-2,2-dimethylpropyl)-2-hydroxypropanamide;

(S)—N—((S)-3-amino-4,4-difluorobutyl)-N—((R)-1-(1-(3-cyanobenzyl)-3-(2,5-difluorophenyl)-1H-1,2,4-triazol-5-yl)-2,2-dimethylpropyl)-2-hydroxypropanamide;

(S)—N—((R)-3-amino-4,4-difluorobutyl)-N—((R)-1-(1-(3-cyanobenzyl)-3-(2,5-difluorophenyl)-1H-1,2,4-triazol-5-yl)-2,2-dimethylpropyl)-2-hydroxypropanamide;

(S)—N—((R)-3-amino-4,4-difluorobutyl)-N—((R)-1-(3-(2,5-difluorophenyl)-1-(3-(trifluoromethyl)benzyl)-1H-1,2,4-triazol-5-yl)-2,2-dimethylpropyl)-2-hydroxypropanamide;

(S)—N—((S)-3-amino-4,4-difluorobutyl)-N—((R)-1-(3-(2,5-difluorophenyl)-1-(3-methylbenzyl)-1H-1,2,4-triazol-5-yl)-2,2-dimethylpropyl)-2-hydroxypropanamide;

(S)—N—((S)-3-amino-4,4-difluorobutyl)-N—((R)-1-(3-(2,5-difluorophenyl)-1-(3-(trifluoromethyl)benzyl)-1H-1,2,4-triazol-5-yl)-2,2-dimethylpropyl)-2-hydroxypropanamide;

(S)—N—((S)-3-amino-4,4-difluorobutyl)-N—((R)-1-(1-(3-bromobenzyl)-3-(2,5-difluorophenyl)-1H-1,2,4-triazol-5-yl)-2,2-dimethylpropyl)-2-hydroxypropanamide;

(S)—N—((R)-3-amino-4,4-difluorobutyl)-N—((R)-1-(1-(3-bromobenzyl)-3-(2,5-difluorophenyl)-1H-1,2,4-triazol-5-yl)-2,2-dimethylpropyl)-2-hydroxypropanamide;

(S)—N—((S)-3-amino-4-fluorobutyl)-N—((R)-1-(1-benzyl-3-(2-chloro-5-fluorophenyl)-1H-1,2,4-triazol-5-yl)-2,2-dimethylpropyl)-2-hydroxypropanamide;

(S)—N—((S)-3-amino-4-fluorobutyl)-N—((R)-1-(1-benzyl-3-(5-chloro-2-fluorophenyl)-1H-1,2,4-triazol-5-yl)-2-methylpropyl)-3-(hydroxymethyl)morpholine-4-carboxamide;

(S)—N—((S)-3-amino-4,4-difluorobutyl)-N—((R)-1-(3-(2,5-difluorophenyl)-1-(3-isopropylbenzyl)-1H-1,2,4-triazol-5-yl)-2,2-dimethylpropyl)-2-hydroxypropanamide; and (S)—N—((R)-3-amino-4,4-difluorobutyl)-N—((R)-1-(3-(2,5-difluorophenyl)-1-(3-isopropylbenzyl)-1H-1,2,4-triazol-5-yl)-2,2-dimethylpropyl)-2-hydroxypropanamide;

or a pharmaceutically acceptable salt, ester, or prodrug thereof.

\* \* \* \* \*